United States Patent [19]
Desai et al.

[11] Patent Number: 5,852,031
[45] Date of Patent: Dec. 22, 1998

[54] 2,7-SUBSTITUTED OCTAHYDRO-1H-PYRIDO[1,2-A]PYRAZINE DERIVATIVES

[75] Inventors: Kishor A. Desai, Ledyard; Anton F. J. Fliri, Norwich; Mark A. Sanner, Old Saybrook, all of Conn.

[73] Assignee: Pfizer Inc., New York, N.Y.

[21] Appl. No.: 809,145

[22] PCT Filed: Aug. 24, 1995

[86] PCT No.: PCT/IB95/00689

§ 371 Date: Mar. 26, 1997

§ 102(e) Date: Mar. 26, 1997

[87] PCT Pub. No.: WO96/10571

PCT Pub. Date: Apr. 11, 1996

Related U.S. Application Data

[63] Continuation of Ser. No. 315,470, Sep. 20, 1994, abandoned.

[51] Int. Cl.$^6$ .................... C07D 471/04; A61K 31/505
[52] U.S. Cl. ................... 514/279; 544/238; 544/295; 544/359
[58] Field of Search ..................... 544/238, 295, 544/359; 514/249

[56] References Cited

U.S. PATENT DOCUMENTS

| | | | |
|---|---|---|---|
| 3,388,128 | 6/1968 | Day et al. | 260/268 |
| 4,182,763 | 1/1980 | Casten et al. | 424/251 |
| 4,788,290 | 11/1988 | Stack | 544/357 |
| 5,122,525 | 6/1992 | Bright et al. | 514/249 |
| 5,157,034 | 10/1992 | Bright et al. | 514/249 |
| 5,185,449 | 2/1993 | Godek et al. | 546/272 |
| 5,563,150 | 10/1996 | Curtis et al. | 514/300 |
| 5,576,319 | 11/1996 | Baker et al. | 514/253 |

FOREIGN PATENT DOCUMENTS

| | | | |
|---|---|---|---|
| 0107825 | 5/1984 | European Pat. Off. | C07D 471/04 |
| 0173634 | 3/1986 | European Pat. Off. | C07D 295/08 |
| 0237781 | 9/1987 | European Pat. Off. | C07D 401/12 |
| 0361271 | 4/1990 | European Pat. Off. | C07D 401/04 |
| 0380217 | 8/1990 | European Pat. Off. | C07D 471/04 |
| 8705022 | 8/1987 | WIPO | C07D 471/04 |
| 9008144 | 7/1990 | WIPO . | |
| 9213858 | 8/1992 | WIPO . | |
| 9215561 | 9/1992 | WIPO . | |
| 9306101 | 4/1993 | WIPO . | |
| 9325552 | 12/1993 | WIPO . | |
| 9410145 | 5/1994 | WIPO . | |
| 9410162 | 5/1994 | WIPO . | |
| 9420459 | 9/1994 | WIPO . | |
| 9420471 | 9/1994 | WIPO | C07D 215/22 |
| 9420497 | 9/1994 | WIPO | C07D 471/04 |
| 9410145 | 11/1994 | WIPO | C07D 211/32 |
| 9410162 | 11/1994 | WIPO | C07D 401/04 |

OTHER PUBLICATIONS

"Cloning of the gene for a human dopamine $D_4$ receptor with high affinity for the antipsychotic clozapine", Van Tol, et al., Nature 350, 610 (1991).

"Cloning of the gene for a human dopamine $D_5$ receptor with higher affinity for dopamine than $D_1$", Sunahara, et al., Nature 350, 614 (1991).

"Synthesis and 2,7–Funcationalization of the Bicyclic Lactam 2–Benzyloctahydropyrido[1,2–a]pyrazin–6–one", Saleh, et al., J. Org. Chem. 1993 58, 690–695.

"Determination of the active conformation of 6–amino–α–[(4–diphenylmethyl–1–piperazinyl)methyl–9H–purine]–ethanol: a positive inotropic agent", Miltz, et al., Bioorganic Medicinal Chemistry Letters, 3, No. 6, 1233–1239 (1993).

"The synthesis of 2,7–substituted octahydro–2H–pyrido[1,2–1]pyrazines, analogues of quinolizidine and piperazine drugs", Saleh, et al., Tetrahedron, 50, No. 6, pp. 1811–1820, 1994.

Van Tol, H. H. M., et al. "Cloning of the gene for a human dopamine $D_4$ receptor with high affinity for the antipsychotic clozapine," *Letters to Nature*, vol. 350, 18 Apr. 1991, pp. 610–614.

Seeman, P., et al. "Dopamine receptor pharmacology," *Current Opinion in Neurology and Neurosurgery 1993*, 6:602–608.

Seeman, P., et al. "Dopamine D4 receptors elevated in schizophrenia," *Letters to Nature*, vol. 365, 30 Sep. 93, pp. 441–445.

Seeman, P., et al. "Low Density of Dopamine D4 Receptors in Parkinson's Schizophrenia, and Control brain Striata," *Synapse*, 14:247–253 (1993).

Kulagowski, J. J., et al. "Dopamine D4 Receptor Agonists," *Current Pharmaceutical Design*, 1997, 3, 355–366.

"Bromerguride," *Drugs of the Future*, 1988, 13, 403–405.

Reynolds, Drugs 51(1), 7–11, Jan. 1996.

Psychopharmacology (1998) 135: 194–200, Robert S. Mansbach, et al: "Selective Dopamine $D_4$ receptor Anatgonists Reverse Apomorphine–induced Blockade of Prepulse Inhibition".

(List continued on next page.)

*Primary Examiner*—Mark L. Berch
*Attorney, Agent, or Firm*—Peter C. Richardson; Gregg C. Benson; Mervin E. Brokke

[57] ABSTRACT

Substituted pydrido[1,2-a]pyrazines of general formula I wherein Ar and Ar$^1$ represent various carbocyclic and heterocyclic aromatic rings; A represents O, S, SO, SO$_2$, C=O, CHOH, or —(CR$^3$R$^4$) and n is 0–2 as well as precursors thereto are ligands for dopamine receptor subtypes within the body and are therefore useful in the treatment of disorders of the dopamine system.

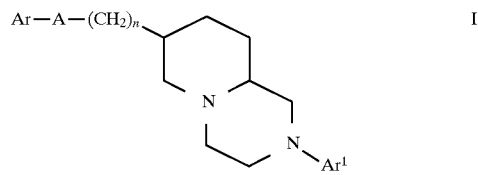

17 Claims, No Drawings

OTHER PUBLICATIONS

Neuropharmacology vol. 33, No. 3/4 pp. 441–448, 1994, T. A. Sipes, et al: "Multiple Serotonin Receptor Subtypes Modulate Prepulse Inhibition of the Startle Response in Rats".

Psychopharmacology (1988) 94:507–514, Robert S. Mansbach, et al: Dopaminergic Stimulation Disrupts Sensorimotor Gating in the Rat.

Krisch et al. The Journal of Pharmacology and Experimental Therapeutics vol. 271, No. 1, Pharmacological Studies with Two New Ergoline Derivatives, the Potential Antipsychotics LEK–8829 and LEK–8841 (1994).

Bioorganic & Medicinal Chemistry Letters 8 (1998) 725–730, Mark A. Sanner, et al: "Synthesis, Sar and Pharmacology of CP–293,019: A Potent, Selective Dopamine $D_4$ Receptor Antagonist".

J. Med. Chem. 1996, 39, 1941–1942, Janusz J. Kulagowski, et al: "3–[(4–(4–Chlorophenyl)piperazin–1–yl]–methyl]–1H–pyrrolo[2,3–b]pyridine: An Antagonist with High Affinity and Selectivity for the Human Dopamine $D_4$ Receptor".

2,7-SUBSTITUTED OCTAHYDRO-1H-PYRIDO[1,2-A]PYRAZINE DERIVATIVES

This is a §371 of International Application PCT/IB95/00689, filed Aug. 24, 1995; which is a continuation of U.S. application Ser. No. 08/315,470, filed Sep. 20, 1994, now abandoned.

The present invention relates to novel pharmacologically active 2,7-substituted octahydro-1H-pyrido[1,2-a]pyrazine derivatives, their acid addition salts, and certain precursors thereto. The compounds of this invention are ligands for dopamine receptor subtypes, especially the dopamine $D_4$ receptor, within the animal body and are therefore useful in the treatment of disorders of the dopamine system.

BACKGROUND OF THE INVENTION

Molecular biological techniques have revealed the existence of several subtypes of the dopamine receptor. The dopamine $D_1$ receptor subtype has been shown to occur in the least two discrete forms. Two forms of the $D_2$ receptor subtype, and at least one form of the $D_3$ receptor subtype, have also been discovered. More recently, the $D_4$ (Van Tol et al., *Nature* (London), 1991, 350, 610) and $D_5$ (Sunahara et al., *Nature* (London), 1991, 350, 614) receptor subtypes have been described.

The compounds in accordance with the present invention, being ligands for dopamine receptor subtypes, especially the dopamine $D_4$ receptor, within the body, are accordingly of use in the treatment, prevention and/or diagnosis of disorders of the dopamine system.

Since dopamine receptors control a great number of pharmacological events and, on the other hand, not all these events are presently known, there is a possibility that compounds that act on the dopamine $D_4$ receptor may exert a wide range of therapeutic effects in animals.

WO 94/10162 and WO 94/10145 report that dopamine ligands are of use in the treatment and/or prevention of disorders of the dopamine system, including schizophrenia, nausea, Parkinson's disease, tardive dyskinesias and extrapyramidal side-effects associated with treatment by conventional neuroleptic agents, neuroleptic malignant syndrome, and disorders of hypothalamic-pituitary function such as hyperprolactinaemia and amenorrhoea.

Upper gastrointestinal tract motility is believed to be under the control of the dopamine system. The compounds according to the present invention may thus be of use in the prevention and/or treatment of gastrointestinal disorders, and the facilitation of gastric emptying.

Dependence-inducing agents such as cocaine and amphetamine have been shown to interact with the dopamine system. Compounds capable of counteracting this effect, including the compounds in accordance with the present invention, may accordingly be of value in the prevention or reduction of dependence on a dependence-inducing agent.

Dopamine is known to be a peripheral vasodilator; for example, it has been shown to exert a dilatory effect on the renal vascular bed. This implies that the compounds of the present invention may be beneficial in controlling vascular blood flow.

The localization of dopamine receptor mRNA in rat heart and large vessels has been noted. This suggests a role for dopamine receptor ligands in controlling cardiovascular function, either by affecting cardiac and smooth muscle contractility or by modulating the secretion of vasoactive substances. The compounds according to the present invention may therefore be of assistance in the prevention and/or treatment of such conditions as hypertension and congestive heart failure.

The presence of D4 receptor mRNA in rat retina has been noted (Cohen, et al. *Proc. Nat. Acad. Sci.*, 1992, 89, 12093), suggesting that dopamine and D4 receptors play a role in ocular function. The compounds of this invention may therefore be useful in the treatment of ocular disorders. Furthermore, D4 receptors influence melatonin biosynthesis in chick retina (Zawilska, Nowak, *Neuroscience Lett.*, 1994, 166, 203), and since melatonin has been used for the treatment of sleep disorders, the compounds of this invention may be useful for the treatment of sleep disorders as well.

Saleh, et al. *Tetrahedron*, 1994, 50, 1811) describe compounds of the formula

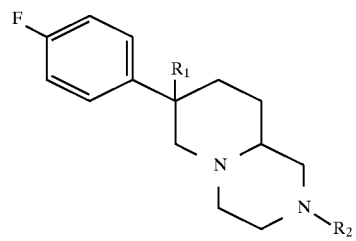

wherein $R_1$ is H or OH and $R_2$ is 2-pyridinyl or 4-$FC_6H_4CO$.

Bright and Desai (U.S. Pat. No. 5,122,525 which is assigned to the assignee hereof) describe optically active or racemic pyrido[1,2-a]pyrazine derivatives of the formula

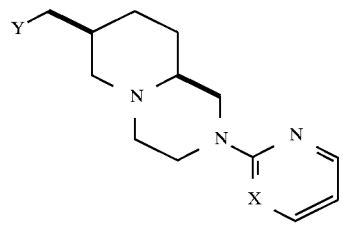

wherein X is N or CH and Y represents certain pyrazolo, triazolo, tetrazolo or cyclo imido radicals. These compounds are anxiolytic agents.

Godek, et al (U.S. Pat. No. 5,185,449 which is assigned to the assignee hereof) describe ($C_1$–$C_3$) alkyl-4,6,7,8,9,9a-hexahydro-2H,3H-pyrido[1,2-a]pyrazine-1-one-7-carboxylate esters which are precursors to bis aza-bicyclic anxiolytics.

WO 93/25552 which is assigned to the assignee hereof discloses processes and intermediates for the synthesis of octahydro-1H-pyrido[1,2-a]pyrazinyl ethyl carboxamide anxiolytic agents; and the anxiolytic agents (+) and (−)-3-oxo-N-[2-[7-(2-(3-(1,2-benzisoxazolyl))-2,3,4,6,(7S),8,9,(9aS)-octahydro-1H-pyrido[1,2a]pyrazinyl]-ethyl]2-oxaspiro-[4,4]-nonane-1-carboxamide.

WO 92/13858 which is assigned to the assignee hereof relates to a process for resolving the enantiomers of 7-(hydroxymethyl)-2-(2-pyrimidinyl)-octahydro-2H-pyrido[1,2-a]pyrazine of the formula

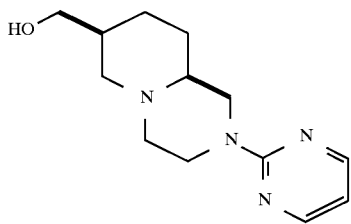

by reacting the racemic mixture with D-(−) or L-(+)tartaric acid, separating the resulting diastereomeric tartrate salts, and converting the tartrate salt of each enantiomer to the free base.

U.S. Pat. No. 5,326,874 is directed to processes for the preparation of a dialkyl trans-piperidine-2,5-dicarboxylate via trans substituted piperidine derivative of the formula

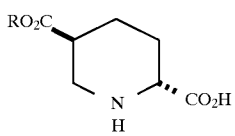

wherein R is $(C_1-C_3)$alkyl. These trans-piperidine derivatives are particularly useful as intermediates in the synthesis of certain neuroleptic, racemic or optically active perhydro-1H-pyridol[1,2-a]pyrazines, which are described in U.S. Pat. No. 5,157,034, having the relative stereochemical formula:

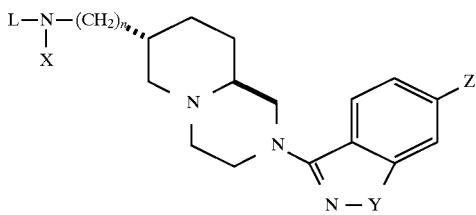

wherein Z is H or Cl; Y is O or S; n is 1, 2, 3 or 4; and L and X are taken either together or separately and represent various H, alkyl, aryl, carbocyclic, or heterocyclic groups.

SUMMARY OF THE INVENTION

This invention relates to compounds of the formula

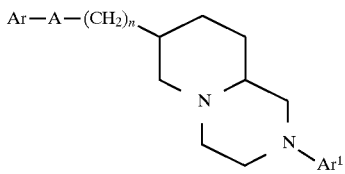

wherein Ar is phenyl, naphthyl, benzoxazolonyl, indolyl, indolonyl, benzimidazolyl, quinolyl, furyl, benzofuryl, thienyl, benzothienyl, oxazolyl, or benzoxazolyl;

$Ar^1$ is phenyl, pyridinyl, pyridazinyl, pyrimidinyl, or pyrazinyl;

A is O, S, SO, $SO_2$, C=O, CHOH, or $-(CR^3R^4)-$;

n is 0, 1 or 2;

each of Ar and $Ar^1$ may be independently and optionally substituted with one to four substituents independently selected from the group consisting of fluoro, chloro, bromo, iodo, cyano, nitro, thiocyano, —SR, —SOR, $—SO_2R$, $—NHSO_2R$, $-(C_1-C_6)$alkoxy, $—NR^1R^2$, $—NRCOR^1$, $—CONR^1R^2$, Ph, —COR, COOR, $-(C_1-C_6)$alkyl, $-(C_1-C_6)$alkyl substituted with one to six halogens, $-(C_3-C_6)$cycloalkyl, and trifluoromethoxy;

each and every R, $R^1$, and $R^2$ is independently selected from the group consisting of hydrogen, $-(C_1-C_6)$alkyl, $-(C_1-C_6)$alkyl substituted with one to thirteen halogens selected from fluorine, chlorine, bromine and iodine, phenyl, benzyl, $-(C_2-C_6)$alkenyl, $-(C_3-C_6)$cycloalkyl, and $-(C_{1-C_6})$alkoxy;

each and every $R^3$ and $R^4$ is independently selected from the group consisting of hydrogen, methyl, ethyl, n-propyl, or i-propyl;

diastereomeric and optical isomers thereof; and pharmaceutically acceptable salts thereof.

In another aspect, this invention relates to compounds of formula I wherein

Ar is phenyl, naphthyl, benzoxazolonyl, indolyl, indolonyl, benzimidazolyl, or quinolyl;

A is O, S, $SO_2$, C=O, CHOH, or $CH_2$;

n is 0 or 1, wherein Ar and $Ar^1$ may be independently substituted with up to three substituents independently selected from the group consisting of fluoro, chloro, cyano, $—NR^1R^2$, $-(C_1-C_6)$alkoxy, —COOR, $—CONR^1R^2$, and $-(C_1-C_6)$alkyl and the pharmaceutically acceptable salts thereof.

In another aspect, this invention relates to compounds of formula I wherein

A is O or S;

n is 1;

Ar is phenyl or substituted phenyl, and the pharmaceutically acceptable salts thereof.

In another aspect, this invention relates to compounds of formula I wherein

A is $CH_2$;

n is 0;

Ar is benzoxazolonyl or substituted benzoxazolonyl; and the pharmaceutically acceptable salts thereof.

In another aspect, this invention relates to compounds of formula I wherein

A is $CH_2$;

n is 0;

Ar is indolyl or substituted indolyl; and the pharmaceutically acceptable salts thereof.

In another aspect, this invention relates to compounds of formula I wherein

A is C=O or CHOH;

n is 0 or 1;

Ar is phenyl or substituted phenyl; and the pharmaceutically acceptable salts thereof.

In another aspect, this invention relates to compounds of formula I wherein

A is O;

Ar is fluorophenyl, difluorophenyl or cyanophenyl;

$Ar^1$ is chloropyridinyl; and the pharmaceutically acceptable salts thereof.

In another aspect, this invention relates to compounds of formula I wherein

A is O;

Ar is fluorophenyl, difluorophenyl or cyanophenyl;

$Ar^1$ is fluoropyrimidinyl; and the pharmaceutically acceptable salts thereof.

In another aspect, this invention relates to compounds of formula I wherein

A is O;
Ar is fluorophenyl, difluorophenyl or cyanophenyl;
$Ar^1$ is fluorophenyl; and the pharmaceutically acceptable salts thereof.

In another aspect, this invention relates to compounds of formula I wherein $Ar_1$ is 5-chloro-pyridin-2-yl; and the pharmaceutically acceptable salts thereof.

In another aspect, this invention comprises a compounds of formula I wherein $Ar^1$ is 5-fluoro-pyrimidin-2-yl; and the pharmaceutically acceptable salts thereof.

In a preferred aspect of the invention, A is O.
In another aspect of the invention, A is S, SO, or $S_2$.
In another aspect of the invention, A is C=O or CHOH.
In another preferred aspect of the invention, A is $CH_2$.
In another preferred aspect of the invention, Ar is phenyl or substituted phenyl.
In another preferred aspect of the invention, Ar is naphthyl or substituted naphthyl.
In another preferred aspect of the invention, Ar is benzoxazolonyl or substituted benzoxazolonyl.
In another preferred aspect of the invention, Ar is indolyl or substituted indolyl.
In another preferred aspect of the invention, Ar is indolonyl or substituted indolonyl.
In another preferred aspect of the invention, Ar is benzimidazolyl or substituted benzimidazolyl.
In another preferred aspect of the invention, Ar is quinolyl or substituted quinolyl.
In another preferred aspect of the invention, $Ar^1$ is phenyl or substituted phenyl.
In another preferred aspect of the invention, $Ar^1$ is pyridinyl or substituted pyridinyl.
In another preferred aspect of the invention, $Ar^1$ is pyridazinyl or substituted pyridazinyl.
In another preferred aspect of the invention, $Ar^1$ is pyrimidinyl or substituted pyrimidinyl.
In another preferred aspect of the invention, $Ar^1$ is pyrazinyl or substituted pyrazinyl.

Preferred compounds of the invention are:

(7R,9aS)-7-(4-fluorophenoxy)methyl-2-(5-chloro-pyridin-2-yl)-2,3,4,6,7,8,9,9a-octahydro-1H-pyrido[1,2-a]pyrazine;

(7R,9aS)-7-(3,5-difluorophenoxy)methyl-2-(5-chloro-pyridin-2-yl)-2,3,4,6,7,8,9,9a-octahydro-1H-pyrido[1,2-a]pyrazine;

3-[(7R,9aS)-2-(5-chloro-pyridin-2-yl)-2,3,4,6,7,8,9,9a-octahydro-1H-pyrido[1,2-a]pyrazin-7-ylmethyl]-3H-benzooxazol-2-one;

3-[(7R,9aS)-2-(5-fluoro-pyrimidin-2-yl)-2,3,4,6,7,8,9,9a-octahydro-1H-pyrido[1,2-a]pyrazin-7-ylmethyl]-3H-benzoxazol-2-one;

(7R,9aS)-7-(4-fluorophenoxy)methyl-2-(5-fluoro-pyrimidin-2-yl)-2,3,4,6,7,8,9,9a-octahydro-1H-pyrido[1,2-a]pyrazine;

(7R,9aS)-7-(3,5-difluorophenoxy)methyl-2-(5-fluoro-pyrimidin-2-yl)-2,3,4,6,7,8,9,9a-octahydro-1H-pyrido[1,2-a]pyrazine;

(7R,9aS)-7-(3,4-difluorophenoxy)methyl-2-(5-fluoro-pyrimidin-2-yl)-2,3,4,6,7,8,9,9a-octahydro-1H-pyrido[1,2-a]pyrazine;

(7R,9aS)-7-(3-cyanophenoxy)methyl-2-(5-fluoro-pyrimidin-2-yl)-2,3,4,6,7,8,9,9a-octahydro-1H-pyrido[1,2-a]pyrazine;

(7R,9aS)-7-(4-cyanophenoxy)methyl-2-(5-fluoro-pyrimidin-2-yl)-2,3,4,6,7,8,9,9a-octahydro-1H-pyrido[1,2-a]pyrazine;

(7R,9aS)-7-(4-iodophenoxy)methyl-2-(5-fluoro-pyrimidin-2-yl)-2,3,4,6,7,8,9,9a-octahydro-1H-pyrido[1,2-a]pyrazine;

(7R,9aS)-7-(4-fluorophenoxy)methyl-2-(4-fluorophenyl)-2,3,4,6,7,8,9,9a-octahydro-1H-pyrido[1,2-a]pyrazine;

(7 S,9aS)-7-(4-fluorophenoxy)methyl-2-(5-fluoro-pyrimidin-2-yl)-2,3,4,6,7,8,9,9a-octahydro-1H-pyrido[1,2-a]pyrazine;

(7S,9aS)-7-(2-carbomethoxy-4-fluorophenoxy)methyl-2-(5-fluoro-pyrimidin-2-yl)-2,3,4,6,7,8,9,9a-octahydro-1H-pyrido[1,2-a]pyrazine;

(7S,9aS)-7-(2-bromo-4-fluorophenoxy)methyl-2-(5-fluoro-pyrimidin-2-yl)-2,3,4,6,7,8,9,9a-octahydro-1H-pyrido[1,2-a]pyrazine;

(7S,9aS)-7-(4-fluoro-2-trifluoromethylphenoxy)methyl-2-(5-fluoro-pyrimidin-2-yl)-2,3,4,6,7,8,9,9a-octahydro-1H-pyrido[1,2-a]pyrazine;

(7S,9aS)-7-(3,5-difluorophenoxy)methyl-2-(5-chloro-pyridin-2-yl)-2,3,4,6,7,8,9,9a-octahydro-1H-pyrido[1,2-a]pyrazine;

(7S,9aS)-7-(4-fluorophenoxy)methyl-2-(5-chloro-pyridin-2-yl)-2,3,4,6,7,8,9,9a-octahydro-1H-pyrido[1,2-a]pyrazine;

(7S,9aS)-7-(4-fluoro-2-methylphenoxy)methyl-2-(5-fluoro-pyrimidin-2-yl)-2,3,4,6,7,8,9,9a-octahydro-1H-pyrido[1,2-a]pyrazine;

(7S,9aS)-7-(2,4-difluorophenoxy)methyl-2-(5-fluoro-pyrimidin-2-yl)-2,3,4,6,7,8,9,9a-octahydro-1H-pyrido[1,2-a]pyrazine;

(7S,9aS)-7-(3-methyl-phenoxy)methyl-2-(5-fluoropyrimidin-2-yl)-2,3,4,6,7,8,9,9a-octahydro-1H-pyrido[1,2-a]pyrazine;

(7S,9aS)-7-(3,4-difluoro-phenoxy)methyl-2-(5-fluoropyrimidin-2-yl)-2,3,4,6,7,8,9,9a-octahydro-1H-pyrido[1,2-a]pyrazine;

(7S,9aS)-7-(3,5-difluoro-phenoxy)methyl-2-(5-fluoropyrimidin-2-yl)-2,3,4,6,7,8,9,9a-octahydro-1H-pyrido[1,2-a]pyrazine;

(7S,9aS)-7-(3-cyano-phenoxy)methyl-2-(5-fluoropyrimidin-2-yl)-2,3,4,6,7,8,9,9a-octahydro-1H-pyrido[1,2-a]pyrazine;

(7S,9aS)-7-(3-trifluoromethyl-phenoxy)methyl-2-(5-fluoropyrimidin-2-yl)-2,3,4,6,7,8,9,9a-octahydro-1H-pyrido[1,2-a]pyrazine;

(7S,9aS)-7-(4-trifluoromethyl-phenoxy)methyl-2-(5-fluoropyrimidin-2-yl)-2,3,4,6,7,8,9,9a-octahydro-1H-pyrido[1,2-a]pyrazine;

(7S,9aS)-7-(3-trifluoromethoxy-phenoxy)methyl-2-(5-fluoropyrimidin-2-yl)-2,3,4,6,7,8,9,9a-octahydro-1H-pyrido[1,2-a]pyrazine;

(7S,9aS)-7-(3-methoxy-phenoxy)methyl-2-(5-fluoropyrimidin-2-yl)-2,3,4,6,7,8,9,9a-octahydro-1H-pyrido[1,2-a]pyrazine;

(7S,9aS)-7-(4-methoxy-phenoxy)methyl-2-(5-fluoropyrimidin-2-yl)-2,3,4,6,7,8,9,9a-octahydro-1H-pyrido[1,2-a]pyrazine;

and pharmaceutically acceptable salts thereof.

This invention also relates to the pharmaceutically acceptable acid addition salts of compounds of the formula I. The compounds of formula I are basic in nature and are capable of forming a wide variety of salts with various inorganic and organic acids. The acids that may be used to prepare pharmaceutically acceptable acid addition salts of those compounds of formula I are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, fumarate, gluconate, glucaronate, saccharate, formate, benzoate, glutamate, methanesulfonate, ethanesulfonate, benzenesulfonate, and p-toluenesulfonate.

The term "one or more substituents", as used herein, includes from one to the maximum number of substituents possible based on the number of available bonding sites.

The chemist of ordinary skill will recognize that certain combinations of substituents may be chemically unstable and will avoid these combinations or alternatively protect sensitive groups with well known protecting groups.

The term "alkyl", as used herein, unless otherwise indicated, includes saturated monovalent hydrocarbon radicals having straight, branched or cyclic moieties or combinations thereof.

The term "alkoxy", as used herein, unless otherwise indicated, refers to radicals having the formula —O-alkyl, wherein "alkyl" is defined as above.

The compounds of formula I above contain chiral centers and therefore exist in different enantiomeric forms. This invention relates to all optical isomers and all other stereoisomers of compounds of the formula I and mixtures thereof.

The compounds in accordance with the present invention, being ligands for dopamine receptor subtypes, especially the dopamine $D_4$ receptor, within the body, are accordingly of use in the treatment, prevention or diagnosis of disorders of the dopamine system.

It is generally accepted knowlege that dopamine receptors are important for many functions in the animal body. For example, altered functions of these receptors participate in the genesis of psychosis, addiction, sleep, feeding, learning, memory, sexual behavior, and blood pressure.

This invention provides dopamine ligands that are of use in the treatment and/or prevention of disorders of the dopamine system, including schizophrenia, nausea, Parkinson's disease, tardive dyskinesias and extrapyramidal side-effects associated with treatment by conventional neuroleptic agents, neuroleptic malignant syndrome, and disorders of hypothalamic-pituitary function such as hyperprolactinaemia and amenorrhoea.

Upper gastrointestinal tract motility is believed to be under the control of the dopamine system. The compounds according to the present invention are of use in the prevention or treatment of gastrointestinal disorders, and the facilitation of gastric emptying.

Dependence-inducing agents such as cocaine and amphetamine have been shown to interact with the dopamine system. Compounds capable of counteracting this effect, including the compounds in accordance with the present invention, are accordingly of value in the prevention or reduction of dependence on a dependence-inducing agent.

Dopamine is known to be a peripheral vasodilator; for example, it has been shown to exert a dilatory effect on the renal vascular bed. This shows that the compounds of the present invention are beneficial in controlling vascular blood flow.

The localization of dopamine receptor mRNA in rat heart and large vessels has been noted. This suggests a role for dopamine receptor ligands in controlling cardiovascular function, either by affecting cardiac and smooth muscle contractility or by modulating the secretion of vasoactive substances. The compounds according to the present invention are of assistance in the prevention or treatment of such conditions as hypertension and congestive heart failure.

The presence of D4 receptor mRNA in rat retina has been noted (Cohen, et al. *Proc. Nat. Acad. Sci.*, 1992, 89, 12093), suggesting that dopamine and D4 receptors play a role in ocular function. The compounds of this invention may therefore be useful in the treatment of ocular disorders. Furthermore, D4 receptors influence melatonin biosynthesis in chick retina (Zawilska, Nowak, *Neuroscience Lett.*, 1994, 166, 203), and since melatonin has been used for the treatment of sleep disorders, the compounds of this invention may be useful for the treatment of sleep disorders as well.

This invention also relates to a pharmaceutical composition for treating or preventing a disease or condition, the treatment or prevention of which can be effected or facilitated by altering dopamine mediated neurotransmission in a mammal, comprising a dopaminergic effective amount of a compound according to claim 1 or a pharmaceutically acceptable salt thereof and a pharmaceutically acceptable carrier.

This invention also relates to a method of treating or preventing a disease or condition, the treatment or prevention of which can be effected or facilitated by altering dopamine mediated neurotransmission in a mammal, comprising administering to said mammal a dopaminergic effective amount of a compound according to claim 1 or a pharmaceutically acceptable salt thereof.

This invention also relates to a pharmaceutical composition for treating or preventing a disease or condition, the treatment or prevention of which can be effected or facilitated by altering dopamine mediated neurotransmission in a mammal, comprising a $D_4$ receptor binding effective amount of a compound according to claim 1 or a pharmaceutically acceptable salt thereof and a pharmaceutically acceptable carrier.

This invention also relates to a method of treating or preventing a disease or condition, the treatment or prevention of which can be effected or facilitated by altering dopamine mediated neurotransmission in a mammal, comprising administering to said mammal a $D_4$ receptor binding effective amount of a compound according to claim 1 or a pharmaceutically acceptable salt thereof.

This invention also relates to a pharmaceutical composition for treating or preventing a disease or condition, the treatment or prevention of which can be effected or facilitated by altering dopamine mediated neurotransmission in a mammal, comprising administering to said mammal an amount of a compound according to claim 1 or a pharmaceutically acceptable salt thereof that is effective in treating or preventing such condition.

This invention also relates to a method of treating or preventing a disease or condition, the treatment or prevention of which can be effected or facilitated by altering dopamine mediated neurotransmission in a mammal, comprising administering to said mammal an amount of a compound according to claim 1 or a pharmaceutically acceptable salt thereof that is effective in treating or preventing such condition.

This invention also relates to the use of a compound of formula I for the treatment, prevention, or diagnosis of psychotic disorders such as affective psychosis, schizophrenia, and schizoaffective disorders.

This invention also relates to the use of a compound of formula I for the treatment, prevention, or diagnosis of movement disorders such as extrapyramidal side effects from neuroleptic agents, neuroleptic malignant syndrome, tardive dyskinesia, or Gilles De La Tourette's syndrome.

This invention also relates to the use of a compound of formula I for the treatment, prevention, or diagnosis of movement disorders such as Parkinson's disease or Huntington's disease.

This invention also relates to the use of a compound of formula I for the treatment, prevention, or diagnosis of gastrointestinal disorders such as gastric acid secretion.

This invention also relates to the use of a compound of formula I for the treatment, prevention, or diagnosis of gastrointestinal disorders such as emesis.

This invention also relates to the use of a compound of formula I for the treatment, prevention, or diagnosis of chemical abuse, chemical dependencies or substance abuse.

This invention also relates to the use of a compound of formula I for the treatment, prevention, or diagnosis of vascular and cardiovascular disorders such as congestive heart failure and hypertension.

This invention also relates to the use of a compound of formula I for the treatment, prevention, or diagnosis of ocular disorders.

This invention also relates to the use of a compound of formula I for the treatment, prevention, or diagnosis of sleep disorders.

The term "dopaminergic effective amount", as used herein, refers to an amount of a compound sufficient to inhibit the binding of dopamine to a dopamine receptor with the effect of altering (i.e. increasing or decreasing) dopamine mediated neurotransmission.

The term "$D_4$ receptor binding effective amount", as used herein, refers to an amount of a compound sufficient to inhibit dopamine binding to a dopamine $D_4$ receptor with the effect of altering (i.e. increasing or decreasing) dopamine mediated neurotransmission.

In another aspect this invention provides intermediate compounds of the formula

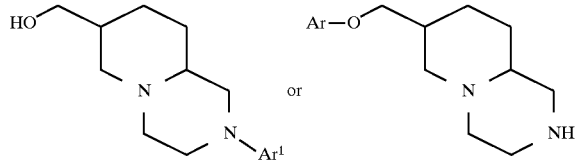

wherein $Ar^1$ is 5-fluoropyrimidin-2-yl or 5-chloropyridin-2-yl and Ar is 4-fluorophenyl and optical isomers and stereoisomers thereof useful in the preparation of compounds of formula I.

DETAILED DESCRIPTION OF THE INVENTION

The compounds of formula I are readily prepared by a number of methods which are summarized in Schemes I–X.

While the overall routes and various intermediates in Scheme I–X are novel, the individual chemical steps are generally analogous to known chemical transformations. Generally suitable conditions are found in the prior art. Isolation and purification of the products is accomplished by standard procedures which are known to a chemist of ordinary skill. Particularly well-suited conditions are exemplified below.

Intermediates which are known from the prior art are listed in Table I. Enantiomers of some intermediates may be prepared using standard methods which are well known to a chemist of ordinary skill.

As used hereinafter, the expression "reaction inert solvent" refers to a solvent system in which the components do not interact with starting materials, reagents, intermediates of products in a manner which adversely affects the yield of the desired product.

During any of the following synthetic sequences it may be necessary and/or desirable to protect sensitive or reactive groups on any of the molecules concerned. This may be achieved by means of conventional protecting groups, such as those described in T. W. Greene, *Protective Groups in Organic Chemistry*, John Wiley & Sons, 1981; and T. W. Greene and P. G. M. Wuts, *Protective Groups in Organic Chemistry*, John Wiley & Sons, 1991.

The expression "nitrogen protecting group" as used hereinafter means a moiety which when coupled with a basic nitrogen will remain inert while other reactions are carried out. The nitrogen protecting group may then be removed under mild conditions yielding the free amino group. This invention contemplates two types of nitrogen protecting groups: those which may be removed by treatment with strong acid and those which may be removed by hydrogenation.

Examples of nitrogen protecting groups removed by strong acid are tert-butoxycarbonyl, methoxycarbonyl, ethoxycarbonyl, trimethylsilylethoxycarbonyl, 1-adamantyloxycarbonyl, vinyloxycarbonyl, diphenylmethoxycarbonyl, trityl, acetyl and benzoyl. The group preferred is tert-butoxycarbonyl (BOC).

Examples of nitrogen protecting groups removed by hydrogenation are benzyloxycarbonyl, 9-fluorenylmethyloxycarbonyl, 2-phenylethyloxycarbonyl, benzyl, p-methoxybenzyloxycarbonyl, and p-nitrobenzyloxycarbonyl. The preferred group is benzyloxycarbonyl.

Removal of the BOC protecting group from compounds II or V (Scheme I) may be effected under anhydrous conditions with HCl gas in a reaction inert solvent such as ethyl acetate, ether or chloroform. Alternatively, the BOC group may be removed in aqueous solution by a strong acid, for example, hydrocholoric acid or trifluoroacetic acid. The temperature of these reactions are not critical, and it has been found convenient to conduct the reaction at ambient temperature.

Amines of formula III or VI may be coupled with an activated form of $Ar^1$ (Scheme I) to form compounds IV or I, respectively, using methods which are directly analogous to those described by Bright and Desai (U.S. Pat. No. 5,122,525). The term "activated form of $Ar^1$" means a chemical derivative of

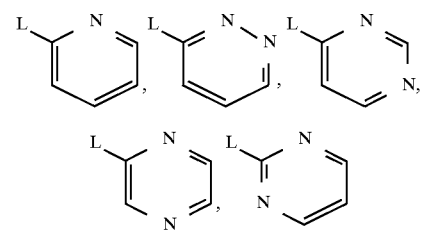

wherein L is a leaving group. The term "leaving group" (L) refers to groups which may be replaced by other groups under suitable conditions, and include, for example, halogen, lower-alkylsulfonyl and arylsulfonyl. Activated forms of $Ar^1$ may also be derivatives of benzene bearing an electron withdrawing group (EWG) and a leaving group (L) in the ortho- or para- positions relative to one other:

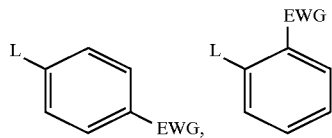

Where the activated form of Ar¹ is a derivative of benzene, halogens are the preferred leaving groups, especially fluoro, and nitro or cyano are examples of preferred electron withdrawing groups. The reaction is conveniently carried out in reaction inert solvents such as water, lower alcohols, or dimethyl sulfoxide and temperatures from about 30° C. to about 170° C. The presence of an acid acceptor such as trialkyl amine or alkali carbonate may be useful.

Compounds IV or I may also be prepared by coupling compounds of formula III or VI, respectively, with activated forms of Ar¹ in which the leaving group (L) is lower alkoxy or aryloxy according to the method reported by Wyberg et al. (J. Org. Chem. 1993, 58, 5101). Amines III or VI are first converted to their alkali amide by the action of a strong hydrogen atom acceptor such as butyllithium in a reaction inert solvent, preferably a relatively polar ether solvent such as tetrahydrofuran, 1,4-dioxane or 1,2-dimethoxyethane followed by addition of an activated form of Ar¹ in which the leaving group (L) is lower alkoxy or aryloxy. Formation of the alkali amide in the first step is conducted at a temperature of about −70° C. to about 10° C. and the addition of the activated form of Ar¹ in the second step is conveniently carried out at a temperature of about 20° C. to about 100° C.

A useful method for coupling alcohols of formula II or IV with phenols of formula ArOH to produce compounds V or I, respectively involves conversion of the alcohol moiety of compounds II or IV into a leaving group such as lower-alkylsulfonyl ester or arylsulfonyl ester as the first step of a two-step process. The alkyl- or arylsulfonyl ester is prepared by the reaction of an alkyl- or arylsulfonyl chloride with alcohol II or IV in the presence of a trialkyl amine in a reaction inert solvent (e.g. methylene chloride) at a temperature from about −10° C. to about 60° C. In a second step, ArOH is converted into the alkali metal salt (ArOM) with a suitable hydrogen atom acceptor, preferably an alkali metal hydride, and the alkali salt ArOM is then reacted with the alkyl- or arylsulfonyl derivative in a polar reaction inert solvent such as dimethyl formamide (DMF) or dimethylsulfoxide (DMSO) at a temperature from about 0° C. to about 150° C. By substituting aromatic heterocycles with moderately acidic NH substituents such as 5-fluoroindole or 5-chloro-2-methylbenzoimidazole for a phenol ArOH in the second step, this procedure may be used to prepare examples of compound I wherein Ar is 5-fluoroindol-1-yl or 5-chloro-2-methylbenzoimidazol-1-yl. Furthermore, indoles such as 5-fluoroindole may be used with an alkyl magnesium halide such as ethyl magnesium bromide as the hydrogen atom acceptor in the second step to prepare examples of compound I wherein Ar is 5-fluoroindol-3-yl (Scheme X).

Compounds of the formula V or I may also be prepared by combining approximately equimolar quantities of alcohols II or IV, a phenol ArOH or a thiol ArSH, triarylphosphine (e.g. triphenylphosphine (Ph₃P)), and dialkyl azodicarboxylate (e.g. diethyl azodicarboxylate (DEAD)) in a relatively polar ether solvent such as tetrahydrofuran (THF), 1,4-dioxane or 1,2-dimethoxyethane at a temperature from about 0° C. to about 100° C.

Examples of compound I wherein A is CHOH and n is 0 may be prepared by converting the alcohol functionality of compound IV into an aldehyde of formula VII by the reaction of a mild oxidant such as dimethylsulfoxide/oxalyl chloride in a reaction inert solvent such as methylene chloride at a temperature from about −80° C. to about −40° C. (Scheme II). In a second step, aldehyde VII may then be treated with an aryl metal derivative such as a phenyl magnesium halide in a reaction inert solvent, preferably an ether, to produce compound I wherein A is CHOH and n is 0. Compounds of formula I where A is CHOH may be converted into compounds of formula I where A is C=O by the action of an oxidizing agent. Many commonly known oxidants are suitable for the conversion of I (A is CHOH) into I (A is C=O), and one which is preferred is the combination of dimethylsulfoxide and oxalyl chloride in a reaction inert solvent such as methylene chloride at a temperature from about −80° C. to about −40° C.

Examples of compound I where A is C=O and n is 1 or where A is CHOH and n is 1 may be prepared by converting the alcohol functionality of compound IV into a nitrile of formula VIII by conversion of the alcohol moiety of compounds IV into a leaving group such as lower-alkylsulfonyl ester or arylsulfonyl ester as a first step (Scheme III). The alkyl- or arylsulfonyl ester is prepared by the reaction of an alkyl- or arylsulfonyl chloride with alcohol IV in the presence of a trialkyl amine in a reaction inert solvent (e.g. methylene chloride) at a temperature from about −10° C. to about 60° C. In a second step, the alkyl- or arylsulfonyl ester is treated with an alkali cyanide in polar reaction inert solvent such as dimethyl formamide (DMF) or dimethylsulfoxide (DMSO) at a temperature from about 0° C. to about 150° C. to give nitrile VIII.

Nitrile VIII may be treated with an aryl metal derivative such as a phenyl magnesium halide and cuprous halide in a reaction inert solvent, preferably an ether, at a temperature from about 0° C. to about 150° C. followed by hydrolysis in an aqueous solution of a strong acid such as sulfuric acid at a temperature from about 20° C. to about 120° C. to give compounds I where A is C=O and n is 1 (Scheme III).

Nitrile VIII may be treated with a hydride reducing agent, such as diisobutylaluminum hydride, to produce aldehyde IX (Scheme III). Aldehyde IX may then be treated with an aryl metal such as a phenyl magnesium halide in a reaction inert solvent, preferably an ether, at a temperature from about −70° C. to about 50° C. to give compound I where A is CHOH and n is 1 (Scheme III).

Compounds of formula I where A is O and n is 0 may be prepared in a several step process starting with the compound X which is synthesized according the method described by Compernolle et al. (J. Org. Chem., 1991, 56, 5192) (Scheme IV). Compound X may be converted into a compound of formula XI by using a method analogous to that described by Bright and Desai (U.S. Pat. No. 5,122,525) by combining compound X with an activated form of Ar¹ such as 2-chloropyrimidine, alkali carbonate and a reaction inert solvent such as water at a temperature from about 25° C. to about 150° C. Removal of the ethylene ketal protecting group is accomplished in another step by standard conditions, preferably with a strong acid in a solvent such as water, to produce ketone XII. Reduction of ketone XII to alcohol XIII may be accomplished in another step by reaction with a hydride reducing agent of aluminum or boron in a reaction inert solvent, many suitable examples of which are known in the literature. Sodium borohydride, either alone or supported on a reaction inert substance such as alumina in a polar, protic solvent such as a lower alcohol is a preferred example. Combining approximately equimolar quantities of alcohol XIII and a phenol ArOH, triarylphosphine (e.g. triphenylphosphine (Ph₃P)), and dialkyl azodicarboxylate (e.g. diethyl azodicarboxylate (DEAD)) in a relatively polar ether solvent such as tetrahydrofuran (THF), 1,4-dioxane or 1,2-dimethoxyethane at a temperature from about 0° C. to about 100° C. is a useful method for preparing compounds of formula I where A is O and n is 0 (Scheme IV).

Some examples of compounds I may be converted into other examples of compounds I through reactions of their functional groups.

For example, compound I where $Ar^1$ is 5-fluoro-2-pyridinyl may be prepared by subjecting compound I where $Ar^1$ is 5-bromo-2-pyridinyl to conditions sufficient to exchange bromine for a metal atom, such as butyllithium, in a reaction inert solvent, preferably an ether such as THF, at a temperature from about −120° C. to about 0° C., followed by addition of an electrophilic fluorine source such as N-fluorobis(benzenesulfonamide) (Scheme V).

Compounds I where Ar or $Ar^1$ has a chloro, bromo or iodo substituent may be converted into the analogous compounds I wherein the chloro, bromo, or iodo atom has been exchanged for an isotope of hydrogen. For example, a mixture of compound I where $Ar^1$ is 6-chloro-3-pyridazinyl and a noble metal catalyst, such as palladium on carbon, in a lower alcohol solvent under one to ten atmospheres of hydrogen gas produces compound I where $Ar^1$ is 3-pyridazinyl (Scheme VI). Similar treatment of compound I where $Ar^1$ is 2-chloro-4-pyrimidinyl gives compound I where $Ar^1$ is 4-pyrimidinyl.

Compounds I where A is S may be converted into compounds I where A is $SO_2$ by the reaction with an oxidizing agent, such as m-chloroperoxybenzoic acid, in reaction inert solvent such as methylene chloride at a temperature from about −10° C. to about 50° C. (Scheme VII).

Compounds I where $Ar^1$ has an amino substituent may be converted into the analogous compounds I where the amino substituent has been replaced by hydrido. For example, a mixture of compound I where $Ar^1$ is 4-aminophenyl with isoamyl nitrite and THF at a temperature from about 25° C. to about 125° C. gives compound I where $Ar^1$ is phenyl (Scheme VIII). Similar treatment of compound I where $Ar^1$ is 2-amino-4-fluorophenyl gives compounds I where $Ar^1$ is 4-fluorophenyl (Scheme IX).

TABLE 1

Intermediates found in prior art.

| Formula | R | Isomer | Reference |
|---|---|---|---|
| II | BOC | (7R,9aS) | PC WO 93/25552 |
| II | BOC | (7S,9aS) | PC WO 93/25552 |
| III | H | (7SR,9aSR) | U.S. Pat. No. 5,122,525 |
| III | H | (7RS,9aSR) | U.S. Pat. No. 5,326,874 |
| IV | 2-methylpyridinyl | (7SR,9aSR) | U.S. Pat. No. 5,122,525 |
| IV | 2-methylpyrimidinyl | (7SR,9aSR) | U.S. Pat. No. 5,122,525 |
| IV |  | (7S,9aS) | U.S. Pat. No. 5,122,525 |
| IV |  | (7S,9aS) | WO 92/13858 |
| IV |  | (7R,9aR) | WO 92/13858 |
| IV | benzisoxazolyl-methyl | (7SR,9aSR) | WO 93/25552 |
| IV |  | (7S,9aS) | WO 93/25552 |
| IV |  | (7R,9aS) | WO 93/25552 |

Scheme I.

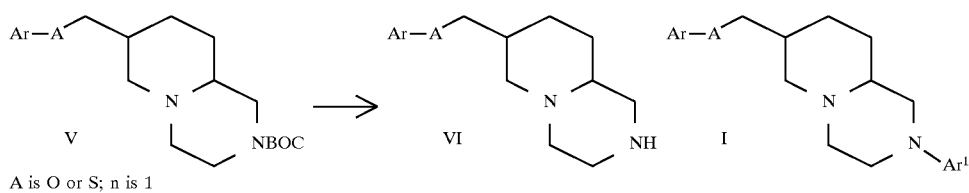
A is O or S; n is 1
-continued
Scheme I.
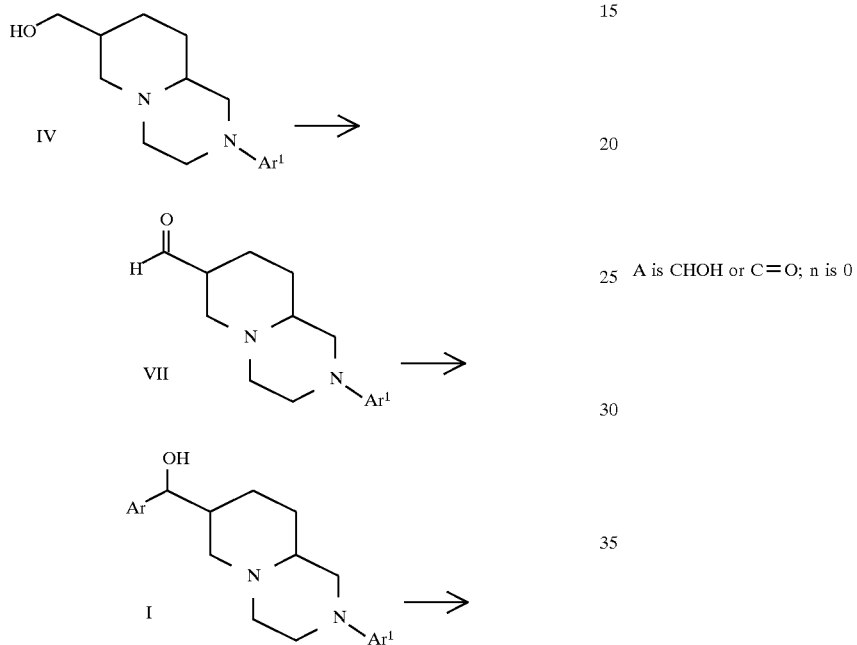
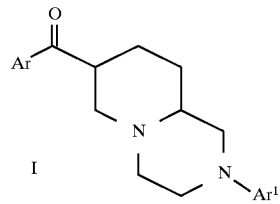
A is CHOH or C=O; n is 0
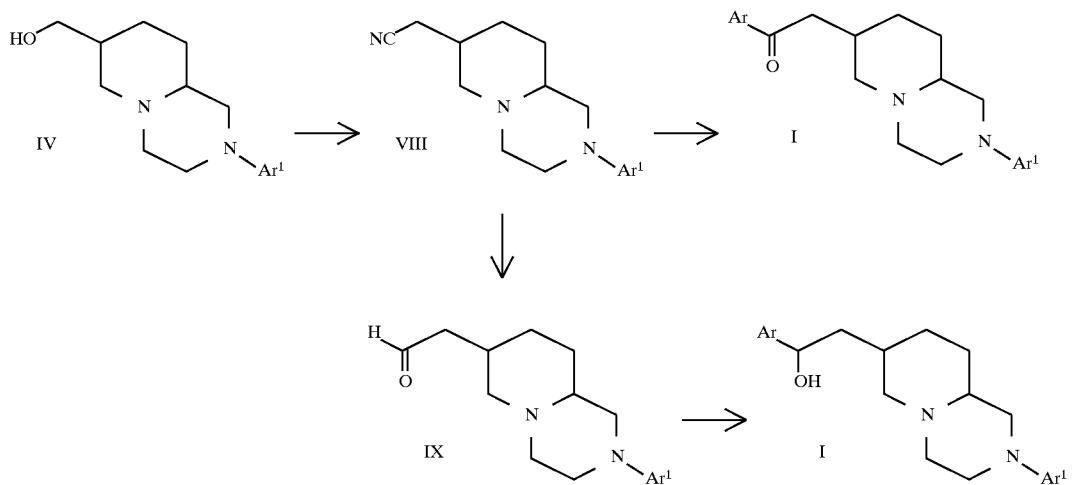
A is CHOH or C=O; n is 1

Scheme IV.
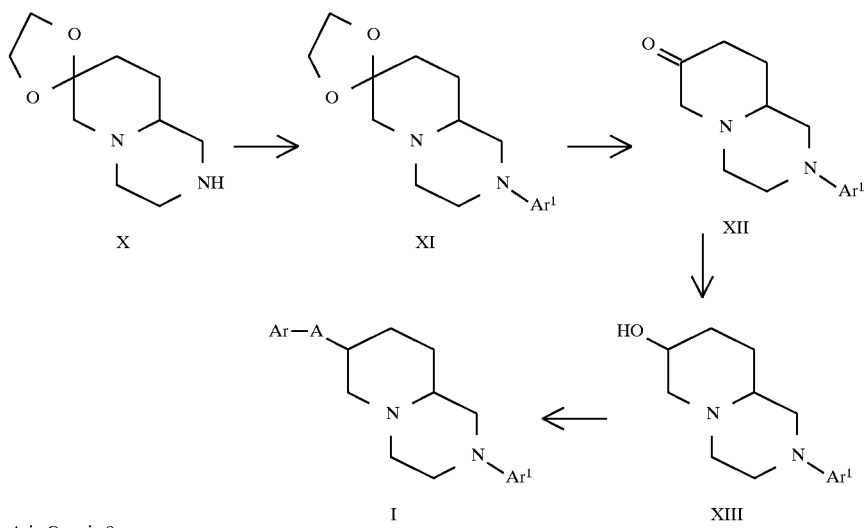
A is O; n is 0
Scheme V.
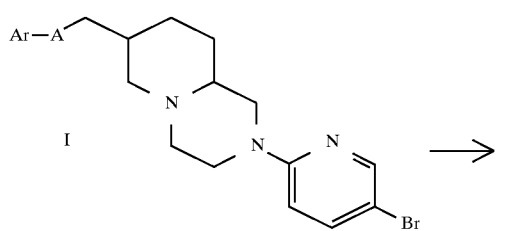
Scheme VI.
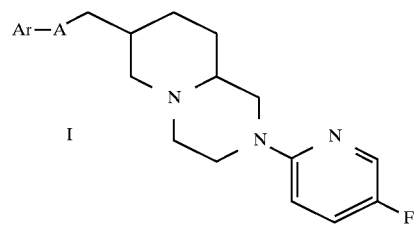
-continued
Scheme VI.
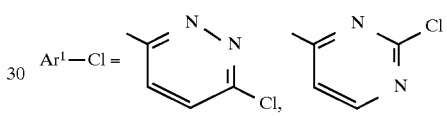
Scheme VII.
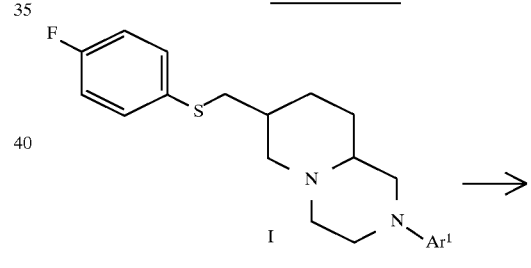
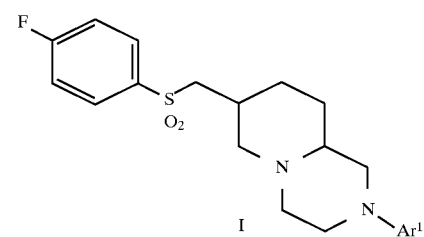
Scheme VIII.
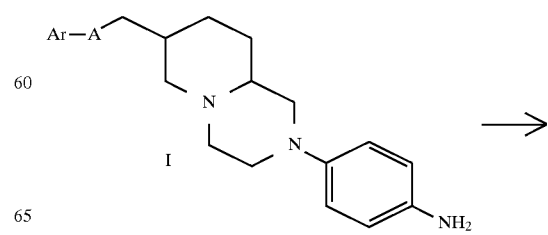

-continued
Scheme VIII.

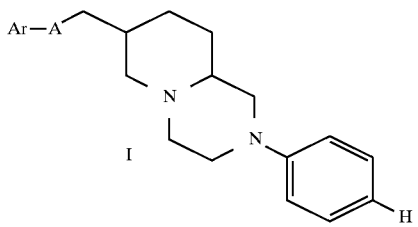

Scheme IX.

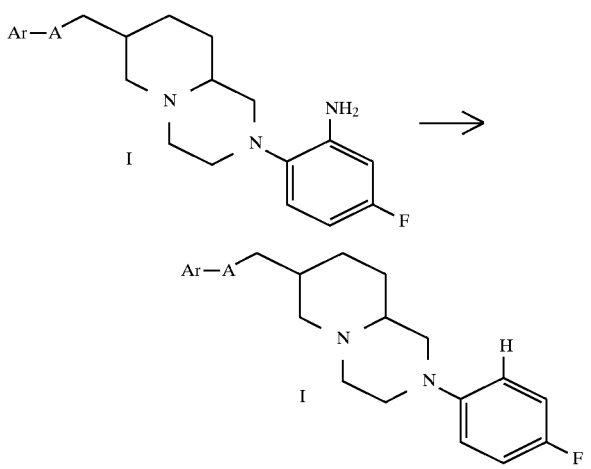

Scheme X.

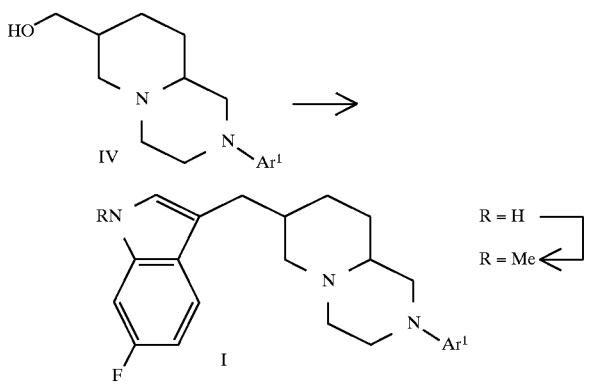

A is CH₂; n is 0

The novel compounds of the formula I and the pharmaceutically acceptable salts thereof (herein "the therapeutic compounds of this invention") are useful as dopaminergic agents, i.e., they possess the ability to alter dopamine mediated neurotransmission in mammals, including humans. They are therefore able to function as therapeutic agents in the treatment of a variety of conditions in mammals, the treatment or prevention of which can be effected or facilitated by an increase or decrease in dopamine mediated neurotransmission.

The compounds of the formula I that are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

The therapeutic compounds of this invention can be administered orally, transdermally (e.g., through the use of a patch), parenterally or topically. Oral administration is preferred. In general, these compounds are most desirably administered in dosages ranging from about 0.1 mg up to about 1000 mg per day, or 1 mg to 1000 mg per day in some cases, although variations may occur depending on the weight and condition of the person being treated and the particular route of administration chosen. In some instances, dosage levels below the lower limit of the aforesaid range may be more than adequate, while in other cases still larger doses may be employed without causing any harmful side effect, provided that such larger doses are first divided into several small doses for administration throughout the day.

The therapeutic compounds of the invention may be administered alone or in combination with pharmaceutically acceptable carriers or diluents by either of the two routes previously indicated, and such administration may be carried out in single or multiple doses. More particularly, the novel therapeutic compounds of this invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, elixirs, syrups, and the like. Such carriers include solid diluents or fillers, sterile aqueous media and various non-toxic organic solvents, for example. Moreover, oral pharmaceutical compositions can be suitably sweetened and/or flavored.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered if necessary and the liquid diluent first rendered isotonic. These aqueous solutions are suitable for intravenous injection purposes. The oily solutions are suitable for intra-articular, intramuscular and subcutaneous injection purposes. The preparation of all these solutions under sterile conditions is readily accomplished by standard pharmaceutical techniques well known to those skilled in the art.

Additionally, it is also possible to administer the compounds of the present invention topically when treating inflammatory conditions of the skin and this may preferably be done by way of creams, jellies, gels, pastes, ointments and the like, in accordance with standard pharmaceutical practice.

Dopaminergic activity is related to the ability of compounds to bind to mammalian dopamine receptors, and the relative ability of compounds of this invention to inhibit [$^3$H]-spiperone binding to human dopamine $D_4$ receptor subtypes expressed in clonal cell lines was measured using the following procedure.

The determination of $D_4$ receptor binding ability has been described by Van Tol et al., Nature (London), 1991, 350, 610. Clonal cell lines expressing the human dopamine $D_4$ receptor are harvested and homogenized (polytron) in a 50 mM Tris:HCl (pH 7.4 at 4° C.) buffer containing 5 mM EDTA, 1.5 mM calcium chloride ($CaCl_2$), 5 mM magnesium chloride ($MgCl_2$), 5mM potassium chloride (KCl) and 120 mM sodium chloride (NaCl). The homogenates are centrifugated for 10–15 min. at 48,000 g, and the resulting pellets resuspended in a buffer at a concentration of 150–250 mg/ml. For saturation experiments, 0.75 ml aliquots of tissue homogenate are incubated in triplicate with increasing concentrations of [$^3$H] spiperone (70.3 Ci/mmol; 10–3000 pM final concentration) for 30–120 minutes at 22° C. in a total volume of 1 ml. For competition binding experiments, assays are initiated by the addition of 0.75 ml of membrane and incubated in duplicate with the indicated concentrations of competing ligands ($10^{-14}$–$10^{-3}$M) and/or [$^3$H]spiperone (100–300 pM) for 60–120 min at 22° C. Assays are terminated by rapid filtration through a Brandell cell harvester and the filters subsequently monitored for tritium as described by Sunahara, R. K. et. al., Nature (London), 1990, 346, 76. For all experiments, specific [$^3$H]spiperone binding is defined as that inhibited by 1–10 mM (+)-butaclamol. Binding data are analyzed by non-linear least square curve-fitting.

The following Examples are provided solely for the purposes of illustration and do not limit the invention which is defined by the claims.

EXAMPLE 1

(7R,9aS)-7-(Phenoxy)methyl-(2-pyrimidin-2-yl)-2,3,4,6,7,8,9,9a-octahydro-1H-pyrido[1,2-a]pyrazine

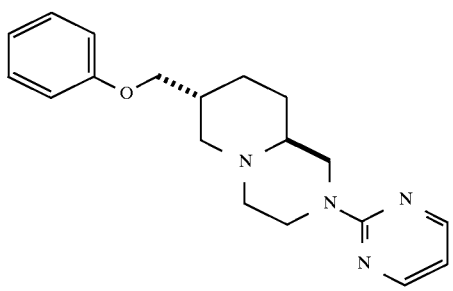

A solution of 0.385 g (1.55 mmol) of (7R,9aS)-7-hydroxymethyl-2-(pyrimidin-2-yl)-2,3,4,6,7,8,9,9a-octahydro-1H-pyrido[1,2-a]pyrazine (Preparation 4), 0.220 g (2.34 mmol) of phenol, and 0.488 g (1.86 mmol) of triphenylphosphine in 30 mL of dry THF was treated with 0.324 g (1.86 mmol) of diethyl azodicarboxylate, and the mixture stirred at 23° C. for 16 h. The solvent was evaporated, the residue dissolved in ethyl ether and treated with HCl(g) in ether. The precipitate was collected on a Büchner funnel, and washed with 1:1 ether:ethyl acetate three times. The solid was dissolved in water, basified with 1M NaOH and extracted with chloroform. The organic layer was washed with 1M NaOH (2×) and water (1×), dried (magnesium sulfate), filtered and evaporated to give 0.310 g of (7R,9aS)-7-phenoxymethyl-2,3,4,6,7,8,9,9a-octahydro-2-pyrimidin-2-yl-1H-pyrido[1,2-a]pyrazine. mp (.HCl) 203°–205° C. $^{13}$C NMR (base, $CDCl_3$): δ 27.0, 29.0, 36.4, 43.6, 49.1, 54.9, 58.8, 60.8, 70.9, 109.8, 114.5, 120.6, 129.4, 157.7, 159.0, 161.5. HRMS calcd for $C_{19}H_{24}N_4O$: 324.195. Found: 324.194.

EXAMPLE 2

7-(Substituted-phenoxy)methyl-2-(pyrimidin-2-yl)-2,3,4,6,7,8,9,9a-octahydro-1H-pyrido[1,2-a]pyrazines

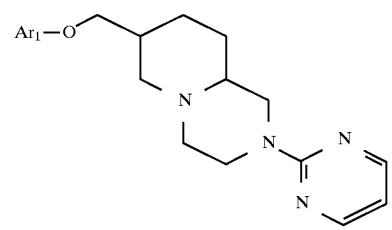

Compounds of the above formula were prepared from isomers of 7-hydroxymethyl-(2-pyrimidin-2-yl)-2,3,4,6,7,8,9,9a-octahydro-1H-pyrido[1,2-a]pyrazine (Preparation 4, U.S. Pat. No. 5,122,525, and WO 92/13858) according to Example 1, substituting the appropriate phenol. Purification was generally accomplished by flash silica gel chromatography using mixtures of ethyl acetate and hexane or mixture of chloroform and methanol as the eluting solvent. The stereo-chemical configuration, 7-(optionally substituted phenoxy)methyl substituent, melting point of the monohydrochloride salt, and high resolution mass spectral data are shown.

Example 2a (7SR,9aSR)-7-Phenoxymethyl; mp 119°–122° C.; Anal calcd for $C_{19}H_{24}N_4O$.HCl: C, 63.23; H, 6.98; N, 15.53. Found: C, 63.19; H, 7.30; N, 15.66.

Example 2b (7R,9aR)-7-Phenoxymethyl; mp 226°–231° C.; HRMS calcd for $C_{19}H_{24}N_4O$: 324.1945, found: 324.1920.

Example 2c (7RS,9aSR)-7-(4-Fluorophenoxy)methyl; mp 263°–266° C.; HRMS calcd for $C_{19}H_{23}FN_4O$: 342.1851, found: 342.1796.

Example 2d (7RS,9aSR)-7-((2,4-Difluoro)phenoxymethyl); mp 242.5°–244° C.; HRMS calcd for $C_{19}H_{22}F_2N_4O$: 360.1762, found: 360.1775.

Example 2e (7RS,9aSR)-7-(3,4-Difluorophenoxy)methyl; mp 239°–240° C.; HRMS calc for $C_{19}H_{22}F_2N_4O$: 360.1762, found: 360.1745.

Example 2f (7RS,9aSR)-7-((3-Fluoro)phenoxymethyl); mp 242°–243° C.; HRMS calc for $C_{19}H_{23}FN_4O$: 342.1856, found: 342.1851.

Example 2g (7RS,9aSR)-7-(2-Naphthoxymethyl); mp 143°–145° C.; HRMS calc for $C_{23}H_{26}N_4O$: 374.2107, found: 374.2097.

Example 2h (7RS,9aSR)-7-(1-Naphthoxymethyl); mp 243°–245° C.; HRMS calc for $C_{23}H_{26}N_4O$: 374.2107, found: 374.2098.

Example 2i (7RS,9aSR)-7-(4-Fluoro-3-methylphenoxy)methyl; mp 232°–233° C.; HRMS calc for $C_{20}H_{25}FN_4O$: 356.2012, found: 356.1992.

Example 2j (7RS,9aSR)-7-((3-Carbomethoxy)phenoxymethyl); mp 194°–196° C.; HRMS calc for $C_{21}H_{26}N_4O_3$: 382.2005, found: 382.2010.

Example 2k (7RS,9aSR)-7-(5-Fluoroquinolin-8-yloxy)methyl; mp 218°–220° C.; HRMS calc for $C_{22}H_{25}FN_5O$ (MH+): 394.2043, found: 394.2059.

Example 2l (7RS,9aSR)-7-((2-Methoxy-5-(1-methyl)ethyl)phenoxy)methyl; mp 94°–99° C.; HRMS calcd for $C_{23}H_{32}N_4O_2$: 396.2518, found: 396.2504.

Example 2m (7RS,9aSR)-7-((2-Methoxy-3-(1-methyl)ethyl)phenoxy)methyl; mp 219°–221° C.; HRMS calcd for $C_{23}H_{32}N_4O_2$: 396.2518, found: 396.2522.

Example 2n (7RS,9aSR)-7-((2-Methoxy-4-acetyl)phenoxy)methyl; mp 224° C. (dec); HRMS calcd for $C_{22}H_{28}N_4O_3$: 396.215, found: 396.210.

Example 2o (7R,9aS)-7-(3-(1-Methyl)ethylphenoxy)methyl; mp 70°–120° C. (dec); HRMS calcd for $C_{22}H_{30}N_4O$: 366.2413, found: 366.2420.

Example 2p (7R,9aS)-7-((2-Methoxy)phenoxy)methyl; mp 213°–215° C.; HRMS calcd for $C_{20}H_{26}N_4O_2$: 354.2050, found: 354.2093.

Example 2q (7R,9aS)-7-((4-Acetamido)phenoxy)methyl; mp 192° C.; HRMS calcd for $C_{21}H_{27}N_5O_2$: 381.2159, found: 381.2120.

Example 2r (7R,9aS)-7-(4-(1,1-Dimethyl)ethyl-phenoxy)methyl; mp 237°–244° C. (dec); HRMS calcd for $C_{23}H_{32}N_4O$: 380.2576, found: 380.2674.

Example 2s (7R,9aS)-7-(3-(1,1-Dimethyl)ethyl-phenoxy)methyl; mp 229°–230° C.; HRMS calcd for $C_{23}H_{32}N_4O$: 380.2576, found: 380.2577.

Example 2t (7R,9aS)-7-(2-(1,1-Dimethyl)ethyl-phenoxy)methyl; mp 240°–241° C.; HRMS calcd for $C_{23}H_{32}N_4O$: 380.2576, found: 380.2580.

Example 2u (7R,9aS)-7-(4-Methoxy-phenoxy)methyl; mp 219°–222° C.; HRMS calcd for $C_{20}H_{26}N_4O_2$: 354.2050, found: 354.2063.

Example 2v (7R,9aS)-7-(3-Methoxy-phenoxy)methyl; mp 113°–115° C.; HRMS calcd for $C_{20}H_{26}N_4O_2$: 354.2056, found: 354.2041.

Example 2w (7R,9aS)-7-(3-Acetamido-phenoxy)methyl; mp 156°–158° C.; HRMS calcd for $C_{21}H_{27}N_5O_2$: 381.2165, found: 381.2160.

Example 2x (7R,9aS)-7-(2-Cyano-phenoxy)methyl; mp 250°–252° C.; HRMS calcd for $C_{20}H_{23}N_5O$: 349.1903, found: 349.1932.

Example 2y (7R,9aS)-7-(3-Cyano-phenoxy)methyl; mp 241.5°–243° C.; HRMS calcd for $C_{20}H_{23}N_5O$: 349.1903, found: 349.1897.

Example 2z (7R,9aS)-7-(3-Dimethylamino-phenoxy)methyl; mp 80°–82° C.; HRMS calcd for $C_{21}H_{29}N_5O$: 367.2372, found: 367.2357.

Example 2aa (7R,9aS)-7-(3,4-Difluoro-phenoxy)methyl; mp 252°–254° C.; HRMS calcd for $C_{19}H_{22}F_2N_4O$: 360.1762, found: 360.1763.

Example 2ab (7S,9aR)-7-(4-Fluoro-phenoxy)methyl; mp 281°–282° C.; HRMS calcd for $C_{19}H_{23}FN_4O$: 342.1856, found: 342.1841.

EXAMPLE 3

(7R,9aS)-7-(Substituted)methyl-2-(5-fluoropyrimidin-2-yl)-2,3,4,6,7,8,9,9a-octahydro-1H-pyrido[1,2-a]pyrazines

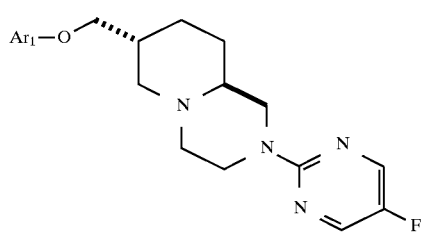

Compounds of the above formula were prepared according to Example 1 using (7R,9aS)-7-hydroxymethyl-2-(5-fluoropyrimidin-2-yl)-2,3,4,6,7,8,9,9a-octahydro-1H-pyrido[1,2-a]pyrazine (Preparation 5) and the appropriate phenol. Purification was generally accomplished by flash silica gel chromatography using mixtures of ethyl acetate and hexane or mixtures of chloroform and methanol as the eluting solvent. The stereochemical configuration, 7-substituent, melting point of the monohydrochloride salt and HRMS or $^{13}$C NMR data are shown.

Example 3a (7R,9aS)-7-(3-Cyanophenoxy)methyl; mp 192°–194° C.; HRSM calcd for $C_{20}H_{22}FN_5O$: 367.1808, found: 367.1821.

Example 3b (7R,9aS)-7-(4-Cyanophenoxy)methyl; mp 256°–257° C.; HRSM calcd for $C_{20}H_{22}FN_5O$: 367.1808, found: 367.1793.

Example 3c (7R,9aS)-7-(2-Methoxy-3-(1-methyl)ethyl-phenoxy) methyl; mp>286° C.; HRSM calcd for $C_{23}H_{31}FN_4O_2$: 414.2424, found: 414.2418.

Example 3d (7R,9aS)-7-(2-Fluorophenoxy)methyl; mp 209°–210° C.; HRSM calcd for $C_{19}H_{22}F_2N_4O$: 360.1762, found: 360.1767.

Example 3e (7R,9aS)-7-(3-Fluorophenoxy)methyl; mp 229°–232° C.; HRSM calcd for $C_{19}H_{22}F_2N_4O$: 360.1767, found: 360.1755.

Example 3f (7R,9aS)-7-(4-Fluorophenoxy)methyl; mp 249°–254° C.; HRSM calcd for $C_{19}H_{22}F_2N_4O$: 360.1767, found: 360.1741.

Example 3g (7R,9aS)-7-(3,4-Difluorophenoxy)methyl; mp 229°–236° C.; HRMS calcd. for $C_{19}H_{21}F_3N_4O$: 378.1667, found: 378.1660.

Example 3h (7R,9aS)-7-(3,5-Difluorophenoxy)methyl; mp 248°–250° C.; HRSM calcd for $C_{19}H_{21}F_3N_4O$: 378.1667, found: 378.1680.

Example 3i (7R,9aS)-7-(4-Iodophenoxy)methyl; mp 284°–286° C.; HRSM calcd for $C_{19}H_{22}FIN_4O$: 468.0822, found: 468.0785.

EXAMPLE 4

(7RS,9aSR)-7-Phenoxymethyl-2-(5-fluoro-4-thiomethylpyrimidin-2-yl)-2,3,4,6,7,8,9,9a-octahydro-1H-pyrido[1,2-a]pyrazine

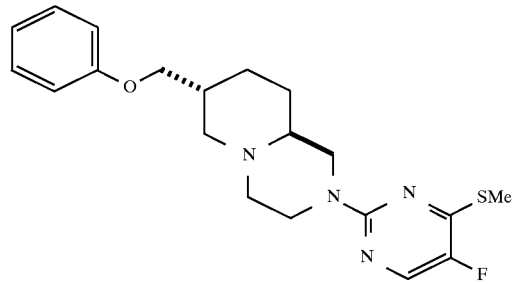

The title compound was prepared according to Example 1 using phenol and (7RS,9aSR)-7-hydroxymethyl-2-(5-fluoro-4-thiomethyl) pyrimidin-2-yl)-2,3,4,6,7,8,9,9a-octahydro-1H-pyrido[1,2-a]pyrazine (Preparation 6). mp (.HCl) 192°–198° C. Anal calcd for $C_{20}H_{25}FN_4OS$: C, 61.82; H, 6.49; N, 14.42. Found: C, 61.52; H, 6.56; N, 14.42.

EXAMPLE 5

(7RS,9aSR)-7-Phenoxymethyl-2-(5-fluoropyrimidin-2-yl)-2,3,4,6,7,8,9,9a-octahydro-1H-pyrido[1,2-a]pyrazine

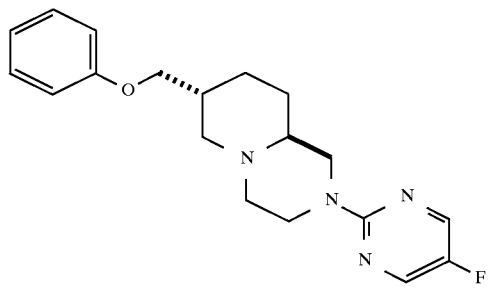

A solution of 3.74 g (9.63 mmol) of (7RS,9aSR)-7-phenoxymethyl-2-(5-fluoro-4-thiomethylpyrimidin-2-yl)-2,3,4,6,7,8,9,9a-octahydro-1H-pyrido[1,2-a]pyrazine (Example 4) in 200 mL of ethanol was treated with 0.3 g of Raney nickle and the mixture was refluxed for 2 h. An additional 0.3 g of catalyst was added and reflux continued for 24 h. A third quantity of catalyst (0.3 g) was added and reflux continued for another 24 h. A fourth quantity of catalyst (0.3 g) was added and refluxed for 4 h. The mixture was cooled to room temperature, filtered through Celite, washing with ethanol and the filtrate was evaporated. Purification by flash silica gel chromatography with methylene chloride and 99:1 methylene chloride:methanol gave 1.30 g (39%) of the title compound. mp (.HCl) 215°–217° C. HRMS calcd for $C_{19}H_{23}FN_4O$: 342.1851, found: 342.1853.

EXAMPLE 6

(7RS,9aSR)-7-(4-Fluorophenoxy)methyl-2-(5-fluoro-4-thiomethyl-pyrimidin-2-yl)-2,3,4,6,7,8,9,9a-octahydro-1H-pyrido[1,2-a]pyrazine

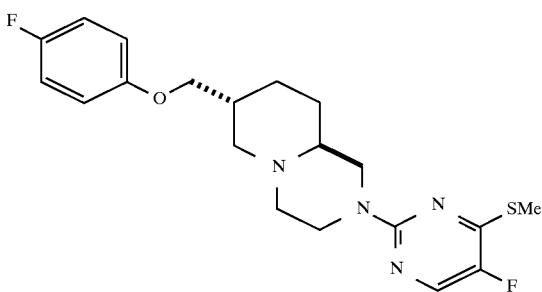

The title compound was prepared according to Example 1 using 4-fluorophenol and (7RS,9aSR)-7-hydroxymethyl-2-(5-fluoro-4-thiomethylpyrimidin-2-yl)-2,3,4,6,7,8,9,9a-octahydro-1 H-pyrido[1,2-a]pyrazine (Preparation 6). mp (.HCl) 201°–210° C. $^{13}$C NMR (base, CDCl$_3$): δ 11.5, 27.0, 29.0, 36.4, 44.3, 49.8, 54.8, 58.8, 60.7, 71.6, 115.35, 115.45, 115.59, 115.90, 140.4, 140.7, 150.9, 155.1, 158.8. HRSM calcd for $C_{20}H_{24}F_2N_4$ OS: 406.166, found: 406.161.

EXAMPLE 7
(7RS,9aSR)-7-(4-Fluorophenyl)methyl-2-(5-fluoropyrimidin-2-yl)-2,3,4,6,7,8,9,9a-octahydro-1H-pyrido[1,2-a]pyrazine

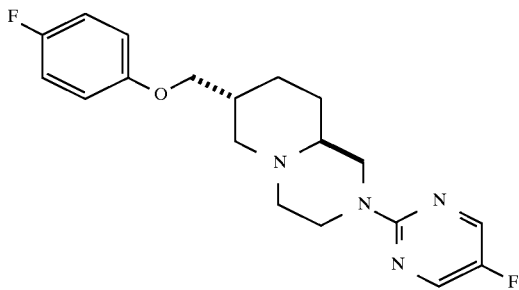

Using the procedure described in Example 5, 8.23 g (20.3 mmol) of (7RS,9aSR)-7-(4-fluorophenoxy)methyl-2-(5-fluoro-4-thiomethylpyrimidin-2-yl)-2,3,4,6,7,8,9,9a-octahydro-1H-pyrido[1,2-a]pyrazine gave 3.4 g of the title compound. mp (.HCl) 249°–253° C. Anal calcd for $C_{19}H_{22}F_2N_4O$.HCl: C, 57.50; H, 5.84; N, 14.12; found: C, 57.40; H, 5.84; N,13.99.

EXAMPLE 8
(7SR,9aSR)-7-((4-Fluorophenoxy)methyl)-2-(pyrimidin-2-yl)-2,3,4,6,7,8,9,9a-octahydro-1H-pyrido[1,2-a]pyrazine

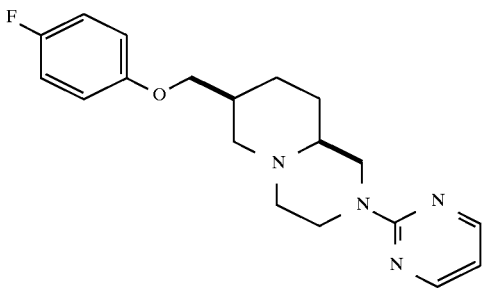

A solution of 0.600 g (2.43 mmol) of (7SR,9aSR)-7-hydroxymethyl-2-(pyrimidin-2-yl)-2,3,4,6,7,8,9,9a-octahydro-1H-pyrido[1,2-a]pyrazine (U.S. Pat. No. 5,122,525) and 0.34 mL (2.7 mmol) of triethylamine in 10 mL of methylene chloride at 0° C. was treated with 0.20 mL (2.5 mmol) of methanesulfonyl chloride. After 10 min, the mixture was diluted with water, basified with 1M NaOH, separated, and the mixture was extracted with more methylene chloride (2×). The combined organic layers were washed with water (1×), dried (magnesium sulfate), filtered, and evaporated to give 0.77 g (2.6 mmol) of mesylate.

A solution of 0.82 g (7.3 mmol) of 4-fluorophenol in 8 mL of DMF was treated with 0.35 g (8.8 mmol) of sodium hydride (60% oil dispersion) and allowed to react for 2 h at 40°–50° C. The reaction mixture was cooled to room temperature and a solution of 0.77 g (2.6 mmol) of the above mesylate in 8 mL of DMF was added. The reaction was then heated at 100° C. for 16 h. After cooling to room temperature, the solvent was evaporated, the residue taken up in water, the pH adjusted to 2 with 1M HCl, and washed with ethyl acetate. The aqueous phase was made basic (pH 11) with 1M NaOH and extracted with ethyl acetate (3×). The combined organic layers were dried (magnesium sulfate), filtered, and evaported to give 0.430 g of crude product. Purification by silica gel flash chromatography eluting with 90:10 ethyl acetate:hexane gave 0.340 g (38%) of the title compound. A salt was prepared by mixing an ethanol-ethyl acetate solution of 0.29 g free base with a solution of 98 mg of maleic acid in ethanol and evaporating to dryness. The white solid was triturated with ether and dried in vacuo to give 0.35 g of salt. mp (.$C_4H_4O_4$) 128°–139° C. $^{13}$C. NMR (base, CDCl$_3$): δ 24.8, 25.2, 33.8, 43.6, 49.1, 54.9, 56.6, 61.1, 69.5, 109.7, 115.48, 115.25, 115.58, 115.83, 155.4, 157.7, 161.5. Anal. calcd for $C_{19}H_{23}N_4OF$: C, 66.64; H, 6.77; N, 16.36. Found: C, 66.28; H, 7.02; N, 16.45.

EXAMPLE 9
(7RS,9aSR)-7-Phenoxymethyl-2-(pyrimidin-2-yl)-2,3,4,6,7,8,9,9a-octahydro-1H-pyrido[1,2-a]pyrazine

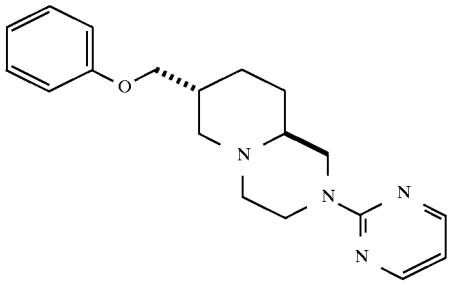

A solution of 1.0 g (4.0 mmol) of (7RS,9aSR)-7-hydroxymethyl-2-(pyrimidin-2-yl)-2,3,4,6,7,8,9,9a-octahydro-1H-pyrido[1,2-a]pyrazine (Preparation 3) in 20 mL dry methylene chloride was cooled to 0° C., and treated with 0.57 mL (4.4 mmol) of triethylamine and 0.33 mL(4.2 mmol) of methanesulfonyl chloride dropwise. After 15 min, water was added and the pH adjusted to 11 with 1N NaOH. The layers were separated and the aqueous phase was extracted with methylene chloride (2×). The combined organic phase was dried (magnesium sulfate), filtered and evaporated to give 1.0 g (76%) of mesylate.

A mixture of 10 mL of DMF, 0.90 g (9.6 mmol) of phenol, and 0.45 g (10.2 mmol) of NaH (60% oil dispersion) in a dry flask was stirred for 1.5 h at 40°–50° C. After cooling to room temperature, the above mesylate was added in 10 mL of DMF, and the solution was heated at 100°–110° C. for 16 h. After cooling to room temperature, water was added, the pH adjusted to 11 with 1N NaOH, and the mixture extracted with ethyl acetate (3×), dried (magnesium sulfate), filtered and evaportated. The crude product was triturated with a few mL of water re-disolved in ethyl acetate, dried (magnesium sulfate), filtered and evaporated. Flash chromatography on silical gel with ethyl acetate gave 0.68 g of the free base as a white solid. mp (.2HCl) 218°–223° C. $^{13}$C. NMR (base, CDCl$_3$): δ 27.0, 29.0, 36.4, 43.6, 49.1, 54.9, 58.8, 60.8, 70.9, 109.8, 114.5, 120.6, 129.4, 157.7, 159.0, 161.5. Calcd for C$_{19}$H$_{24}$NO$_4$.2HCl: C, 57.43; H; 6.60; N, 14.10; found: C, 57.54; H, 6.88; N, 13.83.

EXAMPLE 10

7-(Substitutedphenoxymethyl)-2-(pyrimidin-2-yl)-2,3,4,6,7,8,9,9a-octahydro-1H-pyrido[1,2-a]pyrazines

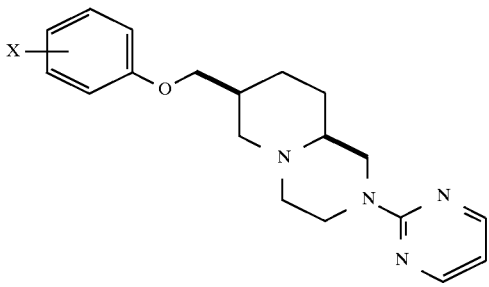

Compounds of the above formula were prepared according to Example 8 from (7SR,9aSR)-7-hydroxymethyl-2-(pyrimidin-2-yl)-2,3,4,6,7,8,9,9a-octahydro-1H-pyrido[1,2-a]pyrazines (U.S. Pat. No. 5,122,525) and the appropriate phenol. Purification was generally accomplished by flash silica gel chromatography using mixtures of ethyl acetate and hexane or mixture of chloroform and methanol as the eluting solvent. The stereochemical configuration, 7-phenoxymethyl substitutent, melting point of the monohydro-chloride salt and HRMS or combustion analysis or $^{13}$C NMR data are shown.

Example 10a (7SR,9aSR)-7-(4-Acetamidophenoxy)methyl; mp 123° C. (dec); $^{13}$C NMR (base, CDCl$_3$):δ 6 24.3, 24.8, 25.1, 33.7, 43.6, 49.1, 54.8, 56.6, 61.1, 69.1, 109.7, 114.9, 121.9, 130.9, 156.2, 157.7, 161.5, 168.3.

Example 10b (7SR,9aSR)-7-((4-Trifluoromethyl)phenoxy)methyl; mp 104–119° C.; HRMS calcd for C$_{20}$H$_{23}$F$_3$N$_4$O: 392.1819, found: 392.1833.

Example 10c (7SR,9aSR)-7-((4-Methoxy)phenoxy)methyl; mp 112°–114° C.; Anal calcd for C$_{20}$H$_{26}$N$_4$O$_2$.HCl: C, 61.44; H, 6.96; N, 14.33. Found: C, 61.23; H, 7.29; N, 14.51.

Example 10d (7SR,9aSR)-7-((4-Carboethoxy)phenoxy)methyl; mp 189°–191° C.; HRMS calcd for C$_{22}$H$_{28}$N$_4$O$_3$: 396.2162, found: 396.2179.

EXAMPLE 11

(7R,9aS)-7-(4-Fluorophenoxy)methyl-2-(pyrimidin-2-yl)-2,3,4,6,7,8,9,9a-octahydro-1H-pyrido[1,2-a]pyrazine

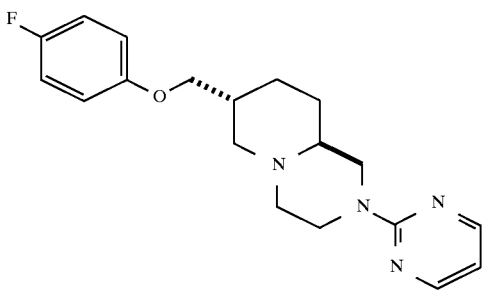

The title compound was prepared according to Preparation 3 with 2-chloropyrimidine and (7R,9aS)-7-(4-fluorophenoxy)methyl-2,3,4,6,7,8,9,9a-octahydro-1H-pyrido[1,2-a]pyrazine (Preparation 8). mp (.HCl) 283°–285° C. HRMS calcd for C$_{19}$H$_{23}$FN$_4$O: 342.1856; found: 342.1867.

EXAMPLE 12

(7R,9aS)-7-(2-Phenyl)ethyl-2-(5-fluoropyrimidin-2-yl)-2,3,4,6,7,8,9,9a-octahydro-1H-pyrido[1,2-a]pyrazine

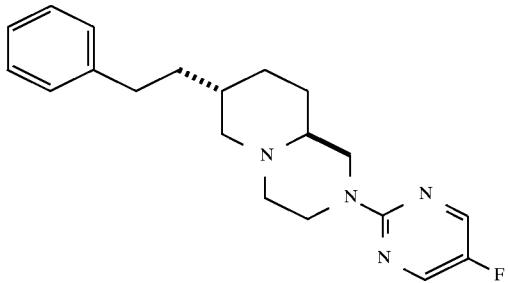

A mixture of 3.75 g (14.1 mmol) of (7R,9aS)-7-hydroxymethyl-2-(5-fluoropyrimidin-2-yl)-2,3,4,6,7,8,9,9a-octahydro-1H-pyrido[1,2-a]pyrazine (Preparation 5), 2.48 g (21.2 mmol) of N-methylmorpholine-N-oxide, 5.0 g of 4 Å molecular sieves, 0.495 g (1.41 mmol) of tetrapropylammonium perruthenate, and 375 mL of methylene chloride was stirred at ambient temperature for 2 h. The reaction was quenched with saturated sodium thiosulfate and filtered through Celite. The filtrate was washed with brine, dried (magnesium sulfate), filtered and evaporated. Purification by flash silica gel chromatography with 95:5 chloroform-:methanol gave 2.27 g (61%) of (7R,9aS)-7-formyl-2-(5-fluoropyrimidin-2-yl)-2,3,4,6,7,8,9,9a-octahydro-1H-pyrido[1,2-a]pyrazine.

A solution of 1.70 g (4.38 mmol) of benzy triphenyl phosphonium chloride in 20 mL of dry THF was chilled to −78° C. and treated with 1.75 mL (4.38 mmol) of n-butyllithium (2.5M in hexane). After 15 min, 1.05 g (3.98 mmol) of (7R,9aS)-7-formyl-2-(5-fluoropyrimidin-2-yl)-2,3,4,6,7,8,9,9a-octahydro-1H-pyrido[1,2-a]pyrazine in 20 mL of dry THF was added dropwise over 30 min, the cooling bath was removed and the solution allowed to warm slowly to ambient temperature overnight (16 h). The solution was concentrated in vacuo and the residue was partitioned between ethyl ether and water. The organic layer was dried (magnesium sulfate), filtered and evaporated. Purification by flash silica gel chromatography with petroleum ether:ethyl ether in ratios from 4:1 to 3:1 gave the following isomers of 7-(2-phenyl)ethenyl-2-(5-fluoropyrimidin-2-yl)-2,3,4,6,7,8,9,9a-octahydro-1H-pyrido[1,2-a]pyrazine: E-(7S,9aS), 0.19 g (Rf=0.75 with 3:1 hexane:ethyl acetate); Z-(7R,9aS), 0.16 g (Rf=0.47 with 3:1 hexane:ethyl acetate); E-(7R,9aS), 0.46 g (Rf=23 with 3:1 hexane:ethyl acetate).

A mixture of 0.15 g (0.44 mmol) of Z-(7R,9aS)-7-(2-phenyl)-ethenyl-2-(5-fluoropyrimidin-2-yl)-2,3,4,6,7,8,9,9a-octahydro-1H-pyrido[1,2-a]pyrazine, 0.015 g of 10% palladium on carbon and 25 mL of ethanol was shaken under 40 psig of hydrogen gas in a Parr apparatus for 6 h. The mixture was filtered through Celite, and the filtrate concentrated to give 0.124 g (83%) of (7R,9aS)-7-(2-phenyl)ethyl-2-(5-fluoropyrimidin-2-yl)-2,3,4,6,7,8,9,9a-octahydro-1H-pyrido[1,2-a]pyrazine. mp (.HCl) 250°–252° C. HRMS calcd for $C_{20}H_{26}FN_4O$ (MH+): 341.2142, found: 341.2126.

EXAMPLE 13
(7SR,9aSR)-7-Phenoxymethyl-2-(pyridin-2-yl)-2,3,4,6,7,8,9,9a-octahydro-1H-pyrido[1,2-a]pyrazine

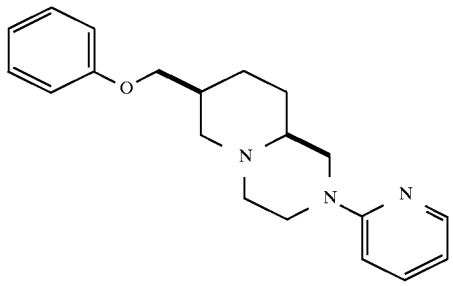

The title compound was prepared according to Example 8 from phenol and (7SR,9aSR)-hydroxymethyl-2,3,4,6,7,8,9,9a-octahydro-2-pyridin-2-yl-1H-pyrido[1,2-a]pyrazine (U.S. Pat. No. 5,122,525). $^{13}$C. NMR (base, CDCl$_3$): δ 24.8, 25.3, 33.8, 45.1, 50.7, 54.8, 56.6, 61.0, 68.8, 107.1, 113.1, 114.7, 120.5, 129.4, 137.4, 148.0, 159.3, 159.4. HRMS calcd for $C_{20}H_{25}N_3O$: 323.2000, found: 323.2003

EXAMPLE 14
(7RS,9aSR)-7-Phenoxymethyl-2-(pyridin-2-yl)-2,3,4,6,7,8,9,9a-octahydro-1H-pyrido[1,2-a]pyrazine

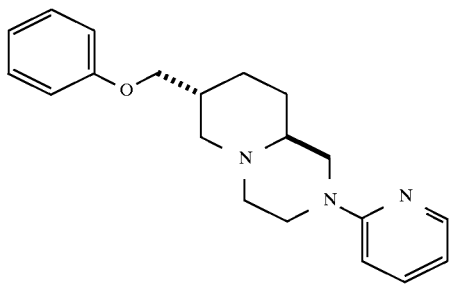

The title compound was prepared according to Example 9 from (7RS,9aSR)-hydroxymethyl-2-(pyridin-2-yl)-2,3,4,6,7,8,9,9a-octahydro-1H-pyrido[1,2-a]pyrazine (Preparation 11) and phenol. mp (.HCl) 238°–241° C. $^{13}$C. NMR (base, CDCl$_3$): δ 5 27.0, 29.2, 36.4, 45.2, 50.8, 54.8, 58.8, 60.7, 70.9, 107.0, 113.2, 114.5, 120.7, 113.2, 114.5, 120.7, 129.4, 137.5, 148.0, 159.0, 159.4. Anal. calcd for $C_{20}H_{25}N_3O$ C, 74.26; H, 7.79; N, 12.99; found: C., 74.12; H, 7.84; N, 12.86.

EXAMPLE 15
(7RS,9aSR)-7-(4-Fluorophenoxy)methyl-2-(3,5-dichloropyridin-2-yl)-2,3,4,6,7,8,9,9a-octahydro-1H-pyrido[1,2-a]pyrazine

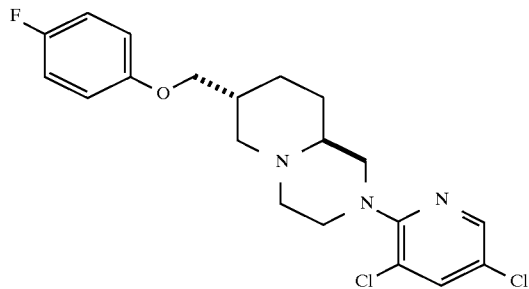

A mixture of 0.75 g (4.4 mmol) of (7RS,9aSR)-7-hydroxymethyl-2,3,4,6,7,8,9,9a-octahydro-1H-pyrido[1,2-a]pyrazine, 4.02 g (22.1 mmol) of 2,3,5-trichloropyridine, 1.12 g (10.6 mmol) of sodium carbonate and 30 mL of isoamylalcohol was refluxed for 72 h. The mixture was cooled to room temperature, filtered, and concentrated in vacuo. The residue was dissolved in ethyl acetate and washed with saturated sodium carbonate. The organic layer was dried (magnesium sulfate), filtered and evaporated, and the crude product was purified by flash chromatography on silica gel eluting with 95:5 chloroform:methanol to give 1.10 g (80%) of (7RS,9aSR)-7-hydroxymethyl-2-(3,5-dichloro-pyridin-2-yl)-2,3,4,6,7,8,9,9a-octahydro-1H-pyrido[1,2-a]pyrazine.

A solution of 0.50 g (1.58 mmol) of (7RS,9aSR)-7-hydroxymethyl-2-(3,5-dichloro-pyridin-2-yl)-2,3,4,6,7,8,9,9a-octahydro-1H-pyrido[1,2-a]pyrazine in 40 mL of THF with 0.266 g (2.32 mmol) of 4-fluorophenol, 0.498 g (1.90 mmol) of triphenylphosphine, and 0.30 mL (1.90 mmol) of diethyl azodicarboxylate was stirred at room temperature for 16 h. The mixture was diluted with ethyl acetate and treated with excess HCl(g) in ether. The solvent was evaported and the residue washed repeatedly with 1:1 ethyl acetate:ether. The white powder was dissolved in chloroform, washed with 1M NaOH (2x), dried (magnesium sulfate), filtered and evaporated. The crude product was purified by flash silica gel chromatography with 50:50 ethyl acetate: hexane to give 0.566 g (87%) of title compound. mp (.HCl) 247°–248° C. $^{13}$C. NMR (base, CDCl$_3$): δ 8 27.1, 29.0, 36.4, 49.0, 54.4, 54.8, 58.6, 60.7, 71.7, 115.36, 115.47, 115.59, 115.89, 122.3, 124.0, 138.2, 155.1, 155.6, 156.6, 158.8. HRMS calc for $C_{20}H_{22}C_2FN_3O$: 409.1124, found: 409.1141.

EXAMPLE 16
7-(4-Fluorophenoxy)methyl-2-(substituted-pyridin-2-yl)-2,3,4,6,7,8,9,9a-octahydro-1H-pyrido[1,2-a]pyrazines

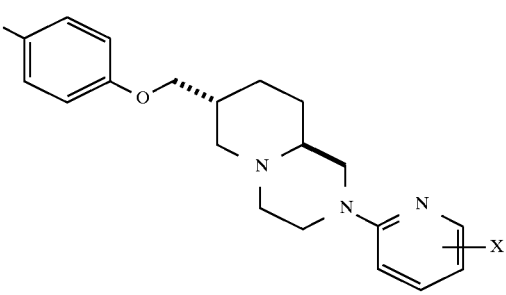

Compounds were prepared according to Example 15 from (7RS,9aSR)-7-hydroxymethyl-2,3,4,6,7,8,9,9a-octahydro-1H-pyrido[1,2-a]pyrazine (U.S. Pat. No. 5,326,874), using the appropriate 2-chloro or 2-bromo pyridine in the first step and 4-fluorophenol in the second step. Purification was generally accomplished by flash silica gel chromatography using mixtures of ethyl acetate and hexane or mixtures of chloroform and methanol as the eluting solvent. The stereochemical configuration, substituted pyridin-2-yl substitutent, melting point of the monohydrochloride salt and HRMS data are shown.

Example 16a (7RS,9aSR), 2-(3-Cyanopyridin-2-yl); mp 194°–195° C.; HRMS calcd for $C_{21}H_{23}FN_4O$: 366.1855; found: 366.1845.

Example 16b (7RS,9aSR), 2-(4-Methylpyridin-2-yl); mp 264°–266° C.; HRMS calcd for $C_{21}H_{26}FN_3O$: 355.2060, found: 355.2075.

Example 16c (7RS,9aSR), 2-(5-Bromopyridin-2-yl); mp 214°–215° C.; HRMS calcd for $C_{20}H_{23}BrFN_3O$: 419.1008, found: 419.1037.

Example 16d (7RS,9aSR), 2-(3-Chloropyridin-2-yl); mp 174°–175° C.; HRMS calcd for $C_{20}H_{23}ClFN_3O$: 375.1514, found: 375.1528.

EXAMPLE 17

(7RS,9aSR)-7-Phenoxymethyl-2-(5-chloropyridin-2-yl)-2,3,4,6,7,8,9,9a-octahydro-1H-pyrido[1,2-a]pyrazine

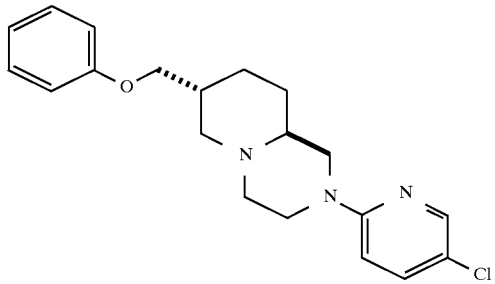

The title compound was prepared according to Example 15 using 2,5-dichloropyridine, (7RS,9aSR)-7-hydroxymethyl-2,3,4,6,7,8,9,9a-octahydro-1H-pyrido[1,2-a]pyrazine (U.S. Pat. No. 5,326,874), and phenol. mp (.HCl) 218°–224° C. $^{13}$C. NMR (base, CDCl$_3$): δ 27.0, 29.1, 36.4, 45.3, 50.9, 54.6, 58.8, 60.5, 70.9, 107.8, 114.5, 120.1, 120.7, 129.4, 137.1, 146.2, 157.6, 159.0. Anal. calcd for $C_{20}H_{24}ClN_3O$ C, 67.12; H, 6.76; N, 11.74; found: C, 67.22; H, 6.85; N, 11.49.

EXAMPLE 18

(7R,9aS)-7-(4-Fluorophenoxy)methyl-2-(pyridin-2-yl)-2,3,4,6,7,8,9,9a-octahydro-1H-pyrido[1,2-a]pyrazine

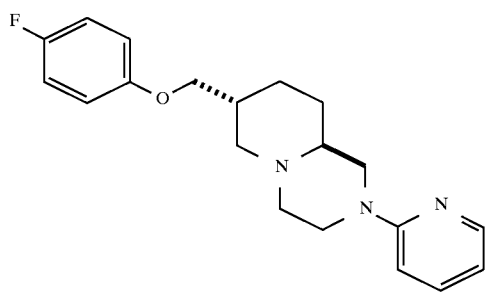

The title compound was synthesized according to Preparation 11 using 2-bromopyridine and (7R,9aS)-7-(4-fluorophenoxy) methyl-2,3,4,6,7,8,9,9a-octahydro-1H-pyrido[1,2-a]pyrazine (Preparation 8). mp (.HCl) 261°–263° C. HRMS calcd for $C_{20}H_{24}FN_3O$: 341.1903; found, 341.1928.

EXAMPLE 19

(7R,9aS)-7-(4-Fluorophenoxy)methyl-2-(5-chloropyridin-2-yl)-2,3,4,6,7,8,9,9a-octahydro-1H-pyrido[1,2-a]pyrazine

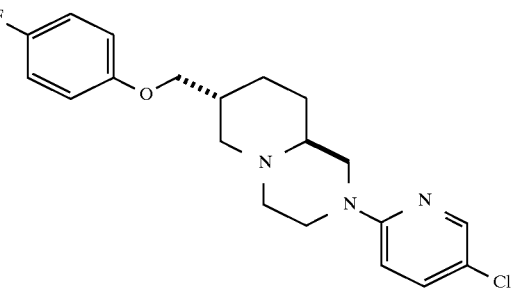

The title compound was prepared according to Preparation 11 using 2,5-dichloropyridine and (7R,9aS)-7-(4-fluorophenoxy) methyl-2,3,4,6,7,8,9,9a-octahydro-1H-pyrido[1,2-a]pyrazine (Preparation 8). mp (.HCl) 237°–238° C. $^{13}$C NMR (base, CDCl$_3$): δ 27.0, 29.1, 36.4, 45.3, 50.9, 54.6, 58.7, 60.5, 71.6, 107.7, 115.36, 115.47, 115.60, 115.90, 120.1, 137.1, 146.3, 155.1, 155.6, 157.6, 158.8. HRMS calcd for $C_{20}H_{23}ClFN_3O$: 375.1514; found, 375.1544.

EXAMPLE 20

(7R,9aS)-7-(4-Fluorophenoxy)methyl-2-(6-chloropyridazin-3-yl)-2,3,4,6,7,8,9,9a-octahydro-1H-pyrido[1,2-a]pyrazine

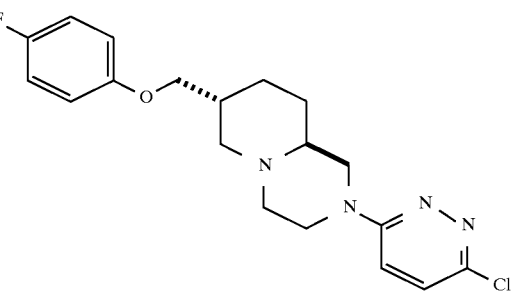

The title compound was prepared according to Preparation 3 with 3,6-dichloropyridazine and (7R,9aS)-7-(4-fluorophenoxy) methyl-2,3,4,6,7,8,9,9a-octahydro-1H-pyrido[1,2-a]pyrazine. mp (.HCl) 265°–270,C. $^{13}$C NMR (base, CDCl$_3$): δ 26.8, 29.0, 36.4, 45.1, 50.4, 54.4, 58.6, 60.3, 71.5, 115.2, 115.3, 115.4, 115.6, 115.9, 128.7, 146.7, 155.0, 155.6, 158.76, 158.82. HRMS calcd for $C_{19}H_{22}ClFN_4O$: 376.1461; found: 376.1453.

EXAMPLE 21

(7S,9aR)-7-(4-Fluorophenoxy)methyl-2-(5-fluoropyrimidin-2-yl)-2,3,4,6,7,8,9,9a-octahydro-1H-pyrido[1,2-a]pyrazine

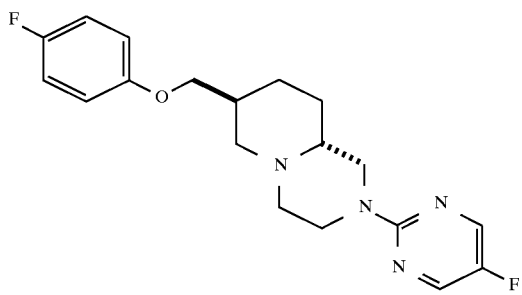

The title compound was prepared according to Preparation 3 with 2-chloro-5-fluoropyrimidine and (7S,9R)-7-(4-fluorophenoxy)methyl-2,3,4,6,7,8,9,9a-octahydro-1H-pyrido[1,2-a]pyrazine (Preparation 9). mp (.HCl) 251°–252C. $^{13}$C NMR (base, CDCl$_3$): δ 27.0, 29.0, 36.4, 44.3, 49.8, 54.8, 58.8, 60.7, 71.6, 115.35, 115.45, 115.59, 115.89, 145.0, 145.3, 149.9, 153.2, 155.1, 155.6, 158.7, 158.8. HRMS calcd for $C_{19}H_{22}F_2N_4O$: 360.1762; found: 360.1763.

EXAMPLE 22

(7R,9aR)-7-(4-Fluorophenoxy)methyl-2-(5-fluoropyrimidin-2-yl)-2,3,4,6,7,8,9,9a-octahydro-1H-pyrido[1,2-a]pyrazine

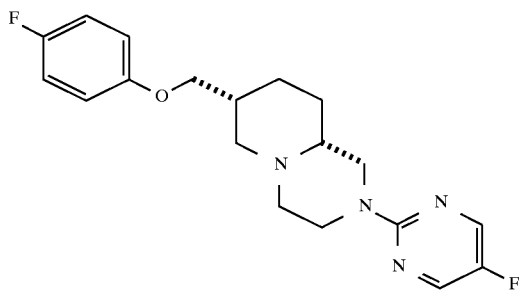

The title compound was prepared according to Preparation 3 with 2-chloro-5-fluoropyrimidine and (7R,9R)-7-(4-fluorophenoxy)methyl-2,3,4,6,7,8,9,9a-octahydro-1H-pyrido[1,2-a]pyrazine (Preparation 10). mp (.HCl) 232.5°–324° C. $^{13}$C NMR (base, CDCl$_3$): δ 24.8, 25.1, 33.8, 44.3, 49.7, 54.8, 56.6, 61.0, 69.5, 115.48, 115.53, 115.59, 115.83, 145.0, 145.3, 149.9, 153.1, 155.4, 155.5, 158.69, 158.74. HRMS calcd for $C_{19}H_{22}F_2N_4O$: 360.1762; found: 360.1755.

EXAMPLE 23

(7RS,9aSR)-7-(4-Fluorophenoxy)methyl-2-(2-cyano-4-fluorophenyl)-2,3,4,6,7,8,9,9a-octahydro-1H-pyrido[1,2-a]pyrazine

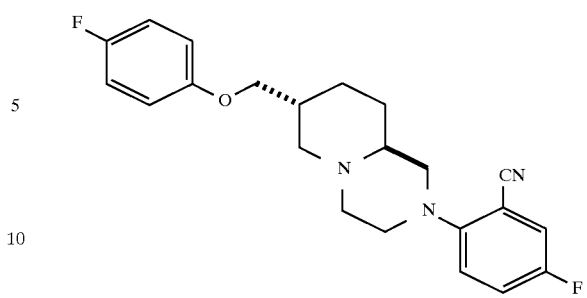

A mixture of 1.05 g (6.17 mmol) of (7RS,9aSR)-7-hydroxymethyl-2,3,4,6,7,8,9,9a-octahydro-1H-pyrido[1,2-a]pyrazine (U.S. Pat. No. 5,326,874) and 1.29 g (9.25 mmol) of 2,5-difluorobenzonitrile in 20 mL of DMSO was heated at 100° C. for 16 h. The mixture was cooled to room temperature, acidified with 1M HCl, washed with ether (3×), made basic with conc. ammonium hydroxide, and extracted with ethyl acetate (3×). The combined organic layers were washed with water (3×), dried (magnesium sulfate), filtered and evaporated. Purification by silica gel MPLC with 90:10 chloroform:methanol gave 0.51 g of (7RS,9aSR)-7-hydroxymethyl-2-(2-cyano-4-fluorophenyl)-2,3,4,6,7,8,9,9a-octahydro-1H-pyrido[1,2-a]pyrazine.

A solution of 0.51 g (1.8 mmol) of (7RS,9aSR)-7-hydroxymethyl-2-(2-cyano-4-fluorophenyl)-2,3,4,6,7,8,9,9a-octahydro-1H-pyrido[1,2-a]pyrazine, 0.555 g (2.12 mmol) of triphenylphosphine, and 0.296 g (2.64 mmol) of 4-fluorophenol in 8 mL of dry THF was treated with 0.368 g (2.12 mmol) of diethyl azodicarboxylate and stirred at ambient temperature for 24 h. The mixture was diluted with ether, and 1M HCl was added until a gummy residue formed. The layers were separated and the aqueous layer was washed with ether (3×). The aqueous layer was combined with the gummy residue and dissolved in a mixture of ethyl acetate and 10% ammonium hydroxide, the layers were separated and the aqueous layer was extracted with more ethyl acetate (2×). The organic layers were evaporated, the residue dissolved in chloroform, washed with 1M NaOH (3×), dried (magnesium sulfate), filtered and evaporated. The product was dissolved in absolute ethanol, filtered and evaporated to give 0.21 g of the title compound. mp (.HCl) 235°–240° C. HRMS calcd for $C_{22}H_{23}F_2N_3O$: 383.1809, found: 383.1796.

EXAMPLE 24

(7R,9aS)-7-(4-Fluorophenoxy)methyl-2-(2-amino-4-fluorophenyl)-2,3,4,6,7,8,9,9a-octahydro-1H-pyrido[1,2-a]pyrazine

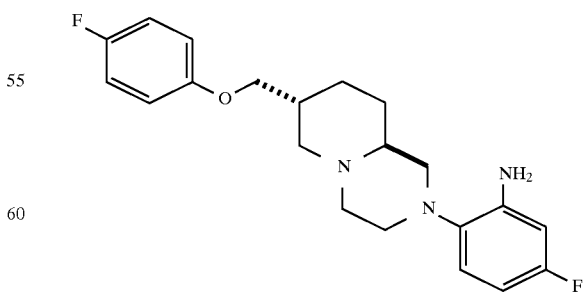

A solution of 4.38 g (25.8 mmol) of (7R,9aS)-7-hydroxymethyl-2,3,4,6,7,8,9,9a-octahydro-1H-pyrido[1,2-a]pyrazine (preparation 1), 4.19 mL (38.7 mmol) of 2,5- difluoronitrobenzene, and 5.46 g (51.5 mmol) of sodium carbonate in 25 mL of DMSO was heated at 95° C. for 16 h. The mixture was cooled to room temperature, acidified with 1M HCl, and washed with ethyl ether (3×). The aqueous layer was made basic with conc. ammonium hydroxide and extracted with ethyl acetate (3×). The combined organic layers were washed with water (3×), dried (magnesium sulfate), filtered and evaporated. Purification by flash silica gel chromatography with 90:10 chloroform: methanol gave 6.19 g (78%) of (7R,9aS)-7-hydroxymethyl-2-(4-fluoro-2-nitrophenyl)-2,3,4,6,7,8,9,9a-octahydro-1H-pyrido[1,2-a]pyrazine.

A solution of 3.0 g (9.7 mmol) of (7R,9aS)-7-hydroxymethyl-2-(4-fluoro-2-nitrophenyl)-2,3,4,6,7,8,9,9a-octahydro-1 H-pyrido[1,2-a]pyrazine in 50 mL of methanol and 50 mL of THF was treated with 0.30 g of 10% Pd/C and treated with 30 psi of hydrogen in a Parr apparatus for 1.5 h. The catalyst was removed by filtration and the red solution concentrated to give 2.65 g (98%) of (7R,9aS)-7-hydroxymethyl-2-(2-amino-4-fluorophenyl)-2,3,4,6,7,8,9,9a-octahydro-1H-pyrido[1,2-a]pyrazine.

A solution of 4.12 g (14.8 mmol) of (7R,9aS)-7-hydroxymethyl-2-(2-amino-4-fluorophenyl)-2,3,4,6,7,8,9,9a-octahydro-1H-pyrido[1,2-a]pyrazine, 2.48 g (22.2 mmol) of 4-fluorophenol and 4.65 g (17.7 mmol) of triphenylphosphine in 225 mL of THF was treated with 2.79 mL (17.7 mmol) of diethyl azodicarboxylate and stirred at room temperature for 4 days. The solvent was evaporated, the residue dissolved in 1:1 ethyl acetate:ethyl ether and the solution treated with HCl(g) in ether until precipitation ceased. The mixture was filtered and the solid washed repeatedly with ethyl acetate. The solid was dissolved in a mixture of chloroform and 1M sodium hydroxide, the layers separated, and the organic phase was dried (magnesium sulfate), filtered and evaporated. Purification by flash silica gel chromatography with 60:40 ethyl acetate:hexane gave 1.69 g (30%) of the title compound. mp (.HCl) 144°–149° C. HRMS calcd for $C_{21}H_{25}F_2N_3O$: 373.1966, found: 373.1958.

EXAMPLE 25
(7RS,9aSR)-7-(4-Fluorophenoxy)methyl-2-(4-fluorophenyl)-2,3,4,6,7,8,9,9a-octahydro-1H-pyrido[1,2-a]pyrazine

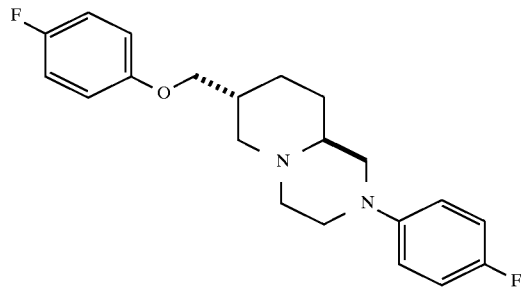

A solution of 1.53 g (4.10 mmol) of (7R,9aS)-7-hydroxymethyl-2-(2-amino-4-fluorophenyl)-2,3,4,6,7,8,9,9a-octahydro-1H-pyrido[1,2-a]-pyrazine (Example 24) in 160 mL of THF was added to a solution of 1.21 mL (9.02 mmol) of 97% isoamyl nitrite in 100 mL of THF over a 2 h period. After the addition was complete, the solution was heated at reflux for 4 days. The solvent was evaporated, the residue was dissolved in ethyl acetate and washed with 1M sodium hydroxide (3×). The organic phase was dried (magnesium sulfate), filtered and evaporated. Purification by flash silica gel chromatography with 50:50 ethyl acetate-:hexane gave 0.75 g (52%) of a yellow solid. mp (.HCl) 221°–223° C. HRMS calcd for $C_{21}H_{24}F_2N_2O$: 358.1857, found: 358.1875.

EXAMPLE 26
(7R,9aS)-7-Phenoxymethyl-2-phenyl-2,3,4,6,7,8,9,9a-octahydro-1H-pyrido[1,2-a]pyrazine

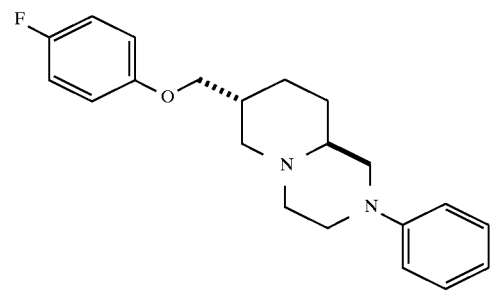

A mixture of 0.500 g (1.89 mmol) of (7R,9aS)-7-(4-fluorophenoxy)methyl-2,3,4,6,7,8,9,9a-octahydro-1H-pyrido[1,2-a]pyrazine (Preparation 8), 0.400 g (2.84 mmol) of 4-fluoronitrobenzene and 0.401 g (3.78 mmol) of sodium carbonate in 15 mL of DMSO was heated at 95° C. for 16 h. The mixture was cooled to room temperature, acidified with 1M HCl, washed with ethyl ether (3×), basified with conc. ammonium hydroxide and extracted with ethyl acetate (3×). The combined organic layers were washed with water and brine, dried (magnesium sulfate), filtered and evaporated to give 0.614 g of (7R,9aS)-7-(4-fluorophenoxy) methyl-2-(4-nitrophenyl)-2,3,4,6,7,8,9,9a-octahydro-1H-pyrido[1,2-a]pyrazine.

A mixture of 0.600 g (1.56 mmol) of (7R,9aS)-7-(4-fluorophenoxy)methyl-2-(4-nitrophenyl)-2,3,4,6,7,8,9,9a-octahydro-1H-pyrido[1,2-a]pyrazine and 90 mg of 10% Pd/C in 25 mL of THF was placed in a Parr hydrogenator at 30 psi for 4 h. The catalyst was removed by filtration through Celite and the filtrate was evaporated to give 0.45 g (82%) of (7R,9aS)-7-(4-fluorophenoxy)methyl-2-(4-aminophenyl)-2,3,4,6,7,8,9,9a-octahydro-1H-pyrido[1,2-a]pyrazine.

A solution of 0.400 g (1.13 mmol) of (7R,9aS)-7-(4-fluorophenoxy)methyl-2-(4-aminophenyl)-2,3,4,6,7,8,9,9a-octahydro-1H-pyrido[1,2-a]pyrazine in 20 mL of THF was added dropwise to a solution of 0.33 mL (2.48 mmol) of isoamyl nitrite in 15 mL of THF. After the addition was complete, the solution was refluxed for 24 h. The solvent was evaporated, the residue dissolved in ethyl acetate, washed with 1M sodium hydroxide (3×), washed with brine (1×), dried (magnesium sulfate), filtered and evaporated. Purification by flash silica gel chromatography with ethyl acetate gave 0.060 g (16%) of the title compound. mp (.HCl) 247°–252° C. HRMS calcd for $C_{21}H_{25}FN_2O$: 340.1951, found: 340.1989.

EXAMPLE 27
(7RS,9aSR)-7-(4-Fluorophenoxy)methyl-2-(6-methoxypyridin-2-yl)-2,3,4,6,7,8,9,9a-octahydro-1H-pyrido[1,2-a]pyrazine

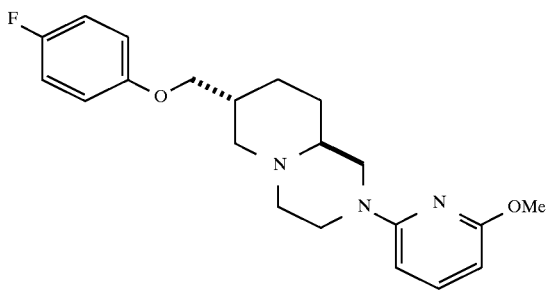

According to the procedure reported by Wynberg (*J. Org. Chem.* 1993, 58, 5101), a solution 0.50 g (2.9 mmol) of racemic (7RS ,9aSR)-7-hydroxymethyl-2,3,4,6,7,8,9,9a-octahydro-1H-pyrido[1,2-a]pyrazine in 10 mL of dry THF at 0° C. was treated with 2.59 mL (6.5 mmol) of n-butyl lithium (2.5M in hexane). The mixture was kept at 0° C. for 30 min and at room temperature for 1 h, and 0.39 mL (2.94 mmol) of 2,6-dimethoxypyridine was added and the solution refluxed for 16 h. After cooling to room temperature, the mixture was poured into 1M HCl and washed with toluene (3×). The aqueous layer was basified with 1M NaOH and extracted with toluene (1×) and ethyl acetate (1×). The combined organic layers were dried (magnesium sulfate), filtered, and evaporated to give a yellow oil. Purification by flash silica gel chromatography with 9:1 chloroform:methanol gave 0.304 g (37%) of (7RS,9aSR)-7-hydroxymethyl-2-(6-methoxypyridin-2-yl)-2,3,4,6,7,8,9,9a-octahydro-1H-pyrido[1,2-a]pyrazine.

A solution of 0.30 g (1.1 mmol) of (7RS,9aSR)-7-hydroxymethyl-2-(6-methoxypyridin-2-yl)-2,3,4,6,7,8,9,9a-octahydro-1H-pyrido[1,2-a]pyrazine, 0.182 g (1.62 mmol) of 4-fluorophenol, and 0.340 g (1.30 mmol) of triphenylphosphine, and 0.205 g (1.30 mmol) of diethylazodicarboxylate in 20 mL of THF was stirred at room temperature for 16 h. The solvent was evaporated, the residue dissolved in ether and extracted with 1M HCl (2×). The combined aqueous layers were basified with conc. ammonium hydroxide and extracted with ethyl acetate (3×). The combined organic layers were dried (magnesium sulfate), filtered and evaporated. Purification by flash silica gel chromatography with 50:50 ethyl acetate:hexane gave 0.300 g (75%) of yellow crystals. mp (.HCl) 228°–230° C. HRMS calcd for $C_{21}H_{26}FN_3O_2$: 371.2009, found: 371.2001.

EXAMPLE 28
(7RS,9aSR)-7-(4-Fluorophenoxy)methyl-2,3,4,6,7,8,9,9a-octahydro-2-(5-fluoropyridin-2-yl)-1H-pyrido[1,2-a]pyrazine

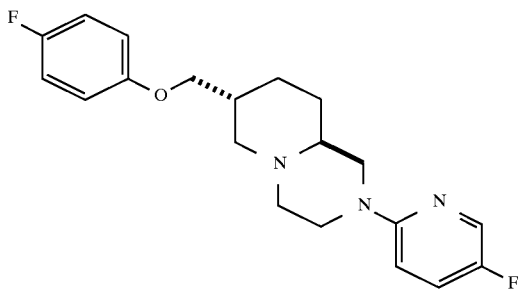

According to the procedure reported by Schwartz (*J. Am. Chem. Soc.* 1986, 108, 2445), a solution of 0.300 g (0.714 mmol) of (7RS ,9aS R)-7-(4-fluorophenoxy)methyl-(5-bromopyridin-2-yl)-2,3,4,6,7,8,9,9a-octahydro-1H-pyrido[1,2-a]pyrazine (Example 16) in 6.5 mL of THF:hexane::ethyl ether (4:1:1) under nitrogen was cooled to –100° C. n-Butyl lithium (0.57 mL, 2.5M in hexane) was added dropwise and the mixture stirred for 15 min. N-Fluorodibenzenesulfonamide (0.34 g, 1.07 mmol) in ethyl ether was added, the solution stirred for 20 min, and then allowed to warm to room temperature over 20 h. Water was added and the mixture extracted with ethyl acetate (3×), dried (magnesium sulfate), filtered and evaporated. Purification by flash silica gel chromatography with 50:50 ethyl acetate:hexane gave 0.038 g (15%) of the title compound. mp (.HCl) 214°–215° C. HRMS calcd for $C_{20}H_{23}F_2N_3O$: 359.1809, found: 359.1795.

EXAMPLE 29
(7RS,9aSR)-7-Phenoxymethyl-2-(2-chloropyrimidin-4-yl)-2,3,4,6,7,8,9,9a-octahydro-1H-pyrido[1,2-a]pyrazine

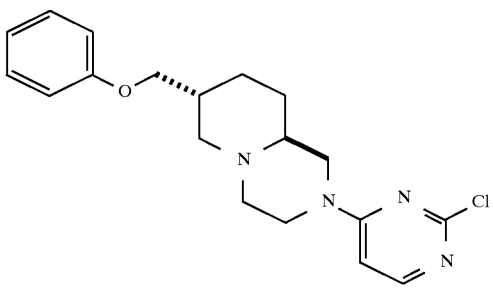

A mixture of (7RS,9aSR)-7-hydroxymethyl-2,3,4,6,7,8,9,9a-octahydro-1H-pyrido[1,2-a]pyrazine (U.S. Pat. No. 5,326,874) and 2,4-dichloropyrimidine were combined according to Preparation 3. The product from this reaction was coupled with phenol according to Example 1 to give the title compound. mp (.HCl) 227°–233° C. (dec). HRMS calcd for $C_{19}H_{23}ClN_4O$: 358.1560, found: 358.1560.

EXAMPLE 30
(7RS,9aSR)-7-Phenoxymethyl-2-(pyrazin-2-yl)-2,3,4,6,7,8,9,9a-octahydro-1H-pyrido[1,2-a]pyrazine

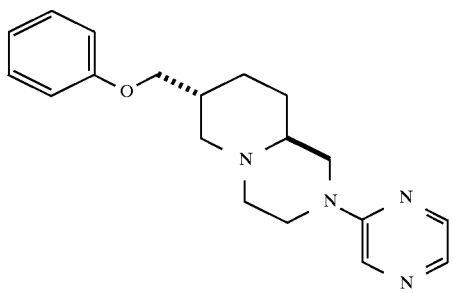

A mixture of (7RS,9aSR)-7-hydroxymethyl-2,3,4,6,7,8,9,9a-octahydro-1H-pyrido[1,2-a]pyrazine (U.S. Pat. No. 5,326,874) and 2-chloropyrazine were combined according to Preparation 3. The product from this reaction was coupled with phenol according to Example 1 to give the title compound. mp (.HCl) 217°–219° C. HRMS calcd for $C_{19}H_{24}N_4O$: 324.1945, found: 324.1981.

EXAMPLE 31
(7RS,9aSR)-7-Phenoxymethyl-2-(6-chloropyrazin-2-yl)-2,3,4,6,7,8,9,9a-octahydro-1H-pyrido[1,2-a]pyrazine

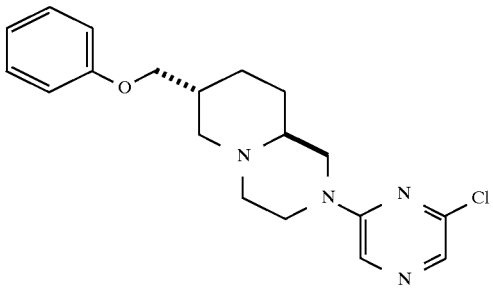

A mixture of (7RS,9aSR)-7-hydroxymethyl-2,3,4,6,7,8,9,9a-octahydro-1H-pyrido[1,2-a]pyrazine (U.S. Pat. No. 5,326,874) and 2,6-dichloropyrazine were combined according to Preparation 3. The product from this reaction was coupled with phenol according to Example 1 to give the title compound. mp (.HCl) 247° C. (dec). HRMS calc for $C_{19}H_{23}ClN_4O$: 358.1560, found: 358.160

EXAMPLE 32
(7RS9aSR)-7-(4-Fluorophenoxy)methyl-2-(6-chloropyridazin-3-yl)-2,3,4,6,7,8,9,9a-octahydro-1H-pyrido[1,2-a]pyrazine

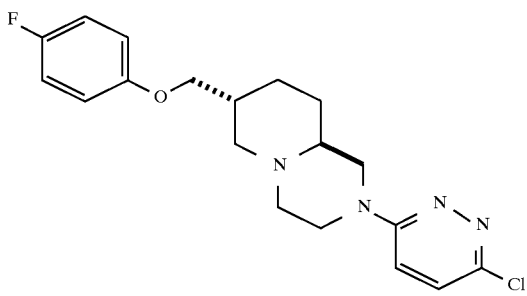

A mixture of (7RS,9aSR)-7-hydroxymethyl-2,3,4,6,7,8,9,9a-octahydro-1H-pyrido[1,2-a]pyrazine (U.S. Pat. No. 5,326,874) and 3,6-di-chloropyridazine were combined according to Preparation 3. The product from this reaction was coupled with 4-fluorophenol according to Example 1 to give the title compound. mp (.HCl) 255° C. (dec). HRMS calc for $C_{19}H_{22}ClFN_4O$; 376.1461, found: 376,1458.

EXAMPLE 33
(7RS,9aSR)-7-Phenoxymethyl-2-(6-chloropyridazin-3-yl)-2,3,4,6,7,8,9,9a-octahydro-1H-pyrido[1,2-a]pyrazine

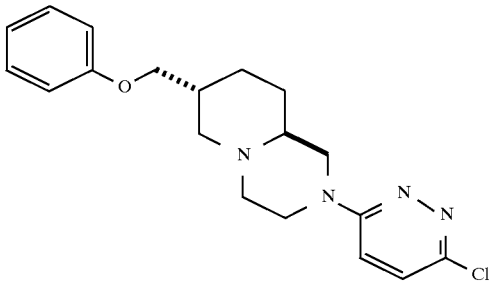

A mixture of (7RS,9aSR)-7-hydroxymethyl-2,3,4,6,7,8,9,9a-octahydro-1H-pyrido[1,2-a]pyrazine (U.S. Pat. No. 5,326,874) and 3,6-dichloropyridazine were combined according to Preparation 3. The product from this reaction was coupled with phenol according to Example 1 to give the title compound. mp (.HCl) >265° C. (dec) HRMS calcd for $C_{19}H_{23}ClN_4O$: 358.1555, found: 358.1550.

EXAMPLE 34
(7RS,9aSR)-7-Phenoxymethyl-2-(pyrimidin-4-yl)-2,3,4,6,7,8,9,9a-octahydro-1H-pyrido[1,2-a]pyrazine

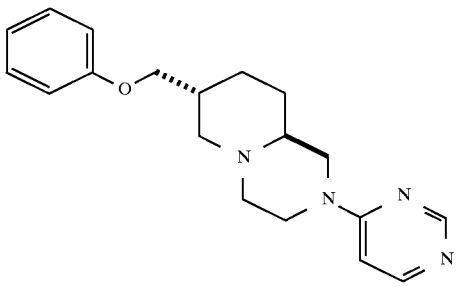

A mixture of 0.110 g (0.307 mmol) of (7RS,9aSR)-7-phenoxymethyl-2-(2-chloropyrimidin-4-yl)-2,3,4,6,7,8,9,9a-octahydro-1H-pyrido[1,2-a]pyrazine (Example 29), 20 mg of 10% Pd/C, and several drops of conc. hydrochloric acid in 30 mL of ethanol were shaken under 50 psi of hydrogen gas at room temperature for 6 h. The mixture was filtered through Celite and the filtrate was evaporated. The residue was basified with conc. ammonium hydroxide, extracted with chloroform, dried (magnesium sulfate), filtered and evaporated. Purification by flash silica gel chromatography with a solvent gradient from 100% chloroform to 95:5 chloroform:methanol gave 0.020 g (20%) of the title compound. mp (.HCl) >265° C. (dec). HRMS calc for $C_{19}H_{24}N_4O$: 324.1945, found: 324.1970.

EXAMPLE 35
(7RS,9aSR)-7-(4-Fluorophenoxy)methyl-2-(pyridazin-3-yl)-2,3,4,6,7,8,9,9a-octahydro-1H-pyrido[1,2-a]pyrazine

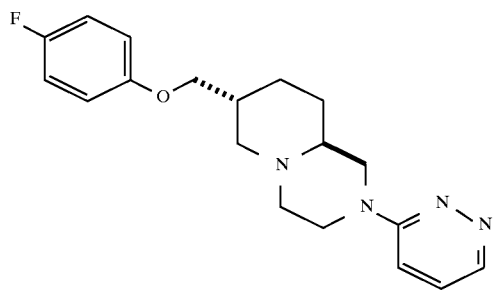

A mixture of 0.150 g (0.363 mmol) of (7RS,9aSR)-7-(4-fluorophenoxy)methyl-2-(6-chloropyridazin-3-yl)-2,3,4,6,7,8,9,9a-octahydro-1H-pyrido[1,2-a]pyrazine (Example 32) 0.10 mL (0.72 mmol) of triethylamine, and 20 mg of 10% Pd/C in 10 mL of ethanol were shaken under 50 psi of hydrogen for 18 h. The mixture was filtered through Celite and the filtrate was evaporated. The residue was dissolved in chloroform, washed with water, dried (magenesium sulfate), filtered and evaporated. mp (.HCl) 246°–250° C. HRMS calcd for $C_{19}H_{23}FN_4O$: 342.1851, found: 342.1,826.

EXAMPLE 36
(7R,9aS)-7-(3,5-Difluorophenoxy)methyl-2-(6-chloropyridazin-3-yl)-2,3,4,6,7,8,9,9a-octahydro-1H-pyrido[1,2-a]pyrazine

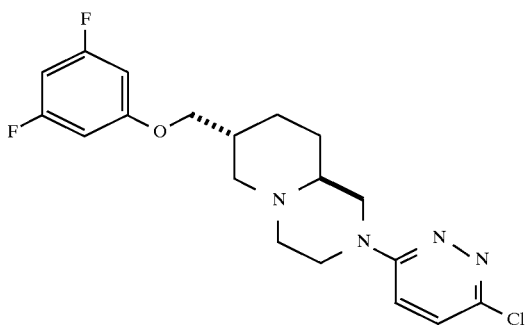

A mixture of (7R,9aS)-N-BOC-7-hydroxymethyl-2,3,4,6,7,8,9,9a-octahydro-1H-pyrido[1,2-a]pyrazine (WO 93/25552) and 3,5-difluorophenol were coupled followed by N-BOC deprotection according to Preparation 9. The product from this reaction was coupled with 3,6-dichloropyridazine according to Preparation 3 to give the title compound. mp (.HCl) 254°–259° C. $^{13}$C NMR (base, CDCl$_3$): δ 26.7, 28.9, 36.1, 45.1, 50.4, 54.3, 58.4, 60.3, 71.4, 96.3, 95.0, 98.4, 115.2, 128.8, 146.8, 158.8.

EXAMPLE 37
(7R,9aS)-7-Phenoxymethyl-2-(6-chloropyridin-3-yl)-2,3,4,6,7,8,9,9a-octahydro-1H-pyrido[1,2-a]pyrazine

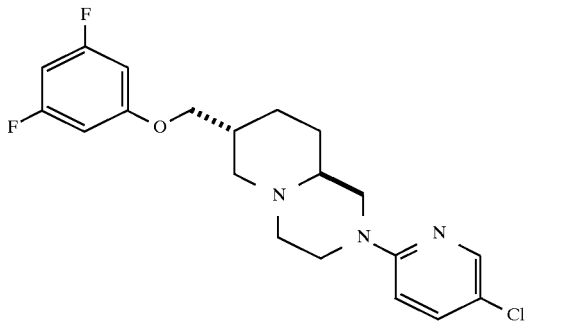

A mixture of (7R,9aS)-N-BOC-7-hydroxymethyl-2,3,4,6,7,8,9,9a-octahydro-1H-pyrido[1,2-a]pyrazine (WO 93/25552) and 3,5-difluorophenol were coupled followed by N-BOC deprotection according to Preparation 9. The product from this reaction was coupled with 2,5-dichloropyridine according to Preparation 11 to give the title compound. mp (.HCl) 260°–261° C. HRMS calcd for C$_{20}$H$_{22}$ClF$_2$N$_3$O: 393.1419, found: 393.1410.

EXAMPLE 38
3-[(7R,9aS)-2-Heteroaryl-2,3,4,6,7,8,9,9a-octahydro-1H-pyrido[1,2-a]pyrazin-7-ylmethyl]-3H-benzoxazol-2-ones

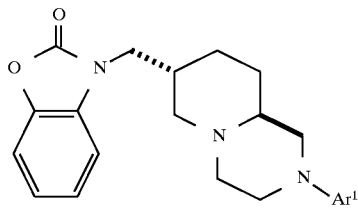

Compounds of the above formula were synthesized from 3-[(7R,9aS)-2,3,4,6,7,8,9,9a-octahydro-1H-pyrido[1,2-a]-pyrazin-7-ylmethyl]-3H-benzooxazol-2-one (Preparation 12) and the appropriate heteroaryl chloride according to Preparation 5. Purification was generally accomplished by flash silica gel chromatography using mixtures of ethyl acetate and hexane or mixtures of chloroform and methanol as the eluting solvent. The 2-substituent, melting point of the monohydrochloride and high resolution mass spectral data are shown.

Example 38a 2-(Pyrimidin-2-yl); mp 165°–167° C.; HRMS calcd for C$_{20}$H$_{23}$N$_5$O$_2$: 365.1852, found: 365.1850.

Example 38b 2-(5-Fluoropyrimidin-2-yl); mp 170°–171° C.; HRMS calcd for C$_{20}$H$_{22}$FN$_5$O$_2$: 383.1758, found: 383.1809.

Example 38c

2-(6-Chloropyridazin-3-yl); mp 176° C. (dec); HRMS calcd for C$_{20}$H$_{22}$ClN$_5$O$_2$: 399.1457, found: 399.1519.

EXAMPLE 39
3-[(7R,9aS)-2-(5-Chloropyridin-2-yl)-2,3,4,6,7,8,9,9a-octahydro-1H-pyrido[1,2-a]-pyrazin-7-ylmethyl]-3H-benzoxazol-2-one

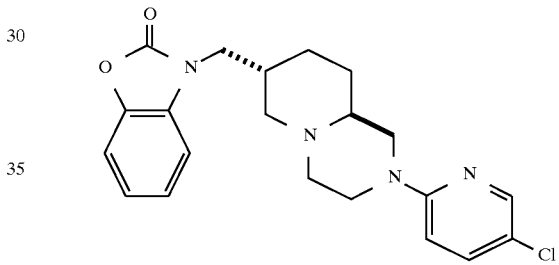

The title compound was synthesized according to Preparation 11 from 3-[(7R,9aS)-2,3,4,6,7,8,9,9a-octahydro-1H-pyrido[1,2-a]-pyrazin-7-ylmethyl]-3H-benzoxazol-2-one (Preparation 12) and 2,5-dichloropyridine. mp (.HCl) 247°–248° C. HRMS calcd for C$_{21}$H$_{23}$ClN$_4$O$_2$: 398.1510, found: 398.1484.

EXAMPLE 40
(7RS,9aSR)-7-(5-Fluoroindol-1-ylmethyl)-2-(pyrimidin-2-yl)-2,3,4,6,7,8,9,9a-octahydro-1H-pyrido[1,2-a]pyrazine

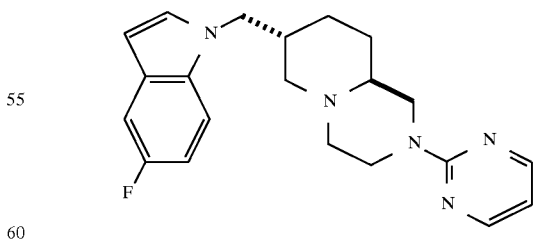

The title compound was synthesized according to Example 9 from (7RS,9aSR)-7-hydroxymethyl-2-(pyrimidin-2-yl)-2,3,4,6,7,8,9,9a-octahydro-1H-pyrido[1,2-a]pyrazine (Preparation 3) and 5-fluoroindole. mp (.HCl) 70°–72° C. HRMS calcd for C$_{21}$H$_{25}$FN$_5$(MH+): 366.2094, found: 366.2104.

EXAMPLE 41

(7RS,9aSR)-7-(4-Fluorophenylsulfanyl)methyl-2-(pyrimidin-2-yl)-2,3,4,6,7,8,9,9a-octahydro-1H-pyrido[1,2-a]pyrazine

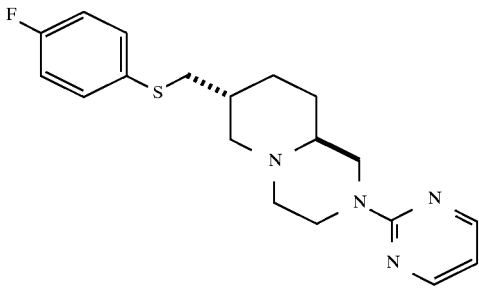

The title compound was prepared according to Example 1 from (7RS,9aSR)-7-hydroxymethyl-2-(2-pyrimidin-2-yl)-2,3,4,6,7,8,9,9a-octahydro-1H-pyrido[1,2-a]pyrazine (Preparation 3) and 4-fluorothiophenol mp (.HCl) 99°–101° C. HRMS calcd for $C_{19}H_{23}FN_4S$: 358.1627, found: 358.1683.

EXAMPLE 42

(7RS,9aSR)-7-(4-Fluorophenylsulfonyl)methyl-2-(pyrimidin-2-yl)-2,3,4,6,7,8,9,9a-octahydro-1H-pyrido[1,2-a]pyrazine

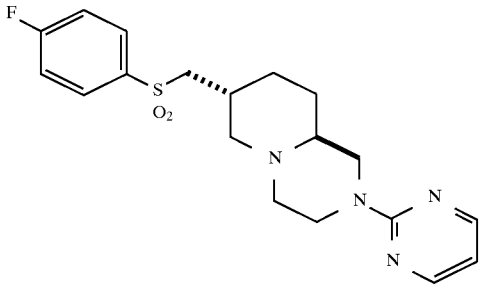

A solution of 0.50 g (1.40 mmol) of (7RS,9aSR)-7-(4-fluorophenylsulfanyl)methyl-2-(pyrimidin-2-yl)-2,3,4,6,7,8,9,9a-octahydro-1H-pyrido[1,2-a]pyrazine (Example 41) and 1.13 g (5.59 mmol) of 3-chloroperbenzoic acid in 30 mL of chloroform was stirred at room temperature for 20 h. The solution was partitioned with 1M sodium hydroxide, the layers were separated, the organic phase was dried (magnesium sulfate), filtered and evaporated. Purification by flash silica gel chromatography with 67:33 chloroform:methanol gave 0.18 g (33%) of the title compound. mp (.HCl) 155°–157° C. HRMS calcd for $C_{19}H_{23}FN_4O_2S$: 390.1526, found: 390.1483.

EXAMPLE 43

(7R,9aS)-7-(5-Fluoroindol-1-yl)methyl-2-(5-fluoropyrimidin-2-yl)-2,3,4,6,7,8,9,9a-octahydro-1H-pyrido[1,2-a]pyrazine

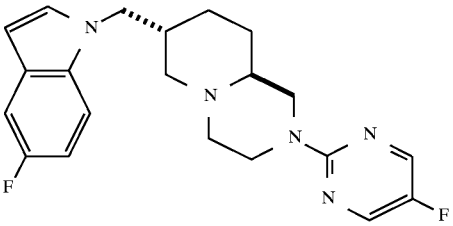

A solution of 6.0 g (22 mmol) of (7R,9aS)-2-BOC-7-hydroxymethyl-2,3,4,6,7,8,9,9a-octahydro-1H-pyrido[1,2-a]pyrazine (WO 93/25552) and 3.41 mL (24.4 mmol) of triethylamine in 225 mL of dry methylene chloride was chilled to 0° C., and treated with 1.80 mL (23.3 mmol) of methansulfonyl chloride in 75 mL of methylene chloride. After stirring 1 h, water was added and the pH adjusted to 12 with 15% sodium hydroxide. The layers were separated and the aqueous phase extracted with methylene chloride. The combined organic phase was dried (magnesium sulfate), filtered and evaporated to give 7.73 g (100%) of (7R,9aS)-2-BOC-7-(methanesulfonyloxy)methyl-2,3,4,6,7,8,9,9a-octahydro-1H-pyrido[1,2-a]pyrazine.

A solution of 8.41 g (62 mmol) of 5-fluoroindole in 250 mL of DMF was treated with 2.46 g (62 mmol) of sodium hydride (60% oil dispersion) and the mixture stirred at 50° C. for 1.5 h. Heating was stopped temporarily, 7.73 g (22.2 mmol) of (7R,9aS)-2-BOC- 7-(methanesulfonyloxy)methyl-2,3,4,6,7,8,9,9a-octahydro-1H-pyrido[1,2-a]pyrazine in 250 mL of DMF was added, and the mixture stirred at 100° C. for 2 h. The mixture was cooled to room temperature, diluted with water, acidified to pH 2 with 6M hydrochloric acid, and washed with ethyl acetate. The aqueous phase was basified to pH 12 with conc. ammonium hydroxide and extracted with ethyl acetate (3×). The combined organic phase was dried (magnesium sulfate), filtered and evaporated. Purification by flash silica gel chromatography with ethyl acetate gave 3.09 g (36%) of (7R,9aS)-2-BOC-7-(5-fluoroindol-1-yl)methyl-2,3,4,6,7,8,9,9a-octahydro-1H-pyrido[1,2-a]pyrazine.

A solution of 3.0 g (7.75 mmol) of (7R,9aS)-2-BOC-7-(5-fluoroindol-1-yl)methyl-2,3,4,6,7,8,9,9a-octahydro-1H-pyrido[1,2-a]pyrazine in 200 mL of 70:30 trifluoroacetic acid:water was stirred at room temperature for 1 h. The mixture was concentrated in vacuo, basified with 15% sodium hydroxide and extracted with ethyl acetate (2×). The combined organics were dried (magnesium sulfate), filtered and evaporated to give 2.0 g (90%) of (7R,9aS)-7-(5-fluoroindol-1-yl)methyl-2,3,4,6,7,8,9,9a-octahydro-1H-pyrido-[1,2-a]pyrazine.

A mixture of 2.20 g (7.67 mmol) of (7R,9aS)-7-(5-fluoroindol-1-yl)methyl-2,3,4,6,7,8,9,9a-octahydro-1H-pyrido[1,2-a]pyrazine, 1.02 g (7.67 mmol) of 2-chloro-5-fluoropyrimidine and 1.95 g (18.4 mmol) of sodium carbonate in 100 mL of water was stirred at 95° C. for 72 h. The mixture was cooled to room temperature, extracted with chloroform (3×), the combined organic phase was washed with brine, dried (magnesium sulfate), filtered and evaporated. Purification by flash silica gel chromatography with 50:50 ethyl acetate:hexane gave 1.17 g (40%) of the title compound. mp (.HCl) 180°–182° C. HRMS calc for HRMS calcd for $C_{21}H_{23}F_2N_5$: 383.1922, found: 383.1924.

EXAMPLE 44

1-[(7R,9aS)-2-(Pyrimidin-2-yl)-2,3,4,6,7,8,9,9a-octahydro-1H-pyrido[1,2-a]pyrazin-7-ylmethyl]-1,3-dihydro-indol-2-one

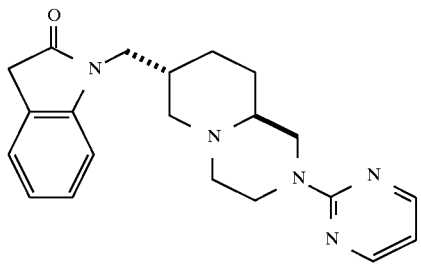

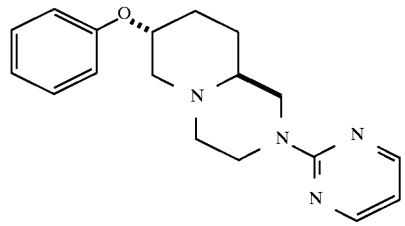

A solution of 6.0 g (22 mmol) of (7R,9aS)-2-BOC-7-hydroxymethyl-2,3,4,6,7,8,9,9a-octahydro-1H-pyrido[1,2-a]pyrazine (WO 93/25552) and 3.41 mL (24.4 mmol) of triethylamine in 225 mL of dry methylene chloride was chilled to 0° C., and treated with 1.80 mL (23.3 mmol) of methanesulfonyl chloride in 75 mL of methylene chloride. After stirring 1 h, water was added and the pH adjusted to 12 with 15% sodium hydroxide. The layers were separated and the aqueous phase extracted with methylene chloride. The combined organic phase was dried (magnesium sulfate), filtered and evaporated to give 7.73 g (100%) of (7R,9aS)-2-BOC-7 -(methanesulfonyloxy)methyl-2,3,4,6,7,8,9,9a-octahydro-1H-pyrido[1,2-a]pyrazine.

A solution of 2.75 g (10.7 mmol) of oxindole in 85 mL of DMF was treated with 0.82 g (21 mmol) of sodium hydride (60% oil dispersion) and the mixture stirred at 50° C. for 1.5 h. Heating was stopped temporarily, 2.56 g (7.38 mmol) of (7R,9aS)-2-BOC-7-(methanesulfonyloxy)methyl-2,3,4,6,7,8,9,9a-octahydro-1H-pyrido[1,2-a]pyrazine in 85 mL of DMF was added, and the mixture stirred at 100° C. for 2 h. The mixture was cooled to room temperature, diluted with water, acidified to pH 2 with 6M hydrochloric acid, and washed with ethyl acetate. The aqueous phase was basified to pH 12 with conc. ammonium hydroxide and extracted with ethyl acetate (3×). The combined organic phase was dried (magnesium sulfate), filtered and evaporated. Purification by flash silica gel chromatography with ethyl acetate gave 0.677 g (24%) of 1-[(7R,9aS)-2-BOC-2,3,4,6,7,8,9,9a-octahydro-1H-pyrido-[1,2-a]pyrazin-7-ylmethyl)]-1,3-dihydro-indol-2-one.

A solution of 0.53 g (1.38 mmol) of 1-[(7R,9aS)-2-BOC-2,3,4,6,7,8,9,9a-octahydro-1H-pyrido[1,2-a]pyrazin-7-ylmethyl]-1,3-dihydro-indol-2-one in 10 mL of chloroform was treated with excess HCl(g) in ethyl ether and stirred at room temperature for 1 h. The solvent was evaporated to give 0.49 g (100%) of 1-[(7R,9aS)-2,3,4,6,7,8,9,9a-octahydro-1H-pyrido[1,2-a]pyrazin-7-ylmethyl]-1,3-dihydro-indol-2-one dihydrochloride.

A mixture of 0.49 g (1.38 mmol) of 1-[(7R,9aS)-2,3,4,6,7,8,-9,9a-octahydro-1H-pyrido[1,2-a]pyrazin-7-ylmethyl]-1,3-dihydro-indol-2-one dihydrochloride, 0.157 g (1.37 mmol) of 2-chloropyrimidine and 0.64 g (6.02 mmol) of sodium carbonate in 20 15 mL of water was stirred at 95° C. for 16 h. The mixture was cooled to room temperature, extracted with chloroform (3×), the combined organic phase was washed with brine, dried (magnesium sulfate), filtered and evaporated. Purification by flash silica gel chromatography with 95:5 ethyl acetate:methanol gave 0.181 g (30%) of the title compound. mp (.HCl) 174°–176° C. HRMS calcd for $C_{21}H_{25}N_5O$: 363.2059, found: 363.2032.

EXAMPLE 45

(7RS,9aSR)-7-Phenoxy-2-(pyrimidin-2-yl)-2,3,4,6,7,8,9,9a-octahydro-1H-pyrido[1,2-a]pyrazine A solution of 0.600 g (3.03 mmol) of (9aSR)-7-(ethylenedioxy)-2,3,4,6,7,8,9,9a-octahydro-1H-pyrido[1,2-a]pyrazine (Compernolle, F.; Slaeh, M. A.; Toppet, S.; Hoornaert, G. J. Org. Chem., 1991, 56, 5192), 0.35 g (3.0 mmol) of 2-chloropyrimidine and 0.77 g (7.3 mmol) of sodium carbonate in 6 mL of water was refluxed for 21 h. The mixture was cooled to room temperature, extracted with methylene chloride (3×), the combined organic phase was washed with water and brine, dried (magnesium sulfate), filtered and evaporated. Purification by filtration through a 30 g plug of flash silica gel with 95:5 ethyl acetate:ethanol gave 0.624 g (75%) of (9aSR)-7-(ethylenedioxy-2-(pyrimidin-2-yl)-2,3,4,6,7,8,9,9a-octahydro-1H-pyrido[1,2-a]pyrazine. mp (base) 121°–122° C. Anal calcd for $C_{14}H_{20}N_4O_2$: C, 60.85; H, 7.29; N, 20.27; found: C, 60.84; H, 7.26; N, 20.42.

A solution of 0.60 g (2.2 mmol) of (9aSR)-7-(ethylenedioxy)-2-(pyrimidin-2-yl)-2,3,4,6,7,8,9,9a-octahydro-1H-pyrido[1,2-a]pyrimidine was dissolved in 8 mL of 6M HCl and refluxed for 3 h. The solution was cooled to room temperature, the solvent was evaporated, the residue dissolved in methylene chloride, mixed with aqueous potassium carbonate, the layers were separated, and the aqueous layer extracted with methylene chloride (2×). The combined organic phase was dried (magnesium sulfate), filtered and evaporated. Filtration through a plug of flash silica gel with 95:5 ethyl acetate:ethanol gave 0.205 g (41%) of 7-keto derivative. The 7-keto derivative was dissolved in 10 mL of methanol and treated with 0.33 g (0.88 mmol) of 10% sodium borohydride on alumina. After stirring for 1 h, the mixture was filtered and evaporated to give 0.156 g (75%) of crude 7-hydroxy derivative. The crude 7-hydroxy derivative, 0.094 g (1.0 mmol) of phenol, and 0.209 g (0.799 mmol) of triphenylphosphine were dissolved in 1.4 mL of dry THF. The mixture was treated with 0.13 mL (0.80 mmol) of diethyl azodicarboxylate and stirred at room temperature for 24 h. The mixture was diluted with ethyl ether, extracted with 0.1M HCl(3×), the combined aqueous phase was washed with ethyl ether (2×), basified with conc. ammonium hydroxide, and extracted with ethyl acetate (3×). The combined ethyl acetate layers were dried (magnesium sulfate), filtered and evaporated. Purification by flash silica gel chromatography with 50:50 ethyl acetate:hexane gave 0.036 g (17%) of the title compound. mp (base) 147°–148° C. HRMS calcd for $C_{18}H_{22}N_4O$: 310.1794, found: 310.1819.

EXAMPLE 46

(4-Fluoro)phenyl-[(7RS,9aSR)-2-(pyrimidin-2-yl)-2,3,4,6,7,8,9,9a-octahydro-1H-pyrido[1.2-a]pyrazin-7-yl]-methanol

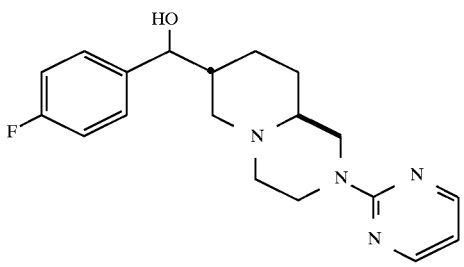

A flame-dried 3-neck flask was attached to a bleach trap and charged with 20 mL of methylene chloride and 0.77 mL (1.1 mmol) of oxalyl chloride. The solution was chilled to −78° C. and anhydrous DMSO (1.38 mL, 1.93 mmol) was added dropwise at a rate which kept the internal temperature at or below ×50° C. A methylene chloride solution of (7RS,9aSR)-7-hydroxymethyl-2-(pyrimidin-2-yl)-2,3,4,6,7,8,9,9a-octahydro-1H-pyrido[1,2-a]pyrazine (2.5 g, 9.1 mmol) was added followed by slow addition of 5.2 mL (37 mmol) of triethylamine. After warming to room temperature, 40 mL of water was added, the layers were separated and the aqueous phase extracted with methylene chloride (4×). The combined organic phase was dried (sodium sulfate), filtered and evaporated to give 2.24 g (90%) of aldehyde. $^{13}$C NMR (CDCl$_3$): δ 24.0, 28.5, 43.5, 48.8, 49.0, 55.4, 54.7, 60.3, 109.9, 157.7, 161.3, 202.3. HRMS calcd for $C_{13}H_{18}N_4O$: 246.1481, found: 246.1484.

A solution of the crude aldehyde. (0.44 g, 1.6 mmol) in 45 mL of dry THF was chilled to ×10° C. and treated with 8.8 mL (18 mmol, 2M in THF) of 4-fluorophenyl magnesium bromide. The solution was allowed to warm to room temperature and 10 mL of ice water was added carefully followed by 100 mL of saturated ammonium chloride. The aqueous phase was extracted with ethyl ether (1×), dried (sodium sulfate), filtered and evaporated. Purification by flash silica gel chromatography with methylene chloride:methanol:conc. ammonium hydroxide 12:1:0.04 gave 0.037 g (6.7%) of the title compound. $^{13}$C NMR (CDCl$_3$): δ 26.1, 28.8, 43.2, 43.3, 46.1, 48.8, 54.8, 57.8, 58.0, 60.9, 76.4, 109.9, 115.09, 115.38, 127.98, 128.09, 138.7, 157.7, 160.6, 161.4, 163.4. HRMS calcd for $C_{19}H_{24}FN_4O$ (MH+): 343.1934, found: 343.1938.

EXAMPLE 47

(4-Fluoro)phenyl-[(7SR,9aSR)-2-(pyrimidin-2-yl)-2,3,4,6,7,8,9,9a-octahydro-1H-pyrido[1,2-a]pyrazin-7-yl]-methanol

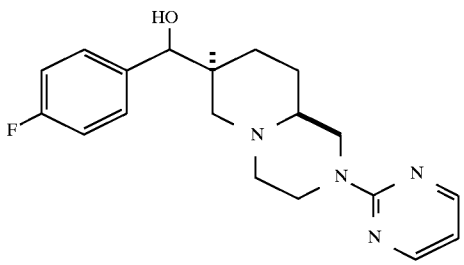

The title compound was prepared according to Example 46 starting with (7SR,9aSR)-7-hydroxymethyl-2-(pyrimidin-2-yl)-2,3,4,6,7,8,9,9a-octahydro-1H-pyrido[1,2-a]pyrazine. HRMS calcd for $C_{19}H_{24}FN_4O$ (MH+): 343.1934, found: 343.1934.

EXAMPLE 48

(4-Fluoro)phenyl-[(7RS,9aSR)-2-(pyrimidin-2-yl)-2,3,4,6,7,8,9,9a-octahydro-1H-pyrido[1,2-a]pyrazin-7-yl]-methanone

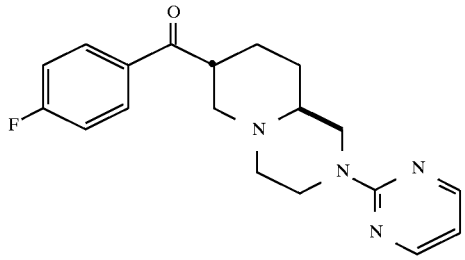

The title compound was prepared according to the oxalyl chloride/DMSO oxidation step of Example 46 starting with (4-fluoro)phenyl-[(7RS,9aSR)-2-(pyrimidin-2-yl)-2,3,4,6,7,8,9,9a-octahydro-1H-pyrido[1,2-a]pyrazin-7-yl]-methanol (Example 46). $^{13}$CNMR (CDCl$_3$): δ 27.3, 28.3, 48.6, 54.1, 56.7, 59.9, 110.1, 115.77, 116.05, 131.20, 131.32, 132.4, 158.0, 161.1, 163.4, 166.7. HRMS calcd for $C_{19}H_{21}FN_4O$: 340.1699, found: 340.1539.

EXAMPLE 49

(7S,9aS)-7-(4-Fluorophenoxy)methyl-2-(5-fluoropyrimidin-2-yl)-2,3,4,6,7,8,9,9a-octahydro-1H-pyrido[1,2-a]pyrazine

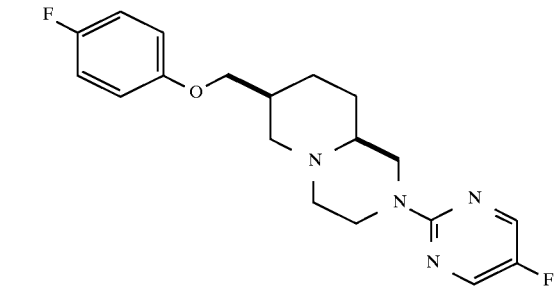

A solution of 0.82 g (3.08 mmol) of (7S,9aS)-7-hydroxymethyl-2-(5-fluoropyrimidin-2-yl)-2,3,4,6,7,8,9,9a-octahydro-1H-pyrido[1,2-a]pyrazine (Preparation 13), 0.52 g (4.62 mmol) of 4-fluorophenol, 0.97 g (3.70 mmol) of triphenylphosphine in dry THF was treated with 0.64 g (3.70 mmol) of diethyl azodicarboxylate and stirred at room temperature for 72 h. The solvent was evaportated, the residue dissolved in 50:50 ethyl acetate:ethyl ether, and treated with HCl(g) in ethyl ether until precipitation ceased. The solid was collected by filtration, dissolved in chloroform, 1M sodium hydroxide was added, and the layers were separated. The organic layer was dried (magnesium sulfate), filtered and evaporated. Purification by flash silica gel chromatography with 90:10 hexane:ethyl acetate gave 0.49 g (44%) of the title compound. mp (.HCl) 225°–228° C. $^{13}$C NMR (base, CDCl$_3$): δ 24.8, 25.2, 33.8, 44.3, 49.7, 54.8, 56.6, 61.0, 69.5, 115.48, 115.53, 115.59, 115.83, 144.97, 145.26, 149.85, 153.15, 155.42, 155.54, 158.69, 158.74. HRMS calcd for $C_{19}H_{22}F_2N_4O$: 360.1762, found: 360.1752.

EXAMPLE 50

(7RS,9aSR)-7-(5-Fluoro-1H-indol-3-yl)methyl-2-(pyrimidin-2-yl)-2,3,4,6,7,8,9,9a-octahydro-1H-pyrido[1,2-a]pyrazine

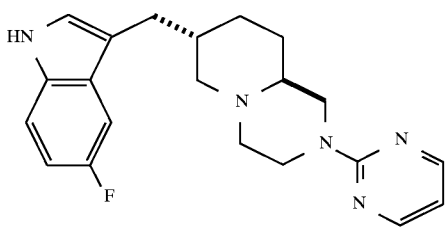

A solution of 2.22 g (8.1 mmol) of f7RS,9aSR)-7-hydroxymethyl-2-(2-pyrimidinyl)-2,3,4,6,7,8,9,9a-octahydro-1H-pyrido[1,2-a]pyrazine (Preparation 3) and triethyl amine (1.34 mL, 9.7 mmol) in 15 mL of methylene chloride was chilled to 0° C. and treated with a solution of 0.64 mL (8.3 mmol) of methanesulfonyl chloride in 7 mL of methylene chloride. The solution was stirred at 0° C. for 1 h, and then allowed to warm to room temperature. Water was added (30 mL), and the pH adjusted to 9.5 with 2M sodium hydroxide. The layers were separated and the aqueous phase extracted with methylene chlorde (30 mL). The combined organic phase was dried (sodium sulfate), filtered and evaporated to give 2.05 g (78%) of mesylate.

A flame-dried flask was charged with 0.2 g (1.5 mmol) of 5-fluoroindole, 8 mL of benzene and 0.49 mL (1.5 mmol) of ethyl magenesium bromide (3M in THF). Under vigorous stirring, the above mesylate (0.53 g, 1.6 mmol) was added and the mixture stirred at room temperature for 18 h. Water (15 mL), ethyl acetate (10 mL) and sat. sodium bicarbonate were added, and the layers were separated. The organic phase was dried (sodium sulfate), filtered and evaporated. Initial purification by flash silica gel chromatography with ethyl acetate:methanol 95:5 followed a second purification by flash silica gel chromatography with 30:70:2 ethyl acetate:hexane:methanol gave 80 mg of the title compound. $^{13}$C NMR (CDCl$_3$): δ 29.5, 30.2, 30.8, 37.1, 43.6, 49.1, 54.8, 60.9, 103.8, 104.1, 109.0, 109.4, 109.8, 110.7, 110.9, 114.4, 114.5, 123.7, 132.8, 156.1, 157.7, 159.2, 161.5. HRMS calcd for $C_{21}H_{24}FN_5$: 365.2011, found: 365.1985.

EXAMPLE 51

(7RS,9aSR)-7-(5-Fluoro-1-methyl-1H-indol-3-yl)methyl-2-(pyrimidin-2-yl)-2,3,4,6,7,8,9,9a-octahydro-1H-pyrido[1,2-a]pyrazine

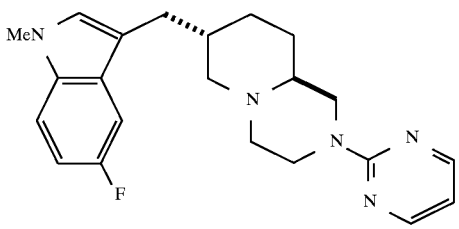

A flame-dried flask was charged with 0.103 g (0.28 mmol) of (7RS,9aSR)-7-(5-fluoro-1H-indol-3-yl)methyl-2-(pyrimidin-2-yl)-2,3,4,6,7,8,9,9a-octahydro-1H-pyrido[1,2-a]pyrazine (Example 50), anhydrous DMF (1 mL) and 12 mg (0.30 mmol) of sodium hydride (60% oil dispersion). The suspension was treated with 0.019 mL (0.31 mmol) of methyl iodide and the mixture was heated at 50° C. for 16 h. The mixture was cooled to room temperature, concentrated in vacuo, and diluted with methylene chloride (25 mL) and water (25 mL), and the layers were separated. The organic phase was dried (sodium sulfate), filtered and evaporated to a solid residue. The solid was washed with ethyl acetate (2×), the ethyl acetate was evaporated to give 50 mg of the title compound. $^1$H NMR (CDCl$_3$): δ 1.00–1.31 (m, 3H), 1.64–2.23 (m, 6H), 2.54–3.1 (m, 5H), 3.69 (s, 3H), 4.51–4.56 (m, 2H), 6.43 (dd, J=1 Hz, 1H), 6.83 (s, 1H), 6.93 (m, 1H), 7.15 (m, 2H), 8.27 (d, J=1 Hz, 2H). TLC R$_f$: 0.81 (90:10:1 methylene chloride:methanol:ammonium hydroxide).

EXAMPLE 52

(7RS,9aSR)-7-(5-Chloro- and -(6-Chloro-2-methyl-benzoimidazol-1-yl)methyl-2-(pyrimidin-2-yl)-2,3,4,6,7,8,9,9a-octahydro-1H-pyrido[1,2-a]pyrazine

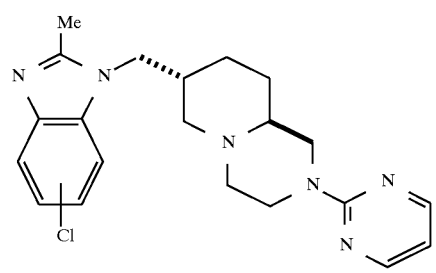

A solution of 2.22 g (8.1 mmol) of (7RS,9aSR)-7-hydroxymethyl-2-(pyrimidin-2-yl)-2,3,4,6,7,8,9,9a-octahydro-1H-pyrido[1,2-a]pyrazine (Preparation 3) and triethyl amine (1.34 mL, 9.7 mmol) in 15 mL of methylene chloride was chilled to 0° C. and treated with a solution of 0.64 mL (8.3 mmol) of methanesulfonyl chloride in 7 mL of methylene chloride. The solution was stirred at 0° C. for 1 h, and then allowed to warm to room temperature. Water was added (30 mL), and the pH adjusted to 9.5 with 2M sodium hydroxide. The layers were separated and the aqueous phase extracted with methylene chlorde (30 mL). The combined organic phase was dried (sodium sulfate), filtered and evaporated to give 2.05 g (78%) of mesylate.

A flame-dried flask was charged with 0.11 g (0.67 mmol) of 5-chloro-2-methylbenzimidazole, 3 mL of dry DMF, and 29 mg (0.74 mmol) of sodium hydride (60% oil dispersion). The solution heated at 50° C. for 30 min, and then cooled to room temperature. The above mesylate (0.20 g, 0.61 mmol) was added and the mixture was heated at 100° C. for 16 h. The mixture was cooled to room temperature, and concentrated in vacuo. Ethyl acetate (30 mL) and water (30 mL) were added, the layers were separated, and the organic phase was dried (sodium sulfate), filtered and evaporated. Purification by flash silica gel chromatography with ethyl acetate gave 130 mg of a mixture of the title compounds. $^1$H NMR (CDCl$_3$): δ 1.2 (m, 2H), 1.9 (m, 5H), 2.2 (m,2H), 2.5 (s, 3H), 2.75 (m, 2H), 2.95 (m, 1H), 3.85 (m, 2H), 4.55 (m, 2H), 6.45 (dd, J=1 Hz, 1H), 7.1 (s, 1H), 7.2 (m, 1H), 7.4 (m, 1H), 8.25 (d, J=1 Hz, 2H). TLC R$_f$: 0.32 (90:10 methylene chloride:methanol). HRMS calcd for $C_{21}H_{25}ClN_6$: 396.1829, found: 396.1809.

EXAMPLE 53

1-(4-Fluorophenyl)-2-[(7RS,9aSR)-2-(pyrimidin-2-yl)-2,3,4,6,7,8,9,9a-octahydro-1H-pyrido[1,2-a]pyrazin-7-yl]-ethanol

53

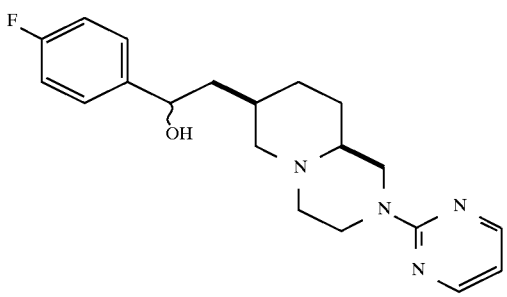

A solution of 2.2 g (8.1 mmol) of (7RS,9aSR)-7-hydroxymethyl-2-(pyrimidin-2-yl)-2,3,4,6,7,8,9,9a-octahydro-1H-pyrido[1,2-a]pyrazine and 1.3 mL (9.7 mmol) of triethylamine in 15 mL of methylene chloride at 0° C. was treated with a solution of 0.64 mL (8.3 mmol) of methanesulfonyl chloride in 7 mL of methylene chloride, and the solution was stirred for 1 h. Water was added (30 mL) and the pH adjusted to 9.5 with 2M sodium hydroxide. The layers were separated, the aqueous phase was extracted with methylene chloride (30 mL), the combined organic phase was dried (sodium sulfate), filtered and evaporated to give 2.05 g (78%) of mesylate.

The above mesylate (2.05 g, 6 mmol) was dissolved in 50 mL of dry DMF, 0.31 g (6 mmol) of sodium cyanide was added and the mixture heated at 110° C. under a nitrogen atmosphere for 16 h. The reaction was cooled to room temperature, 1 mL of saturated sodium carbonate solution was added. The solvent was removed in vacuo, the residue was taken up in ethyl acetate (100 mL) and water (50 mL), and the layers were separated. The organic layer was washed with sat. sodium carbonate (2×), dried (sodium sulfate), filtered and evaporated to give 1.4 g (91%) of nitrile. HRMS calcd for $C_{14}H_{19}N_5$: 257.1640, found: 257.1630.

A flame-dried flask containing 0.350 g (1.36 mmol) of the above nitrile was charged with 1.8 mL (1.8 mmol) of 1M diisobutylaluminum hydride. The solution was stirred for 2 h at room temperature, then stirred at 50° C. for 1 h. The reaction was cooled to room temperature, and 2M hydrochloric acid was added slowly until gas evolution ceased. The pH was adjusted to 8 with 2M sodium hydroxide, and the mixture was diluted with 50 mL of ethyl ether and 50 mL of water. The layers were separated, the organic phase was dried (sodium sulfate), filtered and evaporated. Purification by flash silica gel chromatography with 18:1:0.04 methylene chloride:methanol:conc. ammonium hydroxide gave 31 mg (9%) of aldehyde.

A flame-dried flask containing 30 mg (0.10 mmol) of the above aldehyde in 1 mL of dry THF was chilled to −10° C. and 0.075 mL (0.15 mmol) of 4-fluorophenyl magnesium bromide (2M in THF) was added. The reaction was allowed to warm to room temperature and stirred for 1 h. Water (1 mL), saturated ammonium chloride (1 mL) and ethyl ether (5 mL) were added, and the layers were separated. The organic phase was dried (sodium sulfate), filtered and evaporated. Purification by flash silica gel chromatography with 24:1:0.04 methylene chloride:methanol:conc. ammonium hydroxide gave 11 mg (39%) of the title compound. $^1$H NMR (CDCl$_3$): δ 0.97–1.05 (m, 1H), 1.23–1.61 (m, 2H), 1.64–1.86 (m 6H), 2.14–2.23 (m, 1H), 2.54–2.78 (m, 1H), 2.81–3.02 (m, 3H), 4.49–4.61 (m, 2H), 4.77–4.71 (m, 1H), 6.45 (t, J=1 Hz, 1H), 6.97–7.03 (m, 2H), 7.25–7.32 (m, 2H), 8.27 (d, J=1 Hz, 2H). HRMS calcd for $C_{20}H_{25}FN_4O$: 356.2012, found: 356.2009.

54

EXAMPLE 54

1-(4-Fluorophenyl)-2-[(7SR,9aSR)-2-(pyrimidin-2-yl)-2,3,4,6,7,8,9,9a-octahydro-1H-pyrido[1,2-a]pyrazin-7-yl]-ethanone

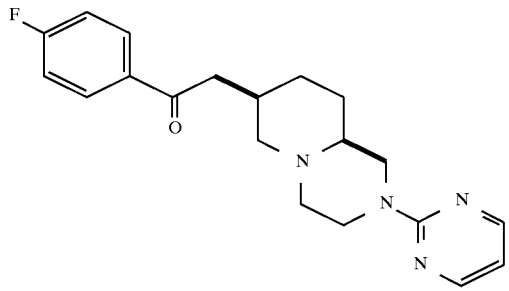

A solution of 38.1 g (117 mmol) of (7SR,9aSR)-7-(methanesulfonyloxy)methyl-2-(pyrimidin-2-yl)-2,3,4,6,7,8,9,9a-octahydro-1H-pyrido[1,2-a]pyrazine (prepared according to U.S. Pat. No. 5,122,525) and 6.01 g (122 mmol) of sodium cyanide in 500 mL of dry DMF was heated at 110° C. for 16 h. The mixture was cooled to room temperature, 10 mL of saturatic sodium bicarbonate was added and the mixture concentrated in vacuo. Water (1000 mL) and ethyl acetate (1000 mL) were added to the solid residue, the pH was adjusted to 11, and the layers were separated. The organic phase was washed with water (2×), dried (sodium sulfate), filtered and evaporated. Recrystalization from ethyl acetate-hexane gave 14.5 g of [(7SR,9aSR)-2-(pyrimidin-2-yl)-2,3,4,6,7,8,9,9a-octahydro-1H-pyrido[1,2-a]pyrazin-7-yl]acetonitrile. $^{13}$C NMR (CDCl$_3$): d 19.5, 24.1, 26.9, 31.3, 33.1, 43.6, 48.9, 54.5, 109.8, 119.8, 157.7, 161.4.

A solution of 0.200 g (0.78 mmol) of [(7SR,9aSR)-2-(pyrimidin-2-yl)-2,3,4,6,7,8,9,9a-octahydro-1H-pyrido[1,2-a]pyrazin-7-yl]acetonitrile in 4 mL of dry THF was treated with 4.3 mg (0.03 mmol) of cuprous bromide and 0.85 mL (0.85 mmol) of 4-fluorophenyl magnesium bromide (1M in THF), and the mixture was refluxed for 48 h. The mixture was cooled to room temperature, 0.75 mL of water was added carefully followed by 3.5 mL of 15% sulfuric acid. The mixture was refluxed for 24 h. The reaction was cooled to room temperature, and 10% sodium carbonate solution was added until gas evolution ceased. Ethyl ether (10 mL) was added, the layers were separated, and the aqueous phase was extracted with ethyl ether (2×10mL). The combined organics were dried (sodium sulfate), filtered and evaporated. Purification by flash silica gel chromatography with ethyl acetate:hexane:methanol:conc. ammonium hydroxide (1:1:0.01:0.01) gave 30 mg of the title compound. $^{13}$C NMR (CDCl$_3$): d 25.1, 28.3, 29.9, 40.2, 43.7, 49.1, 54.8, 59.1, 61.1, 109.7, 115.4, 115.7, 130.8, 130.9, 134.0, 157.7, 161.5, 164.0, 167.4. HRMS calcd for $C_{20}H_{23}FN_4O$: 354.1856, found: 354.1847.

EXAMPLE 55

(7S,9aS)-7-(Substituted-phenoxy)methyl-2-(5-fluoropyrimidin-2-yl)-2,3,4,6,7,8,9,9a-octahydro-1H-pyrido[1,2-a]pyrazines

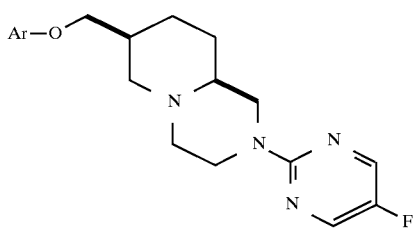

Compounds of the above formula were prepared according to Example 49 using (7S,9aS)-7-hydroxymethyl-2-(5-fluoropyrimidin-2-yl)-2,3,4,6,7,8,9,9a-octahydro-1H-pyrido[1,2-a]pyrazine (Preparation 13) and the appropriate phenol. Purification was generally accomplished with flash silica gel chromatography using mixtures of ethyl acetate and hexane as the eluting solvent. The stereochemical configuration, 7-(substituted-phenoxy)methyl substituent, melting point of the monohydrochloride salt, and HRMS data are shown.

Example 55a (7S,9aS)-7-(4-Fluoro-2-methyl-phenoxy)methyl; mp 237°–243° C.; HRMS calcd for $C_{20}H_{24}F_2N_4O$: 374.1913, found: 374.1874.

Example 55b (7S,9aS)-7-(3-Cyano-phenoxy)methyl-; mp 209°–211° C.; HRMS calcd for $C_{20}H_{23}FN_5O$ (MH+): 368.1887, found: 368.1884.

Example 55c (7S,9aS)-7-(3-(Carbomethoxy)methyl-phenoxy)methyl-; mp 158°–161° C.; HRMS calcd for $C_{22}H_{28}FN_4O_3$ (MH+): 415.2139, found: 415.2123.

EXAMPLE 56

(7S,9aS)-7-(Substituted-phenoxy)methyl-2-(5-fluoropyrimidin-2-yl)-2,3,4,6,7,8,9,9a-octahydro-1H-pyrido[1,2-a]pyrazines

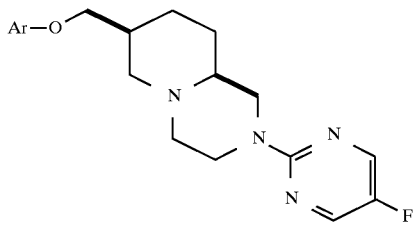

The following compounds were prepared according to Example 8 from (7S,9aS)-7-hydroxymethyl-2-(5-fluoropyrimidin-2-yl)-2,3,4,6,7,8,9,9a-octahydro-1H-pyrido[1,2-a]pyrazine (Preparation 13) and the appropriate phenol. Purification was generally accomplished by flash silica gel chromatography using mixtures of ethyl acetate and hexane or mixtures of chloroform and methanol as the eluting solvent. The stereochemical configuration, 7-(substituted-phenoxy)methyl substituent, melting point of the monohydrochloride salt and HRMS data are shown.

Example 56a (7S,9aS)-7-(4-Fluoro-2-trifluoromethylphenoxy)methyl; mp 205°–206° C.; HRMS calcd for $C_{20}H_{21}F_5N_4O$: 428.1636, found: 428.1633.

Example 56b (7S,9aS)-7-(2-Bromo-4-fluorophenoxy)methyl; mp 228°–230° C.; HRMS calcd for $C_{19}H_{21}BrF_2N_4O$; 438.0867, found: 438.0862.

Example 56c (7S,9aS)-7-(2-Carbomethoxy-4-fluorophenoxy)methyl; mp 204°–205° C.; HRMS calcd for $C_{21}H_{24}F_2N_4O_3$: 418.1816, found: 418.1836.

Example 56d (7S,9aS)-7-(3,4-Difluorophenoxy)methyl-; mp 226°–227° C.; HRMS calcd for $C_{19}H_{21}F_3N_4O$: 378.1667, found: 378.1640.

Example 56e (7S,9aS)-7-(3,5-Difluorophenoxy)methyl-; mp 208°–211° C.; HRMS calcd for $C_{19}H_{21}F_3N_4O$: 378.1667, found: 378.1703.

Example 56f (7S,9aS)-7-(3-Trifluoromethoxyphenoxy)methyl-; mp 180°–184° C.; HRMS calcd for $C_{20}H_{23}F_4N_4O_2$ (MH+): 427.1757, found: 427.1776.

Example 56g (7S,9aS)-7-(4-Trifluoromethylphenoxy)methyl-; mp 188°–193° C.; HRMS calcd for $C_{20}H_{23}F_4N_4O$ (MH+): 411.1803, found: 411.1803.

Example 56h (7S,9aS)-7-(3-Methoxyphenoxy)methyl-; mp 229°–103° C.; HRMS calcd for $C_{20}H_{26}FN_4O_2$ (MH+): 373.2040, found: 373.2051.

Example 56i (7S,9aS)-7-(4-Methoxyphenoxy)methyl-; mp 220°–224° C.; HRMS calcd for $C_{20}H_{26}FN_4O_2$ (MH+): 373.2040, found: 373.2055.

Example 56j (7S,9aS)-7-(4-Ethylphenoxy)methyl-; mp 227°–229° C.; HRMS calcd for $C_{21}H_{28}FN_4O$ (MH+): 371.2247, found: 371.2228.

Example 56k (7S,9aS)-7-(2,4-Difluorophenoxy)methyl-; mp 222°–224° C.; HRMS calcd for $C_{19}H_{22}F_3N_4O$ (MH+): 379.1746, found: 379.1759.

Example 56l (7S,9aS)-7-(4-Carboexthoxy-phenoxy)methyl-; mp 230°–232° C.; HRMS calcd for $C_{22}H_{28}FN_4O_3$ (MH+): 415.2145, found: 415.2130.

Example 56m (7S,9aS)-7-(4-Bromo-2-methoxy-phenoxy)methyl-; mp 214°–216° C.; HRMS calcd for $C_{20}H_{25}BrFN_4O_2$ (MH+): 451.1145, found: 451.1108.

Example 56n (7S,9aS)-7-(3,4,5-Trifluoro-phenoxy)methyl-; mp 188°–191° C.; HRMS calcd for $C_{19}H_{21}F_4N_4O$ (MH+): 397.1651, found: 397.1667.

Example 56o (7S,9aS)-7-(3-Nitro-phenoxy)methyl-; mp 114°–119° C.; HRMS calcd for $C_{19}H_{23}FN_5O_3$ (MH+): 388.1785, found: 388.1799.

Example 56p (7S,9aS)-7-(3-Acetamido-phenoxy)methyl-; mp 162°–165° C.; HRMS calcd for $C_{21}H_{27}FN_5O_2$ (MH+): 400.2149, found: 400.2131.

Example 56q (7S,9aS)-7-(3-Trifluoromethyl-phenoxy)methyl-; mp 200°–202° C.; HRMS calcd for $C_{20}H_{23}F_4N_4O$ (MH+): 411.1808, found: 411.1781.

Example 56r (7S,9aS)-7-(3-Carbomethoxy-phenoxy)methyl-; mp 225°–226° C.; HRMS calcd for $C_{21}H_{26}FN_4O_3$ (MH+): 401.1989, found: 401.1989.

Example 56s (7S,9aS)-7-(3-(4-Morpholino)-phenoxy)methyl-; mp 233°–236° C.; HRMS calcd for $C_{23}H_{31}FN_5O_2$ (MH+): 428.2462, found: 428.2477.

Example 56t (7S,9aS)-7-(3-(1,1-Dimethyl)ethyl-phenoxy)methyl-; mp 252°–254° C.; HRMS calcd for $C_{23}H_{32}FN_4O$ (MH+): 399.2560, found: 399.2528.

Example 56u (7S,9aS)-7-(4-Fluoro-2-propyl-phenoxy)methyl-; mp 165°–170° C.; HRMS calcd for $C_{22}H_{28}F_2N_4O$: 402.2225, found: 402.2183.

Example 56v (7S,9aS)-7-(3-Methyl-phenoxy)methyl-; mp 90°–92° C.; HRMS calcd for $C_{20}H_{26}FN_4O$ (MH+): 357.2091, found: 357.2088.

Example 56w (7S,9aS)-7-(3-Dimethylamino-phenoxy)methyl-; mp 216°–220° C. (dec): HRMS calcd for $C_{21}H_{29}FN_5O$ (MH+): 386.2356, found: 386.2368.

Example 56x (7S,9aS)-7-(2-Methoxy-3-(1-methyl)ethyl-phenoxy)methyl-; mp 221°–223 C. (dec); HRMS calcd for $C_{23}H_{32}FN_4O_2$ (MH+): 415.2505, found: 415.2467.

Example 56y (7S,9aS)-7-(4-Acetamido-phenoxy)methyl-; mp 220°–223 C.; HRMS calcd for $C_{21}H_{27}FN_5O_2$ (MH+): 400.2143, found: 400.2136.

EXAMPLE 57

(7S,9aS)-7-(Substituted-phenoxy)methyl-2-(5-chloropyridin-2-yl)-2,3,4,6,7,8,9,9a-octahydro-1H-pyrido[1,2-a]pyrazines

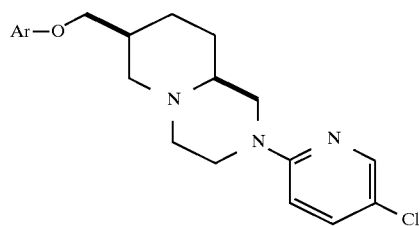

Compounds of the above formula were prepared according to Example 8 from (7S,9aS)-7-hydroxymethyl-2-(5-chloropyridin-2-yl)-2,3,4,6,7,8,9,9a-octahydro-1H-pyrido[1,2-a]pyrazine (Preparation 14) and the appropriate phenol. Purification was generally accomplished by flash silica gel chromatography using mixtures of ethyl acetate and hexane or mixtures of chloroform and methanol as the eluting solvent. The stereochemical configuration, 7-(substituted-phenoxy)methyl substituent, melting point of the monohydrochloride salt and HRMS data are shown.

Example 57a (7S,9aS)-7-(4-Fluorophenoxy)methyl; mp 244°–249° C.; HRMS calcd for $C_{20}H_{23}ClFN_3O$: 375.1508, found: 375.1490.

Example 57b (7S,9aS)-7-(3,5-Difluorophenoxy)methyl; mp 230°–233° C.; HRMS calcd for $C_{20}H_{22}ClF_2N_3O$: 393.1414, found: 393.1389.

PREPARATION 1

(7R,9aS)-7-Hydroxymethyl-2,3,4,6,7,8,9,9a-octahydro-1H-pyrido[1,2-a]pyrazine .2HCl

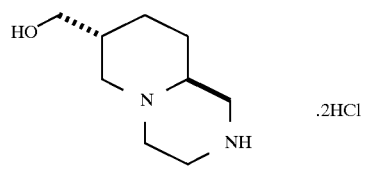

A solution of 4.0 g (15 mmol) (7R,9aS)-2-BOC-7-hydroxymethyl-2,3,4,6,7,8,9,9a-octahydro-1H-pyrido[1,2-a]pyrazine (WO 93/25552) in 40 mL of chloroform was treated with excess HCl(g) in ether. After stirring for 1 h, the solvent was evaporated to give 3.1 g (86%) of the hygroscopic dihyrochloride salt which was used without further purification in subsequent reactions. $^{13}C$ NMR (.2 HCl, d-$_6$ DMSO): δ 26.9, 28.8, 30.5, 44.9, 50.6, 54.7, 59.0, 61.1, 64.5. HRMS calcd for $C_9H_{18}N_2O$: 170.1419, found: 170.1414.

PREPARATION 2

(7S,9aS)-7-Hydroxymethyl-2,3,4,6,7,8,9,9a-octahydro-1H-pyrido[1,2-a]pyrazine

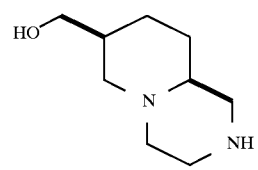

A solution of 5.84 g (21.6 mmol) of (7S,9aS)-N-BOC-7-hydroxymethyl-2,3,4,6,7,8,9,9a-octahydro-1H-pyrido[1,2- a]pyrazine (WO 93/25552) in 140 mL of trifluoroacetic acid and 60 mL of water was stirred at room temperature for 16 h. The mixture was concentrated and the residue dissolved in water. The aqueous phase saturated with solid sodium carbonate and extracted with chloroform (3x). The combined organic layers were dried (magnesium sulfate), filtered and evaporated to give 3.39 g (92%) of the title compound. This material was used without further purification for subsequent reactions. $^{13}$C NMR (base, d-$_6$ DMSO): δ 24.8, 25.1, 36.0, 45.7, 51.9, 56.1, 56.7, 62.0, 62.7.

PREPARATION 3
(7RS,9aSR)-7-Hydroxymethyl-2-(pyrimidin-2-yl)-2,3,4,6,7,8,9,9a-octahydro-1H-pyrido[1,2-a]pyrazine

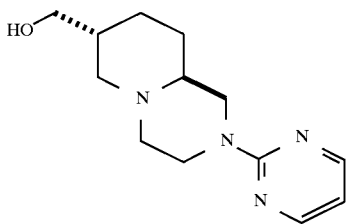

A mixture of 4.5 g (26 mmol) of (7RS,9aSR)-7-hydroxymethyl-2,3,4,6,7,8,9,9a-octahydro-1H-pyrido[1,2-a]pyrazine (U.S. Pat. No. 5,326,874), 3.0 g (26 mmol) of 2-chloropyrimidine, and 6.7 g (63 mmol) of sodium carbonate in 100 mL of water is heated at 95° C. for 16 h. The mixture was cooled to room temperature, extracted with methylene chloride (3x), the combined organic layers were washed with water and brine, dried, filtered and evaporated to give 4.68 g (72%) of the title compound which was used without purification in subsequent reactions.

PREPARATION 4
(7R,9aS)-7-Hydroxymethyl-2,3,4,6,7,8,9,9a-octahydro-2-(pyrimidin-2-yl)-1H-pyrido[1,2-a]pyrazine

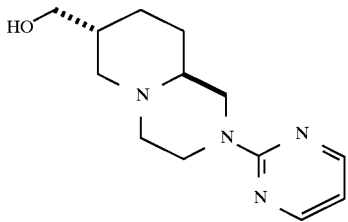

A mixture of 2.52 g (14.8 mmol) of (7R,9aS)-7-hydroxymethyl-2,3,4,6,7,8,9,9a-octahydro-1H-pyrido[1,2-a]pyrazine (Preparation 1), 1.70 g (14.8 mmol) of 2-chloropyrimidine and 6.91 g (65.2 mmol) of sodium carbonate in 150 mL of water was heated at 90° C. for 16 h.; then cooled and extracted with chloroform (3x). The organic layer was dried (magnesium sulfate), filtered and evaporated to give 3.25 g (89%) of the title compound which was used without purification in subsequent reactions.

PREPARATION 5
(7R,9aS)-7-Hydroxymethyl-2-(5-fluoropyrimidin-2-yl)-2,3,4,6,7,8,9,9a-octahydro-1H-pyrido[1,2-a]pyrazine

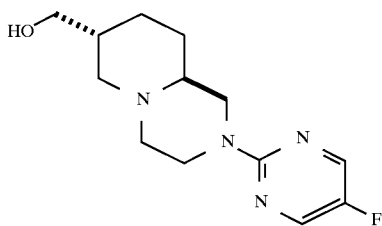

A solution of 4.41 g (18.2 mmol) of (7R,9aS)-7-hydroxymethyl-2,3,4,6,7,8,9,9a-octahydro-1H-pyrido[1,2-a]pyrazine dihyrochloride (Preparation 1), 3.78 g (28.5 mmol) of 2-chloro-5-fluoropyrimidine (B. Baasner, E. Klauke J. Fluroine Chem., 1989, 45, 417–430), and 9.07 g (85.6 mmol) of sodium carbonate in 180 mL of water were heated at 95° C. for 16 h. The mixture was cooled to room temperature, extracted with chloroform (2x), dried (magnesium sulfate), filtered and evaporated. Purification by flash chromatography on silica gel using 95:5 chloroform-:methanol gave 5.56 g (81%) of title compound. mp 148°–149.5° C. $^{13}$C NMR (CDCl$_3$): δ 26.8, 29.0, 39.1, 44.2, 49.7, 54.8, 58.7, 60.8, 66.2, 145.0, 145.3, 149.9, 153.2, 158.7. Anal calcd for $C_{13}H_{19}FN_4O$: C, 58.63; H, 7.19; N, 21.04; found: C, 58.36; H, 7.18; N, 20.87.

PREPARATION 6
(7RS,9aSR)-7-Hydroxymethyl-2,3,4,6,7,8,9,9a-octahydro-2-(5-fluoro-4-thiomethylpyrimidin-2-yl)-1H-pyrido[1,2-a]pyrazine

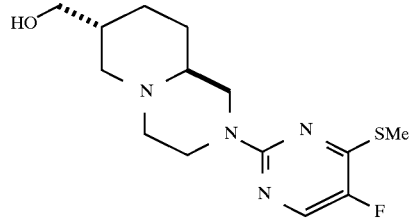

The title compound was synthesized according to Preparation 5 from (7RS,9aSR)-7-hydroxymethyl-2,3,4,6,7,8,9,9a-octahydro-1H-pyrido[1,2-a]pyrazine (U.S. Pat. No. 5,326,874) and 2-chloro-5-fluoro-4-thiomethylpyrimidine (Uchytilova, V.; Holy, A.; Cech, D.; Gut, J. Coll. Czech. Chem. Commun., 1975, 40, 2347. Ueda, T.; Fox, J. J. J. Med. Chem., 1963, 6, 697), and was used for subsequent reactions without purification.

PREPARATION 7
(7R,9aS)-2-BOC-7-(4-Fluorophenoxy)methyl-2,3,4,6,7,8,9,9a-octahydro-1H-pyrido[1,2-a]pyrazine

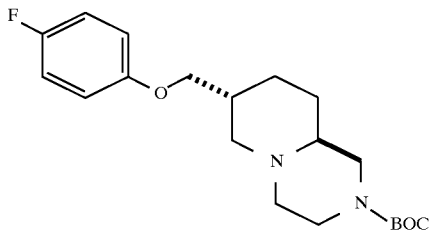

A solution of 12.0 g (44.4 mmol) of (7R,9aS)-2-BOC-7-hydroxymethyl-2,3,4,6,7,8,9,9a-octahydro-1H-pyrido[1,2-a]pyrazine (WO 93/25552), 7.47 g (66.7 mmol) of 4-fluorophenol, 14.0 g (53.3 mmol) of triphenylphosphine in 450 mL of THF was treated with 8.40 mL (53.3 mmol) of diethyl azodicarboxylate and stirred at room temperature for 16 h. The mixture was diluted with ethyl acetate and treated with HCl(g) in ethyl ether until precipitation ceased. The solvent was evaporated and the solid residue was repeatedly washed with 1:1 ethyl acetate:ethyl ether. The residue was dissolved in chloroform and washed with 15% NaOH. The organic phase was dried (magnesium sulfate), filtered and evaporated to give 15.9 g of yellow-white crystals. The crude product was dissolved in 1:1 hexane:ethyl acetate and filtered through a plug of silica gel to give 13.3 g (82%) of the title compound. mp 90°–92° C. $^{13}$C NMR (CDCl$_3$): δ 26.9, 28.4, 28.8, 54.8, 58.7, 60.8, 71.6, 79.7, 115.33, 115.44, 115.58, 115.89, 154.6, 155.1, 155.6, 158.8. Anal calcd for C$_{20}$H$_{29}$FN$_2$O$_3$: C, 65.91; H, 8.02; N, 7.69; found: C, 65.90; H, 8.06; N, 7.77.

PREPARATION 8
(7R,9aS)-7-(4-Fluorophenoxy)methyl-2,3,4,6,7,8,9,9a-octahydro-1H-pyrido[1,2-a]pyrazine

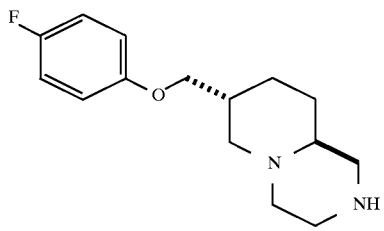

A solution of 44.4 g (122 mmol) of (7R,9aS)-2-BOC-7-(4-fluorophenoxy)methyl-2,3,4,6,7,8,9,9a-octahydro-1H-pyrido[1,2-a]pyrazine (Preparation 7) in 500 mL of trifluroacetic acid and 200 mL of water was stirred at room temperature for 16 h. The mixture was concentrated by evaporation, the residue dissolved in water, basified with 15% NaOH, and extracted with ethyl acetate (2×). The organic layers were dried (magnesium sulfate), filtered and evaporated to give 31.4 g (96%) of (7R,9aS)-7-(4-fluorophenoxy)methyl-2,3,4,6,7,8,9,9a-octahydro-1H-pyrido[1,2-a]pyrazine which was suitable for use in subsequent reactions. Purification of a 0.40 g sample by flash silica gel chromatography eluting with 90:10 chloroform-:methanol gave 0.38 g of colorless crystals. mp (.2 HCl) 200°–201° C. $^{13}$C NMR (base, CDCl$_3$): δ 27.2, 29.1, 36.3, 45.9, 51.9, 56.0, 59.1, 62.5, 71.7, 115.4 (d, $J_{CF}$=8), 115.7 (d, $J_{CF}$=23) HRMS calcd for C$_{15}$H$_{21}$FN$_2$O: 264.1638, found: 264.1660.

PREPARATION 9
(7S,9aR)-7-(4-Fluorophenoxy)methyl-2,3,4,6,7,8,9,9a-octahydro-1H-pyrido[1,2-a]pyrazine .2 HCl

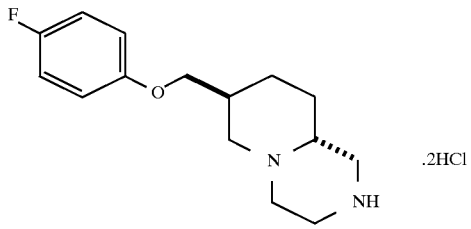

A solution of 0.39 g (1.4 mmol) of (7S,9aR)-2-BOC-7-hydroxymethyl-2,3,4,6,7,8,9,9a-octahydro-1H-pyrido[1,2-a]pyrazine, 0.24 g (2.2 mmol) of 4-fluorophenol and 0.45 g (1.7 mmol) of triphenyl phosphine in 20 mL of dry THF was treated with 0.27 mL (1.7 mmol) of diethyl azodicarboxylate, and stirred at ambient temperature for 16 h. The solution was diluted with ethyl acetate and treated with excess HCl(g) in ethyl ether. The solvent was evaporated and the white, solid residue was washed with 1:1 ethyl acetate:ethyl ether. The solid remaining was dissolved in chloroform and washed with 1M NaOH, dried (magnesium sulfate), filtered and evaportated to give 0.45 g of (7S,9aR)-2-BOC-7-(4-fluorophenoxy)methyl-2,3,4,6,7,8,9,9a-octahydro-1H-pyrido[1,2-a]pyrazine.

A solution of 0.44 g (1.2 mmol) of (7S,9aR)-2-BOC-7-(4-fluorophenoxy)methyl-2,3,4,6,7,8,9,9a-octahydro-1H-pyrido[1,2-a]pyrazine in 25 mL of chloroform was treated with excess HCl(g) in ethyl ether and stirred at ambient temperature for 2 h. The solvent was evaporated to give 0.40 g of title compound as the dihydrochloride salt which was used for subsequent reactions without purification.

PREPARATION 10
(7R,9aR)-7-(4-Fluorophenoxy)methyl-2,3,4,6,7,8,9,9a-octahydro-1H-pyrido[1,2-a]pyrazine

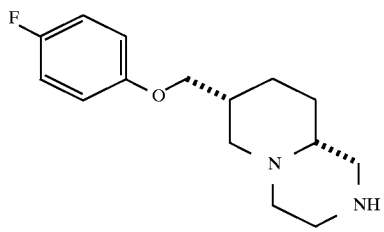

A solution of 0.71 g (2.63 mmol) of (7R,9aR)-2-BOC-7-hydroxymethyl-2,3,4,6,7,8,9,9a-octahydro-1H-pyrido[1,2-a]pyrazine, 0.44 g (3.94 mmol) of 4-fluorophenol and 0.83 g (3.16 mmol) of triphenylphosphine in 25 mL of THF was treated with 0.50 mL (3.16 mmol) of diethyl azodicarboxylate and stirred at ambient temperature for 16 h. The solvent was evaporated, the residue dissolved in ethyl acetate and washed with 1M NaOH (2×). The organic layer was dried (magnesium sulfate), filtered and evaporated. Purification by flash chromatography with 75:25 ethyl acetate:hexane gave 0.5 g of a sticky solid. This material was dissolved in chloroform, washed with 1M NaOH, dried (magnesium sulfate), filtered and evaporated to tive 0.20 g of (7R,9aR)-2-BOC-7-(4-fluorophenoxy)methyl-2,3,4,6,7,8,9,9a-octahydro-1H-pyrido[1,2-a]pyrazine.

A solution of 0.20 g (0.55 mmol) of (7R,9aR)-2-BOC-7-(4-fluorophenoxy)methyl-2,3,4,6,7,8,9,9a-octahydro-1H-pyrido[1,2-a]pyrazine in 10 mL of trifluoroacetic acid and 3 mL of water was stirred at ambient temperature for 4 h. The mixture was concentrated in vacuo and the residue diluted with water. The solution was adjusted to pH 12 with 15% NaOH, and extracted with ethyl acetate (2×). The organic phase was dried (magnesium sulfate), filtered and evaporated to give 0.149 g of the title compound which was used without further purification for subsequent reactions.

PREPARATION 11
(7RS,9aSR)-7-Hydroxymethyl-2,3,4,6,7,8,9,9a-octahydro-2-(pyridin-2-yl)-1H-pyrido[1,2-a]pyrazine

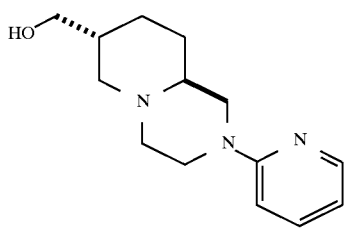

A mixture of 1.0 g (5.9 mmol) of (7RS,9aSR)-7-hydroxymethyl-2,3,4,6,7,8,9,9a-octahydro-1H-pyrido]1,2-a]pyrazine (U.S. Pat. No. 5,326,874); 4.6 g (29 mmol) of 2-bromo-pyridine, 1.5 g (14 mmol) of sodium carbonate and 50 mL of isoamyl alcohol were refluxed for 18 h. The mixture was cooled to room temperature, filtered, and concentrated in vacuo. The residue was dissolved in ethyl acetate and washed with saturated sodium carbonate. The organic layer was dried (magnesium sulfate), filtered and evaporated, and the crude product was purified by flash chromatography on silica gel eluting first with chloroform followed by 95:5 chloroform:methanol to give 0.61 g (42%) of the title compound. $^{13}$C NMR (base, CDCl$_3$): δ 26.8, 29.0, 39.0, 45.1, 50.7, 54.8, 58.7, 60.8, 66.0, 107.1, 113.3, 137.5, 147.9, 159.3.

PREPARATION 12
3-[(7R,9aS)-2,3,4,6,7,8,9,9a-Octahydro-1H-pyrido[1,2-a]-pyrazin -7-ylmethyl]-3H-benzoxazol-2-one

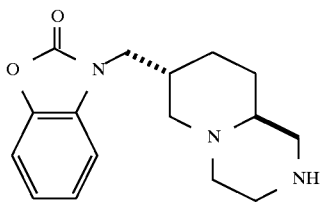

A solution of 5.0 g (18.5 mmol) of (7R,9aS)-2-BOC-7-hydroxymethyl-2,3,4,6,7,8,9,9a-octahydro-1H-pyrido[1,2-a]pyrazine (WO 93/25552) and 2.84 mL (20.4 mmol) of triethylamine in 200 mL of dry methylene chloride was chilled to 0° C. and treated with a solution of 1.50 mL (19.4 mmol) of methanesulfonyl chloride in 75 mL of methylene chloride. After 1 h, the mixture was diluted with water, basified to pH 12 with 15% sodium hydroxide, the layers were separated, and the aqueous layer extracted with methylene chloride. The combined organic phase was washed with brine, dried (magnesium sulfate), filtered and evaporated the give 6.4 g (100%) of mesylate.

A solution of 7.00 g (51.8 mmol) of 2-benzoxazolinone in 180 mL of DMF was treated with 2.05 g (51.3 mmol) of sodium hydride (60% oil dispersion) and the mixture stirred at 50° C. for 1.5 h. The heat source was temporarily removed, a solution of 6.4 g (18 mmol) of the above mesylate in 180 mL of DMF was added and the mixture heated at 100° C. for 2 h. The reaction was cooled to room temperature, diluted with water, acidified to pH 2 with 6M hydrochloric acid and washed with ethyl acetate (2×). The pH was adjusted to 12 with conc. ammonium hydroxide and the aqueous phase extracted with ethyl acetate (3×). The combined organics were dried (magnesium sulfate), filtered and evaporated. Purification by flash silica gel chromatography with ethyl acetate gave 3.55 g (50%) of 3-[(7R,9aS) -2-BOC-2,3,4,6,7,8,9,9a-octahydro-1H-pyrido[1.2-a]-pyrazin-7-ylmethyl]-3H-benzooxazol-2-one.

A solution of 3.1 g (8.01 mmol) of 3-[(7R,9aS)-2-BOC-2,3,4,6,7,8,9,9a-octahydro-1H-pyrido[1,2-a]-pyrazin-7-ylmethyl]-3H-benzooxazol-2-one in 40 mL of chloroform was stirred with excess HC$_1$ (g) in ethyl ether for 2 h at ambient temperature. The solvent was evaporated to give 2.3 g (100%) of the title compound dihydrochloride which was used for subsequent reactions without further purification.

PREPARATION 13
(7S,9aS)-7-Hydroxymethyl-2-(5-fluoropyrimidin-2-yl)-2,3,4,6,7,8,9,9a-octahydro-1H-pyrido[1,2-a]pyrazine

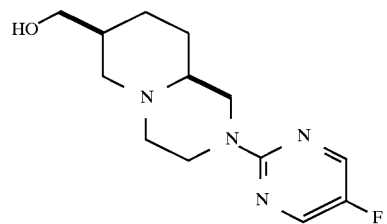

A mixture of 2.31 g (13.6 mmol) of (7S,9aS)-7-hydroxymethyl-2,3,4,6,7,8,9,9a-octahydro-1H-pyrido[1,2-a]pyrazine (Preparation 2), 1.98 g (15.0 mmol) of 2-chloro-5-fluoropyrimidine (B. Baasner, E. Klauke, *J. Fluorine Chem.*, 1989, 45, 417), 4.32 g (40.8 mmol) of sodium carbonate and 50 mL of water was heated at reflux for 16 h. The mixture was cooled to room temperature and extracted with chloroform (3×). The combined organic layers were dried (magnesium sulfate), filtered and evaporated. Purification by flash silica gel chromatography with 95:5 chloroform:methanol gave 2.7 g (75%) of the title compound. mp (base) 111°–112° C. $^{13}$C NMR (base, CDCl$_3$): δ 26.5, 27.3, 34.2, 44.3, 49.8, 54.8, 58.8, 60.7, 68.2, 145.0, 145.3, 149.9, 153.2, 158.6. HRMS calcd for $C_{13}H_{19}FN_4O$: 266.1543, found: 266.1530.

PREPARATION 14
(7S,9aS)-7-Hydroxymethyl-2-(5-chloropyridin-2-yl)-2,3,4,6,7,8,9,9a-octahydro-1H-pyrido[1,2-a]pyrazine

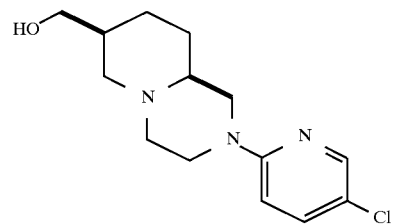

A mixture of 2.5 g (10.3 mmol) of (7S,9aS)-7-hydroxymethyl-2,3,4,6,7,8,9,9a-octahydro-1H-pyrido[1,2-a]pyrazine dihydrochloride, 7.62 g (51.5 mmol) of 2,5-dichloropyridine, 5.45 g (51.5 mmol) of sodium carbonate and 100 mL of isoamyl alcohol was heated at reflux for 72 h. The mixture was cooled, the mixture filtered to remove solids and the solvent evaporated in vacuo. Purification by flash silica gel chromatography using 95:5 chloroform-:methanol gave 1.72 g (59%) of the title compound. mp (base) 61°–62° C. $^{13}$C NMR (base, CDCl$_3$): δ 26.6, 27.2, 34.3, 45.4, 50.9, 54.6, 58.4, 60.5, 68.0, 107.7, 120.1, 137.1, 146.2, 157.5. HRMS calcd for $C_{14}H_{20}ClN_3O$: 281.1295, found: 281.1298.

PREPARATION 15
(7R,9aS)-7-Hydroxymethyl-2-(5-chloropyridin-2-yl)-2,3,4,6,7,8,9,9a-octahydro-1H-pyrido[1,2-a]pyrazine

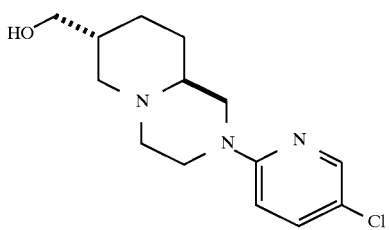

A mixture of 1.35 g (5.56 mmol) of (7R,9aS)-7-hydroxymethyl-2,3,4,6,7,8,9,9a-octahydro-1H-pyrido[1,2-a]pyrazine dihyrochloride (Preparation 1), 4.11 g (27.8 mmol) of 2,5-dichloropyridine, 2.94 g (27.8 mmol) of sodium carbonate and 60 mL of isoamyl alcohol was heated at reflux for 48 h. The mixture was cooled and the solvent removed in vacuo. Purification by flash silica gel chromatography with 95:5 chloroform: methanol gave 1.02 g (65%) of the title compound mp (base) 139.0°–140.5° C. $^{13}$C NMR (CDCl$_3$): δ 26.8, 29.1, 39.1, 45.3, 50.8, 54.6, 58.6, 60.6, 66.2, 107.7, 120.1, 137.1, 146.2, 157.6.

We claim:

1. A compound of the formula

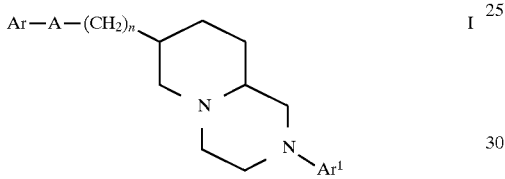

wherein Ar is phenyl, naphthyl, benzoxazolonyl, indolyl, indolonyl, benzimidazolyl, quinolyl, furyl, benzofuryl, thienyl, benzothienyl, oxazolyl, benzoxazolyl;

Ar$^1$ is phenyl, pyridinyl, pyridazinyl, pyrimidinyl, or pyrazinyl;

A is O, S, SO, SO$_2$, C=O, CHOH, or -(CR$^3$R$^4$)-;

n is 0, 1 or 2;

each of Ar and Ar$^1$ may be independently and optionally substituted with one to four substituents independently selected from the groups consisting of fluoro, chloro, bromo, iodo, cyano, nitro, thiocyano, —SR, —SOR, —SO$_2$R, —NHSO$_2$R, -(C$_1$–C$_6$)alkoxy, —NR$^1$R$^2$, —NRCOR$^1$, —CONR$^1$R$^2$, Ph, —COR, COOR, -(C$_1$–C$_6$)alkyl, -(C$_1$–C$_6$)alkyl substituted with one to six halogens, -(C$_3$–C$_6$)cycloalkyl, and trifluoromethoxy;

each and every R, R$^1$, and R$^2$ is independently selected from the group consisting of hydrogen, -(C$_1$–C$_6$)alkyl, -(C$_1$–C$_6$)alkyl substituted with one to thirteen halogens selected from fluorine, chlorine, bromine and iodine, phenyl, benzyl, -(C$_2$–C$_6$)alkenyl, -(C$_3$–C$_6$)cycloalkyl, and -(C$_1$–C$_6$)alkoxy;

each and every R$^3$ and R$^4$ is independently selected from a group consisting of hydrogen, methyl, ethyl, n-propyl, and i-propyl;

diastereomeric and optical isomers thereof; and pharmaceutically acceptable salts thereof.

2. A compound of claim 1 wherein

Ar is phenyl, naphthyl, benzoxazolonyl, indolyl, indolonyl, benzimidazolyl, or quinolyl;

A is O, S, SO$_2$, C=O, CHOH, or CH$_2$;

n is 0 or 1;

wherein Ar and Ar$^1$ may be independently substituted with up to three substituents independently selected from the group consisting of fluoro, chloro, cyano, —NR$^1$R$^2$, -(C$_1$–C$_6$)alkoxy, —COOR, —CONR$^1$R$^2$, and -(C$_1$–C$_6$)alkyl or a pharmaceutically acceptable salt thereof.

3. A compound of claim 2 wherein

A is O or S;

n is 1;

Ar is phenyl or substituted phenyl or a pharmaceutically acceptable salt thereof.

4. A compound of claim 2 wherein

A is CH$_2$;

n is 0;

Ar is benzoxazolonyl or substituted benzoxazolonyl or a pharmaceutically acceptable salt thereof.

5. A compound of claim 2 wherein

A is CH$_2$;

n is 0;

Ar is indolyl or substituted indolyl or a pharmaceutically acceptable salt thereof.

6. A compound of claim 2 wherein

A is C=O or CHOH;

n is 0 or 1;

Ar is phenyl or substituted phenyl or a pharmaceutically acceptable salt thereof.

7. A compound of claim 3 wherein

A is O;

Ar is fluorophenyl, difluorophenyl or cyanophenyl;

Ar$^1$ is chloropyridinyl or a pharmaceutically acceptable salt thereof.

8. A compound of claim 3 wherein

A is O;

Ar is fluorophenyl, difluorophenyl or cyanophenyl;

Ar$^1$ is fluoropyrimidinyl or a pharmaceutically acceptable salt thereof.

9. A compound of claim 3 wherein

A is O;

Ar is fluorophenyl, difluorophenyl or cyanophenyl;

Ar 1 is fluorophenyl or a pharmaceutically acceptable salt thereof.

10. A compound of claim 4 wherein

Ar$^1$ is 5-chloro-pyridin-2-yl or a pharmaceutically acceptable salt thereof.

11. A compound of claim 4 wherein

Ar$^1$ is 5-fluoro-pyrimidin-2-yl or a pharmaceutically acceptable salt thereof.

12. A compound of claim 5 wherein

Ar$^1$ is 5-fluoro-pyrimidin-2-yl.

13. A compound of claim 7 wherein

Ar$^1$ is 5-chloro-pyridin-2-yl.

14. A compound of claim 8 wherein

Ar$^1$ is 5-fluoro-pyrimidin-2-yl.

15. A compound of claim 1 selected from the group consisting of (7R,9aS)-7-(4-fluorophenoxy)methyl-2-(5-chloro-pyridin-2-yl)-2,3,4,6,7,8,9,9a-octahydro-1H-pyrido[1,2-a]pyrazine;

(7R,9aS)-7-(3,5-difluorophenoxy)methyl-2-(5-chloro-pyridin-2-yl)-2,3,4,6,7,8,9,9a-octahydro-1H-pyrido[1,2-a]pyrazine:

3-[(7R,9aS)-2-(5-chloro-pyridin-2-yl)-2,3,4,6,7,8,9,9a-octahydro-1H-pyrido[1,2-a]pyrazin-7-ylmethyl]-3H-benzooxazol-2-one;

3-[(7R,9aS)-2-(5-fluoro-pyrimidin-2-yl)-2,3,4,6,7,8,9,9a-octahydro-1H-pyrido[1,2-a]pyrazin-7-ylmethyl]-3H-benzoxazol-2-one;

(7R,9aS)-7-(4-fluorophenoxy)methyl-2-(5-fluoro-pyrimidin-2-yl)-2,3,4,6,7,8,9,9a-octahydro-1H-pyrido[1,2-a]pyrazine;

(7R,9aS)-7-(3,5-difluorophenoxy)methyl-2-(5-fluoro-pyrimidin-2-yl)-2,3,4,6,7,8,9,9a-octahydro-1H-pyrido[1,2-a]pyrazine;

(7R,9aS)-7-(3,4-difluorophenoxy)methyl-2-(5-fluoro-pyrimidin-2-yl)-2,3,4,6,7,8,9,9a-octahydro-1H-pyrido[1,2-a]pyrazine;

(7R,9aS)-7-(3-cyanophenoxy)methyl-2-(5-fluoro-pyrimidin-2-yl)-2,3,4,6,7,8,9,9a-octahydro-1H-pyrido[1,2-a]pyrazine;

(7R,9aS)-7-(4-cyanophenoxy)methyl-2-(5-fluoro-pyrimidin-2-yl)-2,3,4,6,7,8,9,9a-octahydro-1H-pyrido[1,2-a]pyrazine;

(7R,9aS)-7-(4-iodophenoxy)methyl-2-(5-fluoro-pyrimidin-2-yl)-2,3,4,6,7,8,9,9a-octahydro-1H-pyrido[1,2-a]pyrazine;

(7R,9aS)-7-(4-fluorophenoxy)methyl-2-(4-fluorophenyl)-2,3,4,6,7,8,9,9a-octahydro-1H-pyrido[1,2-a]pyrazine;

(7S,9aS)-7-(4-fluorophenoxy)methyl-2-(5-fluoro-pyrimidin-2-yl)-2,3,4,6,7,8,9,9a-octahydro-1H-pyrido[1,2-a]pyrazine;

(7S,9aS)-7-(2-carbomethoxy-4-fluorophenoxy)methyl-2-(5-fluoro-pyrimidin-2-yl)-2,3,4,6,7,8,9,9a-octahydro-1H-pyrido[1,2-a]pyrazine;

(7S,9aS)-7-(2-bromo-4-fluorophenoxy)methyl-2-(5-fluoro-pyrimidin-2-yl)-2,3,4,6,7,8,9,9a-octahydro-1H-pyrido[1,2-a]pyrazine;

(7S,9aS)-7-(4-fluoro-2-trifluoromethylphenoxy)methyl-2-(5-fluoro-pyrimidin-2-yl)-2,3,4,6,7,8,9,9a-octahydro-1H-pyrido[1,2-a]pyrazine;

(7S,9aS)-7-(3,5-difluorophenoxy)methyl-2-(5-chloro-pyridin-2-yl)-2,3,4,6,7,8,9,9a-octahydro-1H-pyrido[1,2-a]pyrazine;

(7S,9aS)-7-(4-fluorophenoxy)methyl-2-(5-chloro-pyridin-2-yl)-2,3,4,6,7,8,9,9a-octahydro-1H-pyrido[1,2-a]pyrazine;

(7S,9aS)-7-(4-fluoro-2-methylphenoxy)methyl-2-(5-fluoro-pyrimidin-2-yl)-2,3,4,6,7,8,9,9a-octahydro-1H-pyrido[1,2-a]pyrazine;

(7S,9aS)-7-(2,4-difluorophenoxy)methyl-2-(5-fluoro-pyrimidin-2-yl)-2,3,4,6,7,8,9,9a-octahydro-1H-pyrido[1,2-a]pyrazine;

(7S,9aS)-7-(3-methyl-phenoxy)methyl-2-(5-fluoropyrimidin-2-yl)-2,3,4,6,7,8,9,9a-octahydro-1H-pyrido[1,2-a]pyrazine;

(7S,9aS)-7-(3,4-difluoro-phenoxy)methyl-2-(5-fluoropyrimidin-2-yl)-2,3,4,6,7,8,9,9a-octahydro-1H-pyrido[1,2-a]pyrazine;

(7S,9aS)-7-(3,5-difluoro-phenoxy)methyl-2-(5-fluoropyrimidin-2-yl)-2,3,4,6,7,8,9,9a-octahydro-1H-pyrido[1,2-a]pyrazine;

(7S,9aS)-7-(3-cyano-phenoxy)methyl-2-(5-fluoropyrimidin-2-yl)-2,3,4,6,7,8,9,9a-octahydro-1H-pyrido[1,2-a]pyrazine;

(7S,9aS)-7-(3-trifluoromethyl-phenoxy)methyl-2-(5-fluoropyrimidin-2-yl)-2,3,4,6,7,8,9,9a-octahydro-1H-pyrido[1,2-a]pyrazine;

(7S,9aS)-7-(4-trifluoromethyl-phenoxy)methyl-2-(5-fluoropyrimidin-2-yl)-2,3,4,6,7,8,9,9a-octahydro-1H-pyrido[1,2-a]pyrazine;

(7S,9aS)-7-(3-trifluoromethoxy-phenoxy)methyl-2-(5-fluoropyrimidin-2-yl)-2,3,4,6,7,8,9,9a-octahydro-1H-pyrido[1,2-a]pyrazine;

(7S,9aS)-7-(3-methoxy-phenoxy)methyl-2-(5-fluoropyrimidin-2-yl)-2,3,4,6,7,8,9,9a-octahydro-1H-pyrido[1,2-a]pyrazine;

(7S,9aS)-7-(4-methoxy-phenoxy)methyl-2-(5-fluoropyrimidin-2-yl)-2,3,4,6,7,8,9,9a-octahydro-1H-pyrido[1,2-a]pyrazine;

and pharmaceutically acceptable salts thereof.

16. A pharmaceutical composition for treating or preventing a disease or condition, the treatment or prevention of which can be effected or facilitated by altering dopamine mediated neurotransmission in a mammal, comprising a $D_4$ receptor binding effective amount of a compound according to claim 1 or a pharmaceutically acceptable salt thereof and a pharmaceutically acceptable carrier.

17. A method of treating schizophrenia which comprises administering to a mammal in need of such treatment an effective amount of a compound of claim 1 or a pharmaceutically acceptable salt thereof.

* * * * *